(12) United States Patent
Hayward

(10) Patent No.: US 11,631,499 B2
(45) Date of Patent: *Apr. 18, 2023

(54) ESTIMATING IMPACT OF PROPERTY ON INDIVIDUAL HEALTH—PROPERTY SCORE

(71) Applicant: William E. Hayward, Carmel, CA (US)

(72) Inventor: William E. Hayward, Carmel, CA (US)

( * ) Notice: Subject to any disclaimer, the term of this patent is extended or adjusted under 35 U.S.C. 154(b) by 350 days.

This patent is subject to a terminal disclaimer.

(21) Appl. No.: 15/931,402

(22) Filed: May 13, 2020

(65) Prior Publication Data
US 2020/0279653 A1 Sep. 3, 2020

Related U.S. Application Data

(63) Continuation of application No. 15/289,473, filed on Oct. 10, 2016, now Pat. No. 10,706,969, which is a
(Continued)

(51) Int. Cl.
*G16H 50/30* (2018.01)
*G16H 10/20* (2018.01)
(Continued)

(52) U.S. Cl.
CPC ......... *G16H 50/30* (2018.01); *G06F 3/04842* (2013.01); *G06Q 10/00* (2013.01);
(Continued)

(58) Field of Classification Search
CPC ........ G16H 10/00; G16H 10/40; G16H 15/00; G16H 20/00; G16H 20/10; G16H 20/13;
(Continued)

(56) References Cited

U.S. PATENT DOCUMENTS 5,808,916 A 9/1998 Orr et al.
6,652,455 B1 11/2003 Kocher
(Continued)

OTHER PUBLICATIONS

U.S. Final Office Action for U.S. Appl. No. 16/208,460 dated Nov. 19, 2020.
(Continued)

*Primary Examiner* — Robert W Morgan
*Assistant Examiner* — Charles P Coleman
(74) *Attorney, Agent, or Firm* — Sherman IP LLP; Kenneth L. Sherman; Hemavathy Perumal

(57) ABSTRACT

Embodiment of the invention provide a method for determining a health index of a property area. The method comprises acquiring property data associated with a property area from a data source, and extracting a first property attribute data from the property data acquired. The first property attribute data extracted is used to determine presence or movement of a first pollutant data within the property area. The method further comprises determining a first potential impact data the first pollutant data may have on individual health based in part on the first property attribute data extracted, and computing a property score representing a health index of the property area based in part on the first potential impact data determined.

20 Claims, 22 Drawing Sheets

PROPERTY ATTRIBUTES QUESTIONS (265A)
- Does the property have forced air?
- Does the property have an attic?
- Does the property have stucco walls?
- Does the property have crawl space?
- Does the property have one or more fireplaces?
- Does the property have air-conditioning?
- Does the property have carpet?
- How old is the property?
- How many rooms does the property have?
- Did the property have a recent water leak?
- How often does the property have water leaks?

PET QUESTIONS (265C)
- Are there any pets on the property?
- Did any prior occupants of the property have pets?,
- How many pets are there on the property?
- What type of pets are on the property?
- Where on the property are the pets allowed?

PROXIMITY QUESTIONS (265B)
- How far is the property from the nearest freeway?
- Is the property within proximity of one or more industries or factories?
- Is the property within proximity of one or more restaurants?
- Is the property within proximity of one or more dry cleaners?
- Does the property share walls with one or more other properties (e.g., units) that have pets?

USER BEHAVIORAL QUESTIONS (265D)
- Do you feel better when you leave the property for a couple of days or even a few hours?
- Do you avoid or no longer use certain rooms in the property?
- Do you use air fresheners?
- Do you cook with gas?
- Do you run bathroom fans after bathing?

Related U.S. Application Data continuation of application No. 14/745,329, filed on Jun. 19, 2015, now abandoned.

(60) Provisional application No. 62/015,322, filed on Jun. 20, 2014.

(51) Int. Cl.
    *G06V 10/40*         (2022.01)
    *G06F 3/04842*     (2022.01)
    *G06Q 10/00*         (2012.01)
    *G06Q 50/16*         (2012.01)
    *G16H 10/60*         (2018.01)

(52) U.S. Cl.
CPC ............ *G06Q 50/16* (2013.01); *G06Q 50/163* (2013.01); *G06V 10/40* (2022.01); *G16H 10/20* (2018.01); *G06T 2207/10004* (2013.01); *G16H 10/60* (2018.01); *Y02A 90/10* (2018.01)

(58) Field of Classification Search
CPC ........ G16H 20/17; G16H 30/00; G16H 40/00; G16H 50/00; G16H 70/00; G16H 80/00; G16H 50/30; G16H 10/20; G16H 10/60; G06Q 50/22–24; G06Q 10/00; G06Q 50/16; G06Q 50/163; G06V 10/40; G06F 3/04842; Y02A 90/10; G06T 2207/10004
USPC .................................................. 705/2, 3, 20
See application file for complete search history.

(56) References Cited

U.S. PATENT DOCUMENTS

| | | | |
|---|---|---|---|
| 6,693,546 | B2 | 2/2004 | Skardon et al. |
| 8,027,850 | B1 | 9/2011 | Pietrzak |
| 2001/0039506 | A1 | 11/2001 | Robbins |
| 2002/0007336 | A1 | 1/2002 | Robbins |
| 2002/0035486 | A1* | 3/2002 | Huyn .................. G09B 7/02 705/3 |
| 2006/0000257 | A1 | 1/2006 | Samadpour et al. |
| 2006/0286518 | A1 | 12/2006 | Yoder |
| 2007/0088507 | A1 | 4/2007 | Haberlen et al. |
| 2008/0004915 | A1* | 1/2008 | Brown ................. G06Q 10/067 705/4 |
| 2008/0255862 | A1 | 10/2008 | Bailey et al. |
| 2009/0112525 | A1 | 4/2009 | Adani |
| 2010/0082362 | A1 | 4/2010 | Salsbury et al. |
| 2011/0174054 | A1 | 7/2011 | Lynn |
| 2011/0276499 | A1 | 11/2011 | Walsh et al. |
| 2011/0295624 | A1 | 12/2011 | Chapin et al. |
| 2011/0318717 | A1 | 12/2011 | Adamowicz |
| 2012/0084092 | A1 | 4/2012 | Kozuch et al. |
| 2013/0031011 | A1 | 1/2013 | Lee |
| 2013/0038470 | A1* | 2/2013 | Niemeyer .......... G01N 33/0075 340/870.11 |
| 2013/0282511 | A1 | 10/2013 | Mitchell et al. |
| 2014/0142456 | A1* | 5/2014 | Fischer .................. A61B 5/091 600/538 |
| 2015/0370987 | A1 | 12/2015 | Hayward |
| 2015/0370988 | A1 | 12/2015 | Hayward |
| 2015/0370989 | A1 | 12/2015 | Hayward |
| 2015/0370990 | A1 | 12/2015 | Hayward |
| 2015/0371347 | A1 | 12/2015 | Hayward |
| 2019/0172164 | A1 | 6/2019 | Hayward |

OTHER PUBLICATIONS

U.S. Corrected Notice of Allowability for U.S. Appl. No. 14/745,330 dated Jun. 10, 2020.
U.S. Corrected Notice of Allowability for U.S. Appl. No. 14/745,337 dated Jun. 10, 2020.
U.S. Corrected Notice of Allowability for U.S. Appl. No. 14/745,337 dated Jul. 16, 2020.
U.S. Corrected Notice of Allowance for U.S. Appl. No. 14/745,338 dated Jun. 4, 2020.
U.S. Non-Final Office Action for U.S. Appl. No. 16/208,460 dated Jun. 8, 2020.
U.S. Corrected Notice of Allowance for U.S. Appl. No. 15/289,473 dated Jun. 10, 2020.
Della Cava, M., "Meet USA Today's Entrepreneur of the Year", USA Today, Dec. 11, 2014, p. 1, United States [downloaded from http://www.usatoday.com/story/tech/2014/12/11/porchcom-usa-today-entrepreneur-of-the-year/20203863/ on Mar. 24, 2016].
U.S. Non-Final Office Action for U.S. Appl. No. 14/745,330 dated Oct. 19, 2017.
U.S. Non-Final Office Action for U.S. Appl. No. 14/745,331 dated Nov. 3, 2017.
U.S. Non-Final Office Action for U.S. Appl. No. 14/745,334 dated Oct. 20, 2017.
U.S. Non-Final Office Action for U.S. Appl. No. 14/745,337 dated Oct. 20, 2017.
U.S. Non-Final Office Action for U.S. Appl. No. 14/745,338 dated Oct. 20, 2017.
U.S. Non-Final Office Action for U.S. Appl. No. 14/745,329 dated Oct. 20, 2017.
U.S. Final Office Action for U.S. Appl. No. 14/745,329 dated Jun. 1, 2018.
U.S. Advisory Action for U.S. Appl. No. 14/745,329 dated Sep. 21, 2018.
U.S. Final Office Action for U.S. Appl. No. 14/745,330 dated May 18, 2018.
U.S. Advisory Action for U.S. Appl. No. 14/745,330 dated Aug. 27, 2018.
U.S. Non-Final Office Action for U.S. Appl. No. 14/745,330 dated Dec. 10, 2018.
U.S. Final Office Action for U.S. Appl. No. 14/745,330 dated Jul. 29, 2019.
U.S. Advisory Action for U.S. Appl. No. 14/745,330 dated Nov. 5, 2019.
U.S. Notice of Allowance for U.S. Appl. No. 14/745,330 dated Feb. 14, 2020.
U.S. Final Office Action for U.S. Appl. No. 14/745,331 dated Jun. 5, 2018.
U.S. Advisory Action for U.S. Appl. No. 14/745,331 dated Aug. 23, 2018.
U.S. Non-Final Office Action for U.S. Appl. No. 14/745,331 dated Jun. 3, 2019.
U.S. Notice of Allowance for U.S. Appl. No. 14/745,331 dated Sep. 20, 2019.
U.S. Supplemental Notice of Allowability for U.S. Appl. No. 14/745,331 dated Dec. 4, 2019.
U.S. Supplemental Notice of Allowability for U.S. Appl. No. 14/745,331 dated Jan. 9, 2020.
U.S. Final Office Action for U.S. Appl. No. 14/745,334 dated Jun. 1, 2018.
U.S. Advisory Action for U.S. Appl. No. 14/745,334 dated Sep. 21, 2018.
U.S. Final Office Action for U.S. Appl. No. 14/745,337 dated Jun. 1, 2018.
U.S. Advisory Action for U.S. Appl. No. 14/745,337 dated Sep. 21, 2018.
U.S. Non-Final Office Action for U.S. Appl. No. 14/745,337 dated May 13, 2019.
U.S. Final Office Action for U.S. Appl. No. 14/745,337 dated Nov. 29, 2019.
U.S. Notice of Allowance for U.S. Appl. No. 14/745,337 dated Feb. 14, 2020.
U.S. Final Office Action for U.S. Appl. No. 14/745,338 dated Jun. 1, 2018.
U.S. Advisory Action for U.S. Appl. No. 14/745,338 dated Sep. 28, 2018.
U.S. Non-Final Office Action for U.S. Appl. No. 14/745,338 dated Dec. 10, 2018.
U.S. Final Office Action for U.S. Appl. No. 14/745,338 dated Jul. 29, 2019.

(56) References Cited

OTHER PUBLICATIONS

U.S. Advisory Action for U.S. Appl. No. 14/745,338 dated Nov. 5, 2019.
U.S. Notice of Allowance for U.S. Appl. No. 14/745,338 dated Feb. 14, 2020.
U.S. Non-Final Office Action for U.S. Appl. No. 15/289,473 dated Jan. 14, 2019.
U.S. Final Office Action for U.S. Appl. No. 15/289,473 dated Jul. 29, 2019.
U.S. Advisory Action for U.S. Appl. No. 15/289,473 dated Nov. 5, 2019.
U.S. Notice of Allowance for U.S. Appl. No. 15/289,473 dated Feb. 14, 2020.

* cited by examiner

PROPERTY ATTRIBUTES QUESTIONS — 265A
- Does the property have forced air?
- Does the property have an attic?
- Does the property have stucco walls?
- Does the property have crawl space?
- Does the property have one or more fireplaces?
- Does the property have air-conditioning?
- Does the property have carpet?
- How old is the property?
- How many rooms does the property have?
- Did the property have a recent water leak?
- How often does the property have water leaks?

PROXIMITY QUESTIONS — 265B
- How far is the property from the nearest freeway?
- Is the property within proximity of one or more industries or factories?
- Is the property within proximity of one or more restaurants?
- Is the property within proximity of one or more dry cleaners?
- Does the property share walls with one or more other properties (e.g., units) that have pets?

PET QUESTIONS — 265C
- Are there any pets on the property?
- Did any prior occupants of the property have pets?
- How many pets are there on the property?
- What type of pets are on the property?
- Where on the property are the pets allowed?

USER BEHAVIORAL QUESTIONS — 265D
- Do you feel better when you leave the property for a couple of days or even a few hours?
- Do you avoid or no longer use certain rooms in the property?
- Do you use air fresheners?
- Do you cook with gas?
- Do you run bathroom fans after bathing?

FIG. 3

PERSONAL MOTIVATIONS & GOALS QUESTIONS — 265E
- Why are you taking this assessment?
- Are you currently under doctor supervision?
- Are you concerned about yourself or others?
- What do you hope to gain?
- How do you feel right now about indoor air quality and your health?
- Are you looking to make small or drastic changes to the property and indoor air quality?
- How much improvements to indoor air quality do you want to see?
- Do you want to make your property better for yourself, your family or anyone who visits?
- How much time or money are you willing to spend?
- Which of your property's issues would you like to start with?
- How convinced are you that these factors are a problem?
- People like you in properties like this one often take the following actions/interventions with the following results. is this what you are looking to do?

FEEDBACK & ASSESSMENT QUESTIONS — 265L
- Did you do the interventions suggested?
- What happened?
- How much did it cost?
- Has it brought the expected improvements?
- What has improved since you did this action?
- What hasn't changed since you took this action?
- Would you recommend others in a similar situation take this action?

THRESHOLD QUESTIONS — 265G
- How many pets do you have to be exposed to react?
- How quickly does perfume trigger a reaction?
- How long can you stay in a moldy house?

INITIAL SCREENING QUESTIONS — 265F
- Do you feel uneasy when you are behind a diesel bus?
- Are you bothered by the smell of perfume, cologne, air fresheners or scented candles?
- Do you avoid walking down the cleaning products aisle in the grocery store?
- Does running the vacuum cause you to sneeze or make you feel congested?
- Are you allergic to cats or dogs?
- Do you feel uneasy when you enter a musty building or open old books?

SYMPTOMS QUESTIONS — 265I
- Do you have problems with pain in your joints?
- Have you lost motivation to do the things that used to interest you?
- Do you regularly suffer from colds or sinus infections at predictable times of the year?

SENSITIVITY QUESTIONS — 265H
- Do you have allergies to foods?
- Do you have allergic reactions to antibiotics?
- Are you bothered by the smell of cosmetics?
- Are you bothered by the smell of nail polish?
- Are you bothered by the smell of new furniture?
- Are you bothered by the smell of disinfectants?

PERSONAL IMPACT QUESTIONS — 265K
- On a scale from 0 to 10, how much has your life changed because of indoor air quality?
- How much does this impact you?
- How bad is it?

MASKING QUESTIONS — 265J
- How many alcoholic drinks do you consume per week?
- Do you smoke?
- Do you need caffeine everyday?

| PROPERTY ADDRESS | PROPERTY SCORE | PROPERTY MATCH SCORE | COST ESTIMATE OF IMPROVEMENTS | LISTING PRICE |
|---|---|---|---|---|
| 25145 HATTON ROAD | 7 | 23 | $45,000 | $1,029,500 |
| 26411 SCENIC DRIVE | 10 | 15 | $25,000 | $3,295,000 |
| 7SW OCEAN ON MONTE VERDE | 25 | 12 | $13,000 | $2,750,000 |

FIG. 22

ESTIMATING IMPACT OF PROPERTY ON INDIVIDUAL HEALTH—PROPERTY SCORE

CROSS REFERENCE TO RELATED APPLICATIONS

This application is a continuation of U.S. Non-Provisional patent application Ser. No. 15/289,473, filed on Oct. 10, 2016, which in turn claims priority to U.S. Non-Provisional patent application Ser. No. 14/745,329, filed on Jun. 19, 2015, which in turn claims priority to U.S. Provisional Patent Application Ser. No. 62/015,322, filed on Jun. 20, 2014, all incorporated herein by reference.

BACKGROUND

The present invention generally relates to estimating impact of a property on health of an individual, and more particularly, to a system, method and computer program product for correlating health and sensitivities of an individual (e.g., an occupant of the property) with physical design and attributes of a property, local weather and air quality so as to provide the individual an ongoing assessment of degree of health risk the property may have on the health of the individual.

Conventionally, a property is physically inspected to determine the structural integrity of the property. Current inspection protocols, however, do not factor in personal health sensitivities or impacts of a current/prospective owner/occupant of the property and data particular to the building of the property (e.g., building practices, building materials, design of the property, geographical location, ventilation system, etc.) to determine the potential impact the property may have on the health of the owner/occupant. A current/prospective owner/occupant of a property may need to retain the additional services of a qualified property inspector to physically inspect the property and assess potential health-related issues that may arise as a result of occupying the property. The assessment provided by the property inspector, however, may be biased, limited due to lack of sufficient data, and susceptible to human error. Further, retaining the services of the property inspector may be costly.

BRIEF SUMMARY

One embodiment of the invention provides a method for determining a health index of a property area. The method comprises acquiring property data associated with a property area from a data source, and extracting a first property attribute data from the property data acquired. The first property attribute data extracted is used to determine presence or movement of a first pollutant data within the property area. The method further comprises determining a first potential impact data the first pollutant data may have on individual health based in part on the first property attribute data extracted, and computing a property score representing a health index of the property area based in part on the first potential impact data determined.

These and other features, aspects and advantages of the present invention will become understood with reference to the following description, appended claims and accompanying figures.

BRIEF DESCRIPTION OF THE DRAWINGS

The subject matter which is regarded as the invention is particularly pointed out and distinctly claimed in the claims at the conclusion of the specification. The foregoing and other objects, features, and advantages of the invention are apparent from the following detailed description taken in conjunction with the accompanying drawings in which:

FIG. 3 illustrates an example of different question banks 265 maintained by the computing environment 200, in accordance with an embodiment of the invention;

FIG. 4 illustrates another example of different question banks 265 maintained by the computing environment 200, in accordance with an embodiment of the invention;

FIG. 22 illustrates an example investment risk comparison report, in accordance with an embodiment of the invention.

Figure 1:
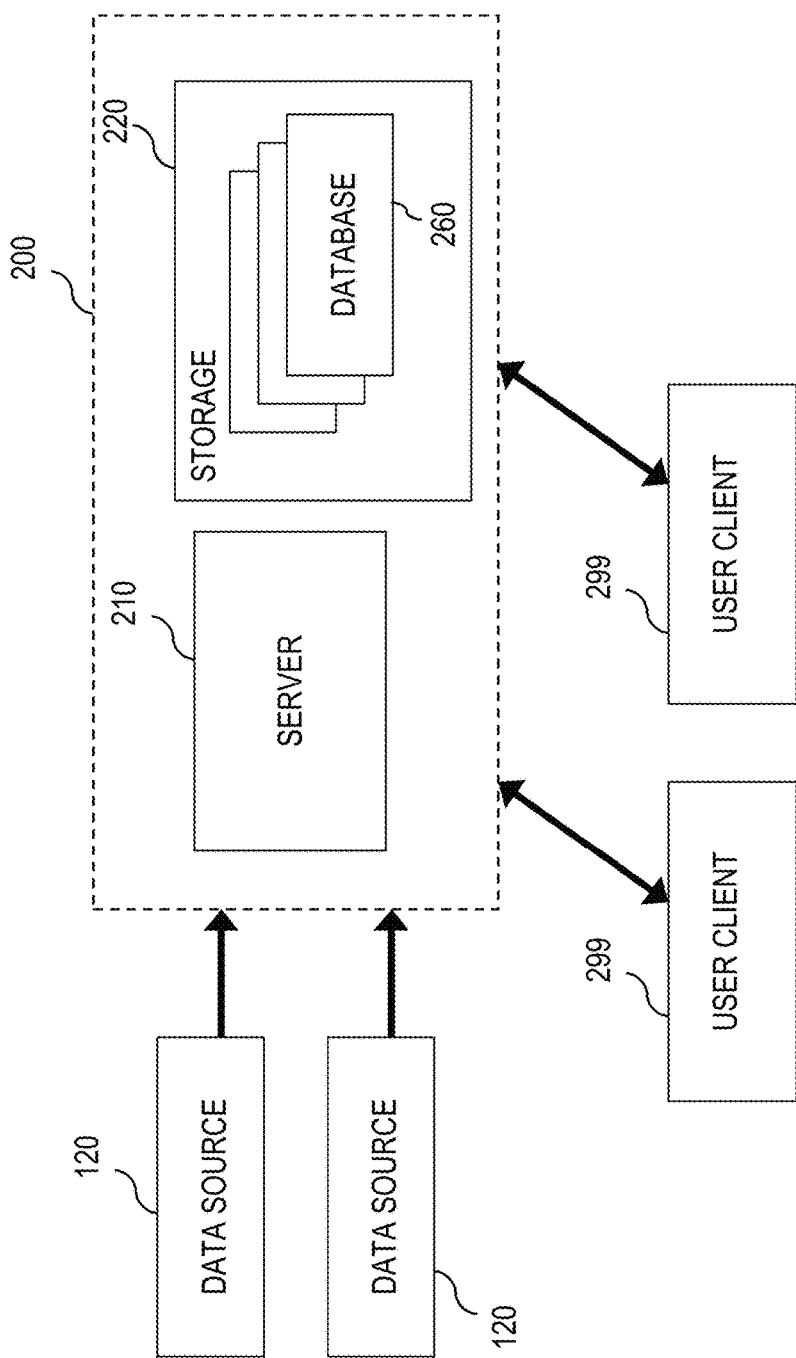
FIG. 1 illustrates an example system 100, in accordance with an embodiment of the invention.

The detailed description explains the preferred embodiments of the invention together with advantages and features, by way of example with reference to the drawings.

DETAILED DESCRIPTION

The present invention generally relates to estimating impact of a property on health of an individual, and more particularly, to a system, method and computer program product for correlating health and sensitivities of an individual (e.g., an occupant of the property) with physical design and attributes of a property, local weather and air quality so as to provide the individual an ongoing assessment of degree of health risk the property may have on the health of the individual.

One embodiment of the invention provides a method for determining a health index of a property area. The method comprises acquiring property data associated with a property area from a data source, and extracting a first property attribute data from the property data acquired. The first property attribute data extracted is used to determine presence or movement of a first pollutant data within the property area. The method further comprises determining a first potential impact data the first pollutant data may have on individual health based in part on the first property attribute data extracted, and computing a property score representing a health index of the property area based in part on the first potential impact data determined.

In this specification, the terms "property" and "property area" are generally used to reference all synonyms of different types of spaces, areas and dwellings intended for occupancy, whether commercial or residential, single or multi-family, individual structures or tract developments governed by homeowners association (HOA) covenance, currently existing, under construction or proposed. Examples of properties/property areas may include, but are not limited to, the following: a house, a dwelling, a mobile home, a set of houses, a housing development, a suburb, a town, a city, a state, a country, an apartment building composed of multiple units, an estate, housing stock, a set of houses within an enclosed geographic area, a set of houses that are separated by significant space, a city block, a building, a property approved for inhabitation, a set of houses that share a common characteristic, such as a peaked roof, a site of a future house, sites of future houses, a construction site for a house or multiple houses, track houses, custom homes, all houses within a given region, a houseboat, a physical space that currently contains one or more houses, covenance controlled groupings or developments (e.g., groupings or developments governed by HOA covenance), and housing stock owned, controlled and/or managed by a government, a property management group, a developer or a builder. The terms "property" and "property area" are used interchangeably in this specification.

In this specification, the term "user" is generally used to reference an individual or an entity. Examples of users include, but are not limited to, the following: may be a current owner of a property, a prospective owner of a property, an occupant of a property (e.g., a tenant), an individual who is present on a property for work/educational purposes (e.g., an employee of a business operating on a property, a student of a school operating on a property), a patron of a business operating on a property (e.g., a hotel guest, a restaurant guest), etc. The terms "individual" and "user" are used interchangeably in this specification.

In this specification, the term "pollutants" is generally used to reference materials that may negatively impact/harm an environment and health of an individual. Pollutants may originate in an indoor environment or an outdoor environment. There may be different types of pollutants, such as chemical pollutants, biological pollutants, and toxic pollutants. Examples of different chemical pollutants, biological pollutants and toxic pollutants may include, but are not limited to, the following: pathogens (e.g., infectious agents such as bacteria, virus, fungi, etc.), irritants (e.g., chemicals that are not corrosive to human tissue and whose effects are reversible), poison (e.g., substances with an inherent property that may destroy human life or impair human health), toxin (e.g., a poison produced by an organism), allergens, gases, chemicals, pollen, jet fuel, freeway emissions, dust mites, dust mite by products, dampness, molds, mycotoxins, chemicals, bacteria, yeast, micro biome imbalances, excess particulate, ozone imbalances, Volatile Organic Compounds, Microbial Volatile Organic Compounds, Semi-volatile Organic Compounds, lead paint, asbestos, microfibers, etc.

In this specification, the term "indoor air" is generally used to reference interior air of a property that is inhalable or in contact with skin of an individual.

In this specification, the term "indoor air quality" is generally used to reference total presence and interaction of components of indoor air. Examples of components that may impact indoor air quality may include, but are not limited to, the following: indoor pollution, fresh air supply, temperature, and humidity that influences a human body's ability to establish and maintain homeostasis.

In this specification, the term "homeostasis" is generally used to reference ability or tendency of an individual to maintain internal stability and functioning to compensate for environmental changes. An example of homeostasis is a human body maintaining an average temperature of 98.6 degrees F. in extreme heat or cold. Another example of homeostasis is a human body rebalancing functioning when exposed to pollutants.

In this specification, the term "health" is generally used to reference comparative effects and ability to function resulting from a human body's ability to establish and maintain homeostasis within extremes of illness and thriving.

In this specification, the terms "illness" and "disease" are generally used to reference when a human body fails to achieve a reasonably functional state of homeostasis.

In this specification, the term "individual health and sensitivities" is generally used to reference specific attributes experienced by an individual, such as individual susceptibilities and impacts to different potential illness and disease outcomes that may affect the health of the individual.

In this specification, the terms "health risk" and "risk assessment of health" are generally used to reference estimated/predicted negative impact on health of an individual.

In this specification, the term "health index" is generally used to reference an assessment of degree of health risk on health of the individual.

Embodiments of the invention correlate symptomology and sensitivities of a user with physical design and attributes of a property, local weather and air quality so as to provide the user an ongoing assessment of degree of health risk the property may have on the health of the user. Embodiments of the invention allow for expression of the idea that presence and/or combination of physical design and attributes of a property is analogous to DNA. Further, physical design and attributes of a property when combined with environmental context information relating to the property (e.g., local weather and air quality) may be used to provide an ongoing assessment of degree of health risk the property may have on the health of the user.

Embodiments of the invention provide a comparatively low-cost solution for objectively and digitally determining potential impact a property may have on health of an individual (e.g., current/prospective occupant of the property).

In this specification, the term "property attributes" is generally used to reference different physical and geographical characteristics of a property (e.g., physical design and attributes, local weather, air quality, etc.).

Embodiments of the invention correlate different property attributes with different individual susceptibilities and impacts to different potential illness and disease outcomes that may affect the health of an individual.

FIG. 1 illustrates an example system 100, in accordance with an embodiment of the invention. The system 100 comprises a centralized computing environment 200 including one or more server devices 210, and one or more storage devices 220. The storage devices 220 may maintain one or more databases 260. One or more applications 410 (FIG. 2) may execute/operate on the server devices 210 to provide one or more online, virtual tools relating to a property area.

A user may access an online, virtual tool provided by the computing environment 200 using an electronic user client device 299, such as a personal computer, or a mobile device (e.g., a laptop computer, a tablet, a mobile phone, etc.). In one embodiment, each user client device 299 exchanges data with the computing environment 200 over a connection (e.g., a wireless connection, a wired connection, or a combination of the two).

As described in detail later herein, the computing environment 200 is configured to acquire property data for a property from one or more data sources, such as third-party data sources 120 or a user. Property data for a property may include, but is not limited to, the following: climate data about environment around the property, public data about the property and its construction (e.g., age of property, average precipitation in the environment around the property, whether the property is located in an urban area, last major construction of the property, age of roof of the property), image data 110 (FIG. 2) for the property, and user input 111 (e.g., user responses to questions relating to the property, user feedback).

Figure 2:
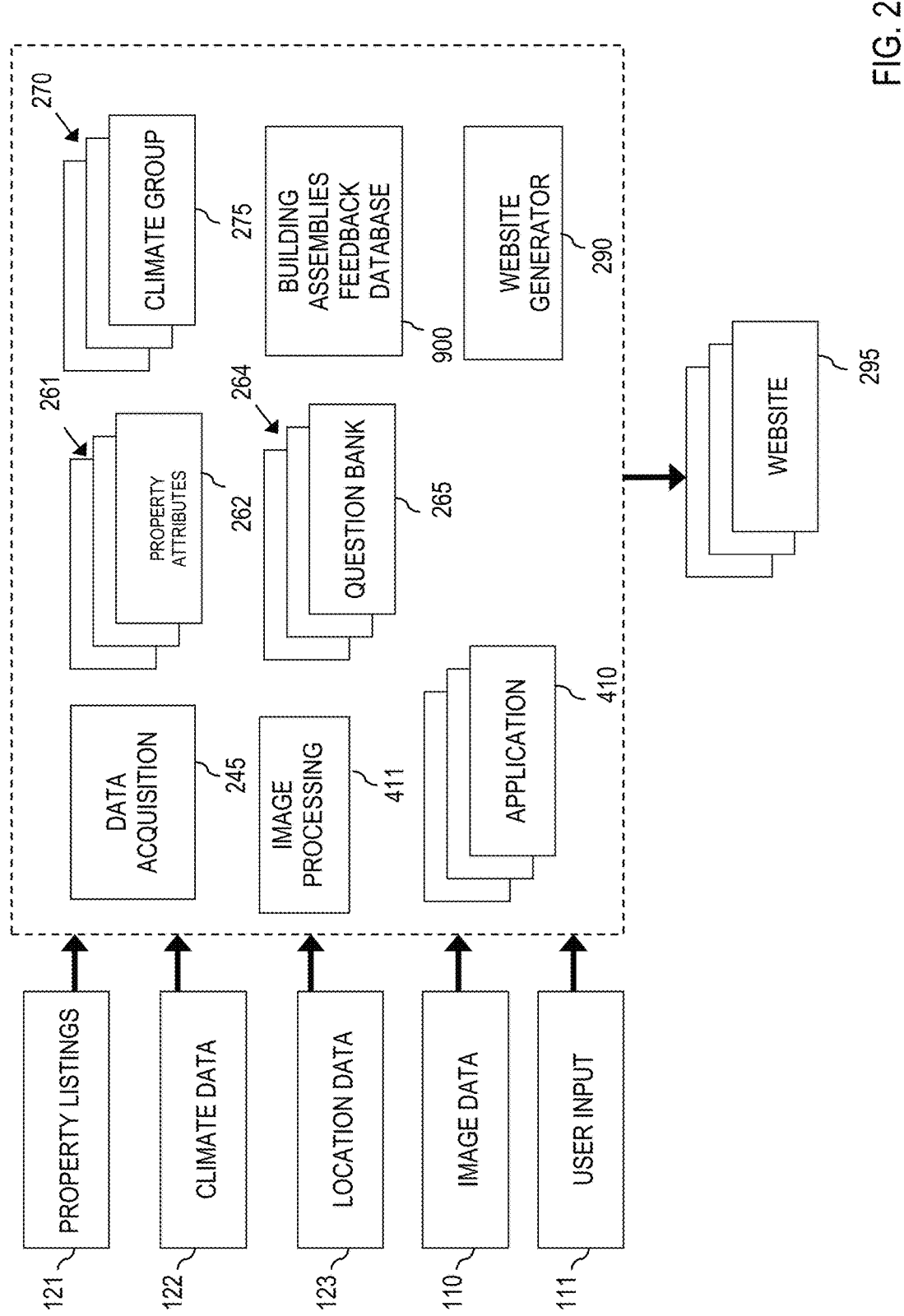
FIG. 2 illustrates the centralized computing environment 200 in detail, in accordance with an embodiment of the invention.

FIG. 2 illustrates the centralized computing environment 200 in detail, in accordance with an embodiment of the invention. The centralized computing environment further comprises a data acquisition unit 245 configured to acquire property data for a property from different types of third-party data sources 120 (FIG. 1), such as a property listings data source 121 (e.g., a property listing database (MLS, Redfin, Zillow), a climate data source 122 providing climate data about environment around the property (e.g., climate data from American Society of Heating, Refrigerating, and Air-Conditioning Engineers (ASHRAE), climate zone maps from Department of Energy (DOE), etc.), and a location data source 123. Other types of third-party data sources 120 may include data sources providing data about the property and its construction, geophysical data, proximity data, proxy data, contractor data, disclosure data, and model data for modeling/projecting factors used by one or more applications 410 executing/operating on the server devices 210. Property data for a property may include raw actual data and/or statistical data.

In one embodiment, the data acquisition unit 245 is configured to interface with web service interfaces of third-party data sources 120 (e.g., Google Maps via Google Maps API, Bing and other similar web services) to acquire/download data from the third-party data sources 120.

In one embodiment, the storage devices 220 (FIG. 1) maintains at least one database 260 including a collection 261 of datasets 262 of property attributes for different property addresses located across different geographical locations (e.g., nationwide). As described in detail later herein, the computing environment 200 is configured to acquire property data for different properties located across different geographical locations (e.g., nationwide) from multiple data sources, such as third-party data sources 120. Relevant data used in determining property attributes may be extracted from the property data acquired. Any relevant data extracted may be processed and/or transformed for determining property attributes, and may be maintained in the storage devices 220, in compliance with third party agreements, if any.

In one embodiment, the data acquisition unit 245 is configured to determine property attributes based on property data acquired from one or more data sources, such as third-party data sources 120 or a user. For example, for a particular property, the data acquisition unit 245 may acquire raw actual data associated with the property from one or more third-party data sources 120. The data acquisition unit 245 may also acquire statistical data associated with the property and/or geographical location of the property from one or more third-party data sources 120. The data acquisition unit 245 may also acquire other types of data associated with the property from other types of data sources. The data acquisition unit 245 may extract disparate heterogeneous property attributes from the raw actual data and/or the statistical data acquired, and maintain a dataset 262 of property attributes for the property in at least one database 260.

In one embodiment, a dataset 262 of property attributes for a property may include the following physical and geographical characteristics: a corresponding property address (i.e., physical address), corresponding latitude and longitude of the property, age of the property, climate data from its nearest point source (e.g., temperature ranges, precipitation data, and relative humidity data from climate data corresponding to a city in which the property is located), number of bedrooms, internal wall type, external wall type, air conditioning/cooling type, heating type, roof type, basement type, floor type covering, pollen data, etc.

In one embodiment, the computing environment 200 further comprises an image processing unit 411 configured to process image data 110 acquired by the data acquisition unit 245 from a third-party data source 120 (e.g., Google Maps, Redfin, Zillow or other similar web services) or a user (e.g., images/photos uploaded by a user and captured via an image capture device). The image processing unit 411 may comprise a machine learning classifier that is trained to recognize specific property attributes for a property based on image data 110 for the property. Image data 110 for a property may include one or more images and/or one or more videos capturing one or more areas of the property and/or environment around the property.

In one embodiment, the image processing unit 411 may utilize specialized detection techniques on image data 110 for a property for determining presence of a peaked roof on the property, presence of a basement on the property, external wall type of the property, and volume of the property.

In one embodiment, the image processing unit 411 may utilize specialized detection techniques on image data 110 for a property for evaluating topography to determine if water flows away from or towards the property.

In one embodiment, the image processing unit 411 computes an approximate volume of a property based on a plan map view and a street map view included in image data 110 for the property. The image processing unit 411 may utilize specialized detection techniques on the image data 110 for determining a length, a width and a height of the property. The image data analysis/processing unit 411 then computes the approximate volume of the property as the product of the length, the width and the height of the property.

In one embodiment, the computing environment 200 maintains a collection 270 of different climate groups 275. A climate group 275 may represent a particular climate zone (e.g., hot-humid, hot-dry, cold, frigid, moderate, mixed, etc.). As described in detail later herein, a property address associated with a property may be classified in a particular climate group 275 of the collection 270 based on property attributes for the property.

In one embodiment, utilizing the data acquisition unit 245 and the image processing unit 411, the computing environment 200 is configured to acquire property data, determine property attributes based on the property data, and correlate the property attributes on a per property address basis nationwide. For example, the computing environment 200 may operate in accordance with Steps 1-15 provided below:

Step 1: For each city, for each street (in alphabetical order), extract a property address in numerical sequence.

Step 2: Using the property address, acquire raw actual data for a property associated with the property address from a third party data source 120, such as a property listings database 121. Determine property attributes based on the raw actual data acquired. The property attributes determined may include latitude and longitude of the property, age of the property, number of bedrooms within the property, internal wall type of the property, air conditioning/cooling type of the property, heating type of the property, and floor covering type of the property.

Step 3: If raw actual data for the property is not available from a third party data source 120, determine property attributes for the property based on statistical data acquired from a third party data source 120.

Step 4: Acquire a plan map view of the property from a third-party data source 120 (e.g., Google Maps, Redfin, Zillow or other similar web services).

Step 5: Determine a length and a width of the property based on the plan map view.

Step 6: Acquire a street map view of the property from a third-party data source 120 (e.g., Google Maps, Redfin, Zillow or other similar web services).

Step 7: Identify the property in the street view using specialized detection techniques.

Step 8: Determine a height of the property using specialized detection techniques.

Step 9: Compute an approximate volume of the property based on the length, the width and the height of the property.

Step 10: Use specialized detection techniques to determine whether the property has a peaked roof or a flat roof.

Step 11: Use specialized detection techniques to determine whether the property has a basement. In the event that the specialized detection techniques used are unsuccessful, use brute force pixel sequence evaluation to detect pattern variations.

Step 12: Use specialized detection techniques to determine external wall type of the property. In the event that the specialized detection techniques are unsuccessful, use brute force pixel sequence evaluation to detect pattern variations.

Step 13: Acquire climate data for a geographical location/area in which the property address is located from a third-party data source 120 (e.g., a climate data source 122). Extract temperature ranges, precipitation data, and relative humidity data from the climate data.

Step 14: Determine which climate group 275 the property address should be classified in based on the temperature ranges, the precipitation data, and the relative humidity data.

Step 15: Store all the different property attributes computed/determined for the property address in the database 260.

In one embodiment, a property attribute maintained in the database 260 may be assigned a default value or a range of default values if data specific to that property attribute is unavailable.

As stated above, one or more applications 410 may execute/operate on the server devices 210 (FIG. 1) to provide one or more online, virtual tools relating a property area. In one embodiment, the computing environment 200 further comprises a website generator 290 configured to generate one or more web sites 295 for the online, virtual tools. A user may access a website 295 via a user client device 299.

In one embodiment, the computing environment 200 further comprises a collection 264 of different question banks 265. Each question bank 265 maintains a specific set of questions for obtaining, from a user, additional data that is not available from a third-party data source 120. As described in detail later herein, an application 410 may select which questions from the questions banks 265 to query a user with. The selected questions may be presented/displayed to the user on a website 295. All user input 111 entered by the user via the website 295 in response to the questions presented may be collected and maintained in at least one database 260. As described in detail later herein, one or more applications 410 operating on the server devices 210 may analyze user input 111 for purposes of customization or refinement.

In one embodiment, the computing environment 200 may receive different user inputs 111 comprising different user feedback relating to use of different building materials and/or different building assemblies in construction projects for different property areas. A user (e.g., a builder, a developer, an architect, etc.) may enter user feedback via a website 295. User feedback may indicate success or failure of using particular building materials and/or particular building assemblies in particular property areas. All user feedback is collected and maintained in a building assemblies feedback database 900. The database 900 represents a vast data source on different building materials and/or different building assemblies. As described in detail later herein, one or more applications 410 operating on the server devices 210 may use the database 900 in determining which building materials and/or building assemblies are unsuitable for specific climates that are susceptible to moisture and/or pollutant accumulation. As another example, one or more applications 410 operating on the server devices 210 may also use the database 900 in determining which building materials and/or building assemblies are suitable for specific climates that are susceptible to moisture and/or pollutant accumulation.

FIG. 3 illustrates an example of different question banks 265 maintained by the computing environment 200, in accordance with an embodiment of the invention. The question banks 265 may include, but are not limited to, the following: a question bank 265A comprising one or more questions inquiring about property attributes of a property ("property attributes questions"; see examples of property attributes questions shown in FIG. 3), a question bank 265B comprising one or more questions inquiring about surroundings around a property ("proximity questions"; see examples of proximity questions shown in FIG. 3), a question bank 265C comprising one or more questions inquiring about pets located at a property ("pet questions"; see examples of pet questions shown in FIG. 3), and a question bank 265D comprising one or more questions inquiring about particular user behaviors specific to a property ("user behavioral questions"; see examples of user behavioral questions shown in FIG. 3).

FIG. 4 illustrates another example of different question banks 265 maintained by the computing environment 200, in accordance with an embodiment of the invention. The question banks 265 may include, but are not limited to, the following: a question bank 265E comprising one or more questions for querying a user about his/her personal motivations and goals ("personal motivations and goals questions"; see examples of personal motivations and goals questions shown in FIG. 4), a question bank 265F comprising one or more questions for querying a user about his/her general sensitivities to certain triggers ("initial screening questions"; see examples of initial screening questions shown in FIG. 4), a question bank 265G comprising one or more threshold questions for querying a user about his/her threshold limits with regards to exposure to certain triggers ("threshold questions"; see examples of threshold questions shown in FIG. 4), a question bank 265H comprising one or more questions for querying a user about his/her sensitivities to certain triggers ("sensitivity questions"; see examples of sensitivity questions shown in FIG. 4), a question bank 265I comprising one or more questions for querying a user about symptoms experienced by the user ("symptoms questions"; see examples of symptoms questions shown in FIG. 4), a question bank 265J comprising one or more questions for querying a user about potential masking effects (i.e., impact lifestyle and previous exposures the user has experienced) ("masking questions"; see examples of masking questions shown in FIG. 4), a question bank 265K comprising one or more questions for querying a user about impact a property has had on the user ("personal impact questions"; see examples of personal impact questions shown in FIG. 4), and a question bank 265L comprising one or more questions for querying user feedback and assessment with respect to any recommendations generated by the computing environment 200 ("feedback and assessment questions"; see examples of feedback and assessment questions shown in FIG. 4).

In one embodiment, some questions maintained in one question bank 265 may overlap with some questions maintained in another question bank 265.

A response to a question may be provided in different manners. For example, in response to a question requiring a "yes" or "no" answer, a user may respond to the question by indicating either "yes" or "no". As another example, in response to a question requiring a user to select one or more checkboxes representing suggested answers, a user may respond to the question by selecting one or more of the checkboxes. As another example, in response to a question where the answer may fall within a range of values, a user may respond to the question by positioning a slider along a sliding scale to a particular value in the range. As another example, a user may respond to a question by entering free form text (e.g., entering text in an input comment box).

Property Score Application

In this specification, the term "property score" represents a health index for the property, its immediate environments, and physical and geographical characteristics associated with the property. A property score for a property may be used to predict presence of factors (e.g., presence of bacteria, virus, mold, pollen, dust mites, pet dander, chemicals and other pollutants) at the property that may contribute to illnesses and diseases, and that may negatively impact health of an individual. A property score may be represented using a number grade, a percentage grade, a letter grade, etc. In one embodiment, the property score may be a numerical grade that ranges anywhere between a minimum of 1 and a maximum of 100.

Figure 5:
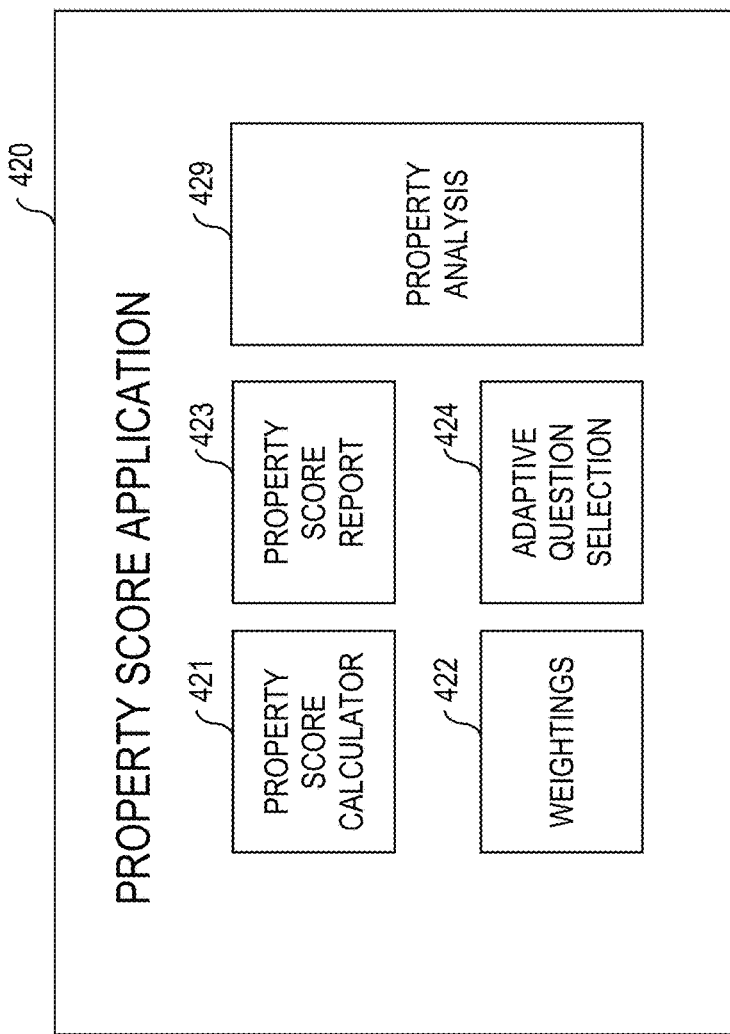
FIG. 5 illustrates an example property score application 420, in accordance with an embodiment of the invention.

FIG. 5 illustrates an example property score application 420, in accordance with an embodiment of the invention. In one embodiment, one of the applications 410 (FIG. 2) executing/operating on the server devices 210 (FIG. 1) is a property score application 420. The property score application 420 comprises a property score calculator unit 421 configured to determine a property score for a property based on property attributes for the property. The property score may be stored in the database 260 together with a dataset 262 including the property attributes for the property.

In one embodiment, a property score for a property may represent ability for pollutants to develop and move within the property. For each possible type of pollutant, the property score calculator unit 421 is configured to identify certain physical and/or geographical characteristics of the property that may increase or decrease presence and/or movement of the pollutant. The property score calculator unit 421 utilizes an algorithm to determine potential impact (i.e., severity) a combination of pollutants may have upon health of an individual.

The property score calculator unit 421 is configured to analyze input data acquired from different data sources such as, but not limited to, public data from third-party data sources 120, data from crowdsourcing, user input from users, sensor data from property sensors, and internal databases. As described in detail later herein, based on input data, the property score calculator unit 421 computes initial, dynamically inter-related factors/indexes used in determining a property score.

In one embodiment, the property score application 420 comprises a property score report unit 423 for generating a property score report that includes a property score for a property. A property score report including a property score for a property provides an indication of when an imbalance in the property exists. The property score report may also include one or more recommendations, such as remediation actions and/or interventions for a user (e.g., occupant of the property) to take to improve the property score. Information contained in the various factors/indexes contributing to the property score can provide guidance as to what actions and/or interventions are most appropriate. A new property score for the property may be determined after the user performs the remediation actions and/or improvements recommended to provide verification of effective and sufficient improvement.

A property score report may be presented to a user via a web site 295.

The property score report may also suggest one or more remediation actions and/or interventions for a user to take.

In this specification, the term "prevalence" is used to denote frequency of a particular attribute, factor or index. For example, if the prevalence of refrigeration-type air conditioners is ten times more than the prevalence of evaporative-type air coolers, the influence of evaporative-type air coolers on a property score will be less than the influence of refrigeration-type air conditioners on the property score.

In this specification, the term "weighting" is used to denote a comparative contribution of a particular attribute, factor or index. For example, if the impact of evaporative-type air coolers, when present, on an indoor environment is ten times more than the impact of refrigeration-type air conditioners, the influence of evaporative-type air coolers on a property score will be more than the influence of refrigeration-type air conditioners on the property score.

In one embodiment, the property score application 420 comprises a weightings unit 422. The weightings units 422 comprises, but is not limited to, the following: (a) different weighting values for different attributes, factors or indexes, (b) different prevalence values for different attributes, factors or indexes, and (c) data representing interrelationships between different attributes, factors or indexes. For example, a property attribute may have a corresponding weighting value and a corresponding prevalence value, wherein the combination of the weighting value and the prevalence value represents how much the property attribute is likely to influence a property score for a property.

In one embodiment, a weighting value and/or a prevalence value may be pre-defined or determined based on data correlations. The data correlations may be learned through application of a machine learning algorithm, survey data and/or analysis of experts/professionals. The data correlations may be determined based on different data sets, such as property attributes for the property, factors/indexes used in determining the property score for the property, personal profiles, health insurance recommendations, health records, virtual inspections of the property, personal action plans, expert judgment, survey results, user responses to questions, user actions, user feedback indicating results of performing recommended remediation actions and/or interventions, etc. These different datasets may also be used to refine/adjust one or more of the weighting values and/or a prevalence values maintained.

An amplification factor for a particular attribute/factor/index represents a combination of prevalence and weighting for the particular attribute/factor/index. Amplification factors are determined based on combinations of data correlations determined from machine learning algorithms, large dataset surveys, and expert judgment. An amplification factor for a particular attribute/factor/index modifies the particular attribute/factor/index to more accurately reflect a true influence of the particular attribute/factor/index on a property score, thereby improving accuracy and utility of the property score. For example, if the prevalence of refrigeration-type air conditioners is ten times more than the prevalence of evaporative-type air coolers, but the impact of evaporative-type air coolers, when present, on indoor environment is ten times more than the impact of refrigeration-type air conditioners, evaporative-type air coolers have low prevalence and high weighting values. As such, the influence of evaporative-type air coolers on a property score will only be significant if evaporative-type air coolers are present.

In one embodiment, the property score application 420 may acquire property data for a property from a user by presenting one or more questions via a website 295. Specifically, the property score application 420 comprises an adaptive question selection unit 424 for adaptively selecting questions from the collection 264 based on property data for a property (e.g., climate data about the environment around the property, public data about the property and its construction, and user input, if any). If, at any point during the presentation of the selected questions, user responses seem contradictory or mis-entered, the adaptive question selection unit 424 runs a related education module and then repeats or rephrases the selected questions. Questions selected and presented to a user are dynamically selected based on prior user interactions (e.g., prior user responses). Even if user input is not available, the property score calculator unit 421 may still determine a property score for the property based on property data acquired from other data sources, such as a third-party data source 120.

In one embodiment, a property score for a property maintained in the database 260 is updated when updated/additional property attributes for the property are determined. For example, property attributes maintained in the database 260 may be refreshed on a cyclic basis to ensure that the most current property attributes are available when determining a property score. The frequency/cycle at which a particular property attribute within the database 260 is refreshed is based on the nature of the property attribute. For example, climate-related property attributes may be refreshed annually, whereas property attributes representing physical characteristics may be refreshed every five years. In the instance where a particular property attribute used in calculating a factor/index corresponding to a pollutant is generated by a third-party data source 120, the property attribute will be updated upon notification from the third-party data source 120 of significant changes to the attribute. The refresh of property attributes will utilize the same methods of data acquisition as performed by the data acquisition unit 245. When property attributes for a property are refreshed, a new property score for the property is determined and stored in the database 260.

In one embodiment, the property score application 420 extracts/determines a property attribute data (e.g., pattern relating to a property attribute) from property data associated with a property area. The property score application 420 combines the property attribute data with at least one other property attribute data to determine presence or movement of a pollutant data (e.g., pattern relating to a pollutant) within the property area. The property score application 420 determines a potential impact data (e.g., pattern relating to personal impact) that the pollutant data may have on individual health based in part on the combination, and computes a property score representing a health index of the property area based in part on the potential impact data.

In one embodiment, the property score calculator unit 421 determines a property score for a property based on the following factors/indexes: a home structural attributes index for the property, an indoor chemical index for the property, an indoor particle index for the property, an indoor pet index for the property, an indoor dampness index for the property, an indoor cavity index for the property, an outdoor pollutant index for the property, an outdoor environmental index for the property, an air movement index for the property, an indoor biological activity index for the property, an indoor mold index for the property, and amplification factors for the indexes.

In this specification, the term "total burden" represents a weighted calculation of total exposure an individual can be exposed to before moving to a higher level of sensitivity. This is largely determined by the individual's overall sensitivity levels. Sensitivity levels, when appearing in certain combination, are correlated to significantly lower thresholds and higher impacts for various specific trigger items. When a burden that an individual is exposed to is too high, the individual's overall sensitivities rise. The property score application 420 adjusts by lowering thresholds and raising impact scores accordingly based on data and prior data correlations determined.

For example, if property attributes for a property and/or user responses to questions indicate presence data points relating to an indoor pet index, a property score for the property will be nominally impacted by the indoor pet index. However, if the property attributes and/or the user responses also indicate simultaneous presence of data points relating to a significant/high outdoor pollutant index, indoor chemical index, biological activity index, and air movement index, this combination of indexes may substantially enhance the impact of the indoor pet index on the property score, as well as severity of the outdoor pollutant index, indoor chemical index, indoor biological activity index and air movement index on the property score.

The higher a total burden, the more frequently and the more strongly an individual will react to particular triggers of the property that impacts the individual. A property score report generated for a property may suggest one or more remediation actions and/or interventions for reducing a total burden to reduce any impact the property may have on an individual.

In one embodiment, there may be different total burdens for different factors/indexes. A total burden for a particular factor/index may be used to amplify the factor/index, where necessary.

As described in detail later herein, a factor/index may contribute as an amplification factor for another factor/index.

In one embodiment, for each factor/index, the property score calculator unit 421 determines a projected accuracy rating based on number of data points used in computing the factor/index and amplification factors for the factor/index.

Table 1 provided below comprises a listing identifying different parameters referenced in this specification.

TABLE 1

| Abbreviation | Definition |
| --- | --- |
| Property_Score | Property score for a property |
| IMI | Indoor mold index (IMI) |
| IMI_Raw | Raw IMI |
| IMI_Amplification | Amplification factors for IMI |
| IMI_TotalBurden | Total burden for IMI |
| OPI | Outdoor pollutant index (OPI) |
| OPI_Raw | Raw OPI |
| OPI_Amplification | Amplification factors for OPI |
| OPI_TotalBurden | Total burden for OPI |
| ICI | Indoor chemical index (ICI) |
| ICI_Raw | Raw ICI |
| ICI_Amplification | Amplification factors for ICI |
| ICI_TotalBurden | Total burden for ICI |
| IBAI | Indoor biological activity index (IBAI) |
| IBAI_Raw | Raw IBAI |
| IBAI_Amplification | Amplification factors for IBAI |
| IBAI_TotalBurden | Total burden for IBAI |
| IPETI | Indoor pet index (IPETI) |
| IPETI_Raw | Raw IPETI |
| IPETI_Amplification | Amplification factors for IPETI |
| IPETI_TotalBurden | Total burden for IPETI |
| HSAI | Home structural attributes index (HSAI) |
| HSAI_Raw | Raw HSAI |
| HSAI_Amplification | Amplification factors for HSAI |
| HSAI_TotalBurden | Total burden for HSAI |
| IPI | Indoor particle index (IPI) |
| IPI_Raw | Raw IPI |
| IPI_Amplification | Amplification factors for IPI |
| IPI_TotalBurden | Total burden for IPI |
| IDI | Indoor dampness index (IDI) |
| IDI_Raw | Raw IDI |
| IDI_Amplification | Amplification factors for IDI |

TABLE 1-continued

| Abbreviation | Definition |
| --- | --- |
| IDI_TotalBurden | Total burden for IDI |
| ICAVI | Indoor cavity index (ICAVI) |
| ICAVI_Raw | Raw ICAVI |
| ICAVI_Amplification | Amplification factors for ICAVI |
| ICAVI_TotalBurden | Total burden for ICAVI |
| OEI | Outdoor environmental index (OEI) |
| OEI_Raw | Raw OEI |
| OEI_Amplification | Amplification factors for OEI |
| OEI_TotalBurden | Total burden for OEI |
| AMI | Air movement index (AMI) |
| AMI_Raw | Raw AMI |
| AMI_Amplification | Amplification factors for AMI |
| AMI_TotalBurden | Total burden for AMI |

In one embodiment, the property score calculator unit 421 computes a property score for a property in accordance with the equation (1) provided below:

$$\text{Property\_Score} = \text{HSAI} + \text{ICI} + \text{IPI} + \text{IPETI} + \text{IDI} + \text{ICAVI} + \text{OPI} + \text{OEI} + \text{AMI} + \text{IBAI} + \text{IMI} \quad (1).$$

Indoor Mold Index

In one embodiment, the property score calculator unit 421 determines an indoor mold index for a property by analyzing property data for the property (e.g., a dataset 262 comprising property attributes for the property, user responses to questions relating to the property, etc.) to identify data points that indicate potential mold presence in the property. Examples of data points that indicate potential mold presence in the property may include, but are not limited to, the following: (a) water-related events, such as recent events affecting the property (e.g., leaks or floods), high dampness, and high number of wet dry cycles per year in geographical area of the property, and (b) conditions signaling poor maintenance of the property, such as old roofing, broken downspouts, unkempt gutters, and old ducting. Examples of data points that indicate potential amplifications factors for the indoor mold index for the property may include, but are not limited to, the following: high dampness, high number of wet dry cycles per year in geographical area of the property, and presence of numerous cavities in the property.

In one embodiment, the property score calculator unit 421 computes an indoor mold index (IMI) for a property in accordance with equation (2) provided below:

$$\text{IMI} = \text{IMI\_Raw} \times \text{IMI\_Amplification} \times \text{IMI\_TotalBurden} \quad (2).$$

In one embodiment, the property score calculator unit 421 computes IMI_Raw based on weighted user responses to questions selected from the collection 264 to identify data points related to an indoor mold index. The property score calculator unit 421 computes IMI_Amplification based on weighted user responses to questions selected from the collection 264 to identify data points related to amplifications factors for an indoor mold index. The property score calculator unit 421 computes the product of IMI_Raw, IMI_Amplification and IMI_TotalBurden to obtain IMI.

Indoor Pet Index

In one embodiment, the property score calculator unit 421 determines an indoor pet index for a property by analyzing property data for the property (e.g., a dataset 262 comprising property attributes for the property, user responses to questions relating to the property, etc.) to identify data points that indicate potential pet presence at the property. Examples of data points that indicate potential pet presence at the property may include, but are not limited to, the following: user responses to pet questions selected from the question bank 265C (FIG. 3). Examples of data points that indicate potential amplifications factors for the indoor pet index for the property may include, but are not limited to, the following: vacuum usage behaviors, forced air, hard to clean places, carpeting, and duct age.

In one embodiment, the property score calculator unit 421 computes an indoor pet index (IPETI) for a property in accordance with equation (3) provided below:

$$IPETI = IPETI\_Raw \times IPETI\_Amplification \times IPETI\_TotalBurden \quad (3).$$

In one embodiment, the property score calculator unit 421 computes IPETI_Raw based on weighted user responses to questions selected from the collection 264 (e.g., pet questions from the question bank 265C) to identify data points related to an indoor pet index. The property score calculator unit 421 computes IPETI_Amplification based on weighted user responses to questions selected from the collection 264 to identify data points related to amplifications factors for an indoor pet index. The property score calculator unit 421 computes the product of IPETI_Raw, IPETI_Amplification and IPETI_TotalBurden to obtain IPETI.

Outdoor Pollutant Index

An outdoor pollutant index for a property represents a combination of various possible sources, locations, and types of outdoor pollutants, irrespective of other indexes. In one embodiment, the property score calculator unit 421 determines an outdoor pollutant index for a property by analyzing property data for the property (e.g., a dataset 262 comprising property attributes for the property, user responses to questions relating to the property, etc.) to identify data points that indicate potential outdoor pollutant sources, locations, and types in close proximity to the property. Examples of data points that indicate potential outdoor pollutant sources, locations, and types in close proximity to the property may include, but are not limited to, the following: (a) industrial plants, (b) airports, (c) heavy traffic including freeways and highways, (d) types of traffic such as buses, trains, trucks, aircraft, (e) parking lots for malls, schools, auditoriums, stadiums, (f) business that exhaust pollutants such as dry cleaners, print shops, restaurants, (g) agriculture using fertilizers and pesticides, and (h) livestock ranching or feed lots. Examples of data points that indicate potential amplifications factors for the outdoor pollutant index for the property may include, but are not limited to, the following: heavy truck and bus traffic, industrial pollution, and agricultural activities.

In one embodiment, the property score calculator unit 421 computes an outdoor pollutant index (OPI) for a property in accordance with equation (4) provided below:

$$OPI = OPI\_Raw \times OPI\_Amplification \times OPI\_TotalBurden \quad (4).$$

In one embodiment, the property score calculator unit 421 computes OPI_Raw based on weighted user responses to questions selected from the collection 264 (e.g., proximity questions from the question bank 265B) to identify data points related to an outdoor pollutant index. The property score calculator unit 421 computes OPI_Amplification based on weighted user responses to questions selected from the collection 264 to identify data points related to amplifications factors for an outdoor pollutant index. The property score calculator unit 421 computes the product of OPCF_Raw, OPI_Amplification and OPI_TotalBurden to obtain OPI.

In one embodiment, OPI_Amplification is applied to obtain OPI only when three or more amplification factors are present.

Indoor Chemical Index

An indoor chemical index for a property represents a combination of various possible sources of potential chemicals in an indoor environment of the property, irrespective of other indexes. In one embodiment, the property score calculator unit 421 determines an indoor chemical index for a property by analyzing property data for the property (e.g., a dataset 262 comprising property attributes for the property, user responses to questions relating to the property, etc.) to identify data points that indicate potential chemical presence in the property. Examples of data points that indicate potential chemical presence in the property may include, but are not limited to, the following: (a) building materials, (b) use of cleaning products, laundry detergent, air fresheners or personal care products, and (c) use of chemical pest control. Examples of data points that indicate potential amplifications factors for the indoor chemical index for the property may include, but are not limited to, the following: (a) new building materials containing higher levels of toxic ingredients, (b) use of fragranced cleaning products or personal care products, and (c) frequent use of chemical pest control.

In one embodiment, the property score calculator unit 421 computes an indoor chemical index (ICI) for a property in accordance with equation (5) provided below:

$$ICI = ICI\_Raw \times ICI\_Amplification \times ICI\_TotalBurden \quad (5).$$

In one embodiment, the property score calculator unit 421 computes ICI_Raw based on weighted user responses to questions selected from the collection 264 to identify data points that indicate potential chemical presence in the property. The property score calculator unit 421 computes ICI_Amplification based on weighted user responses to questions selected from the collection 264 to identify data points related to amplifications factors for an indoor chemical index. The property score calculator unit 421 computes the product of ICI_Raw, ICI_Amplification and ICI_TotalBurden to obtain ICI.

In one embodiment, ICI_Amplification is applied to obtain ICI only when three or more amplification factors are present.

Indoor Biological Activity Index

An indoor biological activity index for a property represents a combination of features, including features from other indexes, that result in indoor environmental conditions necessary for germination, amplification, life support, and potential infestation of an indoor environment of the property by a multitude of potential biological life forms. One or more other indexes perform the role of amplification factors for the indoor biological activity index. For example, the indoor dampness index is the primary driving force for the growth of mold, bacteria, dust mites, cockroaches, and rodents plus the release of chemicals from moisture damaged materials and structures, as long as the other necessary environmental conditions are present. Other environmental conditions, structures, and indexes that affect the indoor biological activity index include: (a) water accumulation indoors from pipe leaks, wind driven rain penetration of the roof, cladding on or around windows and doors, and toilet or washing machine overflows, (b) insufficient stoppage of moisture accumulation and removal before biological growth, especially mold, can reproduce and sustain growth, (c) materials, based on the home structural attributes index, that create surfaces and nutrition for infestations, (d) structures, based on the home structural attributes index, that provide pathways for air, moisture, particulate, spores, pollen, insects and other pests, (e) energy, based on the air movement index, to create migration of pollutants and conditions through pathways for air from both outside to inside and to circulate throughout the indoor environment, (f) particulate identified, based on the indoor particulate index, as a primary source of nutrients for biological growth, (g) structures, based on the indoor cavities index, that provide micro-environments for the accumulation of particulate, absorption of moisture, and relatively stable ranges of temperature and available water (aW) per the indoor dampness index to be sufficiently supportive of biological amplification, (h) sources of nutrients and moisture based on the outdoor pollutant index, and (i) based on the air movement index, moisture and subsequent vapor pressure differentials, the wind and subsequent air pressure differentials, and the extent over time that the property is subject to factors which create the imbalance responsible for conditions that are unhealthy for people, but healthy for pestilence.

In one embodiment, the property score calculator unit 421 computes an indoor biological activity index (IBAI) for a property in accordance with equation (6) provided below:

$$IBAI = IBAI\_Raw \times IBAI\_Amplification \times IBAI\_TotalBurden \quad (6).$$

In one embodiment, the property score calculator unit 421 computes IBAI_Raw based on weighted user responses to questions selected from the collection 264 to identify data points related to an indoor biological activity index. The property score calculator unit 421 computes IBAI_Amplification based on weighted user responses to questions selected from the collection 264 to identify data points related to amplifications factors for an indoor biological activity index. The property score calculator unit 421 computes the product of IBAI_Raw, IBAI_Amplification and IBAI_TotalBurden to obtain IBAI.

In one embodiment, IBAI_Amplification is applied to obtain IBAI only when two or more amplification factors are present.

The indoor biological activity index may affect other indexes, resulting in conditions which include, but are not limited to: (a) all biological life takes in nutrients, (b) all biological life excretes waste, and (c) both ingestion and excretion alters the environment the biological life inhabits. All of the other indexes are altered to some extent by the presence of biological activity. The inter-relationships and feedback (both positive and negative) among and between the Indexes creates a dynamically changing indoor environment. When the total set of conditions shifts away from what the human body can easily adjust to, additional energy and action by the human organs and systems are stressed which can eventually result in a movement away from good-health and toward ill-health.

Home Structural Attributes Index

In one embodiment, the property score calculator unit 421 determines a home structural attributes index for a property by analyzing property data for the property (e.g., a dataset 262 comprising property attributes for the property, user responses to questions relating to the property, etc.) to identify data points that indicate potential presence of structures at the property. Examples of data points that indicate potential presence of structures at the property may include, but are not limited to, the following: (a) forced air heating or cooling systems, (b) cooling with air-conditioning, evaporative cooling or natural ventilation, (c) mechanical ventilation, (d) exhaust fans in kitchen or bathrooms, (e) attic, with or without conditioned air, (f) crawlspace, ventilated or conditioned air, with or without a moisture barrier, (g) fireplace, (h) wall to wall carpeting, and extent of coverage, (i) number of rooms, assists in identifying occupancy, (j) stucco cladding, whether natural or synthetic materials, (k) age of the property identifies most likely types of structure, materials, and systems which have historically changed over time, (l) landscaping including slope and vegetation, (m) roof type and slope, such as flat, steep, slight, tile, shingles of asphalt or wood or tile, (n) water removal such as gutters and downspouts, (o) visual conditions of property, such as recent or deferred maintenance, and (p) complex additions to the main building. Examples of data points that indicate potential amplifications factors for the home structural attributes index for the property may include, but are not limited to, the following: old construction, conditions signaling poor maintenance of the property, high property occupancy with inadequate ventilation, over a damp crawlspace.

In one embodiment, the property score calculator unit 421 computes a home structural attributes index (HSAI) for a property in accordance with equation (7) provided below:

$$HSAI = HSAI\_Raw \times HSAI\_Amplification \times HSAI\_TotalBurden \quad (7).$$

In one embodiment, the property score calculator unit 421 computes HSAI_Raw based on weighted user responses to questions selected from the collection 264 to identify data points related to a home structural attributes index. The property score calculator unit 421 computes HSAI_Amplification based on weighted user responses to questions selected from the collection 264 to identify data points related to amplifications factors for a home structural attributes index.

The property score calculator unit 421 computes the product of HSAI_Raw, HSAI_Amplification and HSAI_TotalBurden to obtain HSAI.

In one embodiment, HSAI_Amplification is applied to obtain HSAI only when three or more amplification factors are present.

Indoor Particle Index

An indoor particle index for a property represents a combination of various possible sources of potential particulate (e.g., dust) in an indoor environment of the property, irrespective of other indexes. In one embodiment, the property score calculator unit 421 determines an indoor particle index for a property by analyzing property data for the property (e.g., a dataset 262 comprising property attributes for the property, user responses to questions relating to the property, etc.) to identify data points that indicate potential particulate presence in the property. Examples of data points that indicate potential particulate presence in the property may include, but are not limited to, the following: (a) pet dander from furry pets (e.g., dogs, cats, gerbils, hamsters), (b) human dander from high property occupancy, (c) particulate accumulation due to hard to clean surfaces such as wall to wall carpeting, unfinished beams or wall paneling, horizontal display surfaces such as elevated structures, (d) particulate accumulation due to forced air systems. Examples of data points that indicate potential amplifications factors for the indoor particle index for the property may include, but are not limited to, the following: multiple furry pets, hard to clean surfaces, and types of forced air systems.

In one embodiment, the property score calculator unit 421 computes an indoor particle index (IPI) for a property in accordance with equation (8) provided below:

$$IPI = IPI\_Raw \times IPI\_Amplification \times IPI\_TotalBurden \quad (8).$$

In one embodiment, the property score calculator unit 421 computes IPI_Raw based on weighted user responses to questions selected from the collection 264 to identify data points related to an indoor particle index. The property score calculator unit 421 computes IPI_Amplification based on weighted user responses to questions selected from the collection 264 to identify data points related to amplifications factors for an indoor particle index. The property score calculator unit 421 computes the product of IPI_Raw, IPI_Amplification and IPI_TotalBurden to obtain IPI.

In one embodiment, IPI_Amplification is applied to obtain IPI only when two or more amplification factors are present.

Indoor Dampness Index

An indoor dampness index for a property represents a combination of various possible sources of dampness in an indoor environment of the property, irrespective of the other indexes. In one embodiment, the property score calculator unit 421 determines an indoor dampness index for a property by analyzing different datasets (e.g., a database 260 maintaining property attributes for the property, user responses to questions, etc.) to identify data points related to an indoor dampness index. The datasets may include data identifying potential dampness presence in the property. Examples of data points that relate to an indoor dampness index may include, but are not limited to, the following: (a) roof type and age, (b) plumbing type and age, (c) exterior cladding type and age, with or without moisture barrier and insulation, (d) basements, whether full, partial, sub-surface, garden-level, or walk-out, (e) crawlspaces, whether installed moisture barrier on open soil, or "rat" slab, (f) cold surfaces such as single pane windows, insufficient insulation in exterior walls, (g) number of bathroom showers, with or without bathroom exhaust fans, (h) cooking behaviors with or without kitchen exhaust fans, (i) high occupancy, excess production of exhaled vapor in human breath, and (j) open-water features such as indoor swimming pools, hot tubs, water fountains, steam rooms. Examples of data points that indicate potential amplifications factors for the indoor dampness index for the property may include, but are not limited to, the following: old and damaged exteriors, damp crawlspaces, history of water damage, and conditions signaling poor maintenance of the property. If two or more are present, then a multiplier is applied to the Index.

In one embodiment, the property score calculator unit 421 computes an indoor dampness index (IDI) for a property in accordance with equation (9) provided below:

$$IDI = IDI\_Raw \times IDI\_Amplification \times IDI\_TotalBurden \quad (9).$$

In one embodiment, the property score calculator unit 421 computes IDI_Raw based on weighted user responses to questions selected from the collection 264 to identify data points related to an indoor dampness index. The property score calculator unit 421 computes IDI_Amplification based on weighted user responses to questions selected from the collection 264 to identify data points related to amplifications factors for an indoor dampness index. The property score calculator unit 421 computes the product of IDI_Raw, IDI_Amplification and IDI_TotalBurden to obtain IDI.

In one embodiment, IDI_Amplification is applied to obtain IDI only when two or more amplification factors are present.

Outdoor Environmental Index

An outdoor environmental index for a property represents a combination of various possible outdoor environmental features and conditions, including influences such as climate, geography, landscape, and other features outside of a building envelope of the property, irrespective of the other indexes. In one embodiment, the property score calculator unit 421 determines an outdoor environmental index for a property by analyzing property data for the property (e.g., a dataset 262 comprising property attributes for the property, user responses to questions relating to the property, etc.) to identify data points that indicate potential climate features of the property. Examples of data points that indicate potential climate features of the property may include, but are not limited to, the following: (a) climate zone, such as hot-humid, hot-dry, cold, frigid, moderate, or mixed—affecting energy usage per degree day calculations, (b) geography, such as desert, mountain, plains, coastal, forest, (c) locations such as urban, suburbs, inner city, industrial, large housing lots, (d) seasonality, for weather conditions and storms, plus pollen production, and outdoor activities such as construction, lawn care, farming activities, tourism, (e) area wind direction and patterns, and (f) local features and structures such as tall buildings, trees, and hills that provide extensive shading from the sun. Examples of data points that indicate potential amplifications factors for the outdoor environmental index for the property may include, but are not limited to, the following: extremes of climate and geography, shading of the sun, stormy weather.

In one embodiment, the property score calculator unit 421 computes an outdoor environmental index (OEI) for a property in accordance with equation (10) provided below:

$$OEI = OEI\_Raw \times OEI\_Amplification \times OEI\_TotalBurden \quad (10).$$

In one embodiment, the property score calculator unit 421 computes OEI_Raw based on weighted user responses to questions selected from the collection 264 to identify data points related to an outdoor environmental index. The property score calculator unit 421 computes OEI_Amplification based on weighted user responses to questions selected from the collection 264 to identify data points related to amplifications factors for an outdoor environmental index. The property score calculator unit 421 computes the product of OEI_Raw, OEI_Amplification and OEI_TotalBurden to obtain OEI.

In one embodiment, OEI_Amplification is applied to obtain OEI only when three or more amplification factors are present.

Air Movement Index

An air movement index for a property represents a combination of various possible sources, types, and intensities of factors—both internal and external—creating various pressure differentials across structures both outdoors and indoors. The air movement index further represents a combination of various possible sources of pathways for air from both outside to inside and to circulate throughout the indoor environment. The air movement index, unlike other indexes, is generated primarily by a combination of features selected from other indexes for the property.

In one embodiment, the property score calculator unit 421 determines the air movement index for the property by analyzing property data for the property (e.g., a dataset 262 comprising property attributes for the property, user responses to questions relating to the property, etc.) to identify data points that indicate potential pressure differentials and sources of pathways for air for the property. Examples of data points that indicate potential pressure differentials and sources of pathways for air for the property may include, but are not limited to, the following: (a) climate zone (e.g., hot-humid, hot-dry, cold, frigid, moderate, mixed, etc.) affecting energy usage per degree day calculations, (b) prevailing wind direction and strength, (c) vapor pressure difference between inside and outside the structure, (d) frequency of directional change of air pressures, (e)

frequency of directional change of vapor pressures, (f) leak rate of house per blower door test at 50 Pascal, (g) operation of exhaust fans inside the house in bathrooms, kitchens, hot tub rooms, laundry rooms for clothes dryer exhaust, attic fans for house cooling, (h) use of mechanical ventilation such as HRV or ERV, and (i) air barriers on exterior assemblies combined with sufficient insulation. Examples of amplifications factors for an air movement index may include, but are not limited to, the following: frequent vapor pressure changes, frequent increases in wind strength, a leaky property. Examples of data points that indicate potential amplifications factors for the air movement index for the property may include, but are not limited to, the following: (a) routine construction (e.g., if building envelope is not air tight, multiple tiny openings may accumulate to several square feet total), (b) chimneys, (c) crawlspaces not air sealed to rest of house, (d) forced air systems and ducting located in attics or crawlspaces, (e) combustion make-up air vent (code required for gas fired appliances), (f) water heater exhaust vents, (g) furnace or boiler exhaust vents, (h) cracks in basement floor, (i) dryer exhaust vent, (j) stove hood vent, (k) access door to attic, (l) ceiling penetrations into cavities or attics, (m) poor fitting windows and doors, and (n) perimeter drainage pipes into sump pit.

In one embodiment, the property score calculator unit 421 computes an air movement index (AMI) for a property in accordance with equation (11) provided below:

$$AMI = AMI\_Raw \times AMI\_Amplification \times AMI\_TotalBurden \qquad (11).$$

In one embodiment, the property score calculator unit 421 computes AMI_Raw based on weighted user responses to questions selected from the collection 264 to identify data points related to an air movement index. The property score calculator unit 421 computes AMI_Amplification based on weighted user responses to questions selected from the collection 264 to identify data points related to amplifications factors for an air movement index. The property score calculator unit 421 computes the product of AMI_Raw, AMI_Amplification and AMI_TotalBurden to obtain AMI.

In one embodiment, AMI_Amplification is applied to obtain AMI only when two or more amplification factors are present.

Indoor Cavity Index

An indoor cavity index for a property represents a combination of various possible sources and types of interstitial cavities in structural assemblies in indoor environment of the property, irrespective of other indexes. In one embodiment, the property score calculator unit 421 determines an indoor cavity index for a property by analyzing property data for the property (e.g., a dataset 262 comprising property attributes for the property, user responses to questions relating to the property, etc.) to identify data points that indicate potential cavities in the property. Examples of data points that indicate potential cavities in the property may include, but are not limited to, the following: (a) large number of rooms for that particular house size, (b) complex system of interior walls, (c) additions to the main building, (d) partial attics, (e) partially finished basements, (f) cathedral ceilings, (g) air ducting utilizing "panned" returns in flooring, or located inside wall, floor, or ceiling assemblies, and (h) total rooms. Examples of data points that indicate potential amplifications factors for the indoor cavity index for the property may include, but are not limited to, the following: multiple additions, "panned" forced air returns, and partial attics.

In one embodiment, the property score calculator unit 421 computes an indoor cavity index (ICAVI) for a property in accordance with equation (12) provided below:

$$ICAVI = ICAVI\_Raw \times ICAVI\_Amplification \times ICAVI\_TotalBurden \qquad (12).$$

In one embodiment, the property score calculator unit 421 computes ICAVI_Raw based on weighted user responses to questions selected from the collection 264 to identify data points related to an indoor cavity index. The property score calculator unit 421 computes ICAVI_Amplification based on weighted user responses to questions selected from the collection 264 to identify data points related to amplifications factors for an indoor cavity index. The property score calculator unit 421 computes the product of ICAVI_Raw, ICAVI_Amplification and ICAVI_TotalBurden to obtain ICAVI.

In one embodiment, ICAVI_Amplification is applied to obtain ICAVI only when four or more amplification factors are present.

In one embodiment, the property score application 420 comprises a property analysis unit 429. In one example implementation, the property analysis unit 429 functions as a building architecture and materials recommendation engine for providing recommendations, based in part on the database 900, on how to build new properties that are customized to best address local pollutants and sensitivities of a local population, thereby reducing risk of liability for builders, developers, etc.

In another example implementation, the property analysis unit 429 functions as a housing stock analysis tool for tracking and assessing health index of multiple properties (e.g., housing stock) owned, controlled and/or managed by governments, property management groups, developers, builders, etc.

In another example implementation, the property analysis unit 429 functions as a geographic region/multiple properties analysis tool for determining potential health issues associated with a particular geographical area.

In another example implementation, the property analysis unit 429 functions as a property improvement retailor recommendations tool for providing recommendations, based in part on the database 900, on what building materials to sell, when to sell the building materials, and who to sell the building materials to, based on regional population health and health risks of a property.

Figure 6:
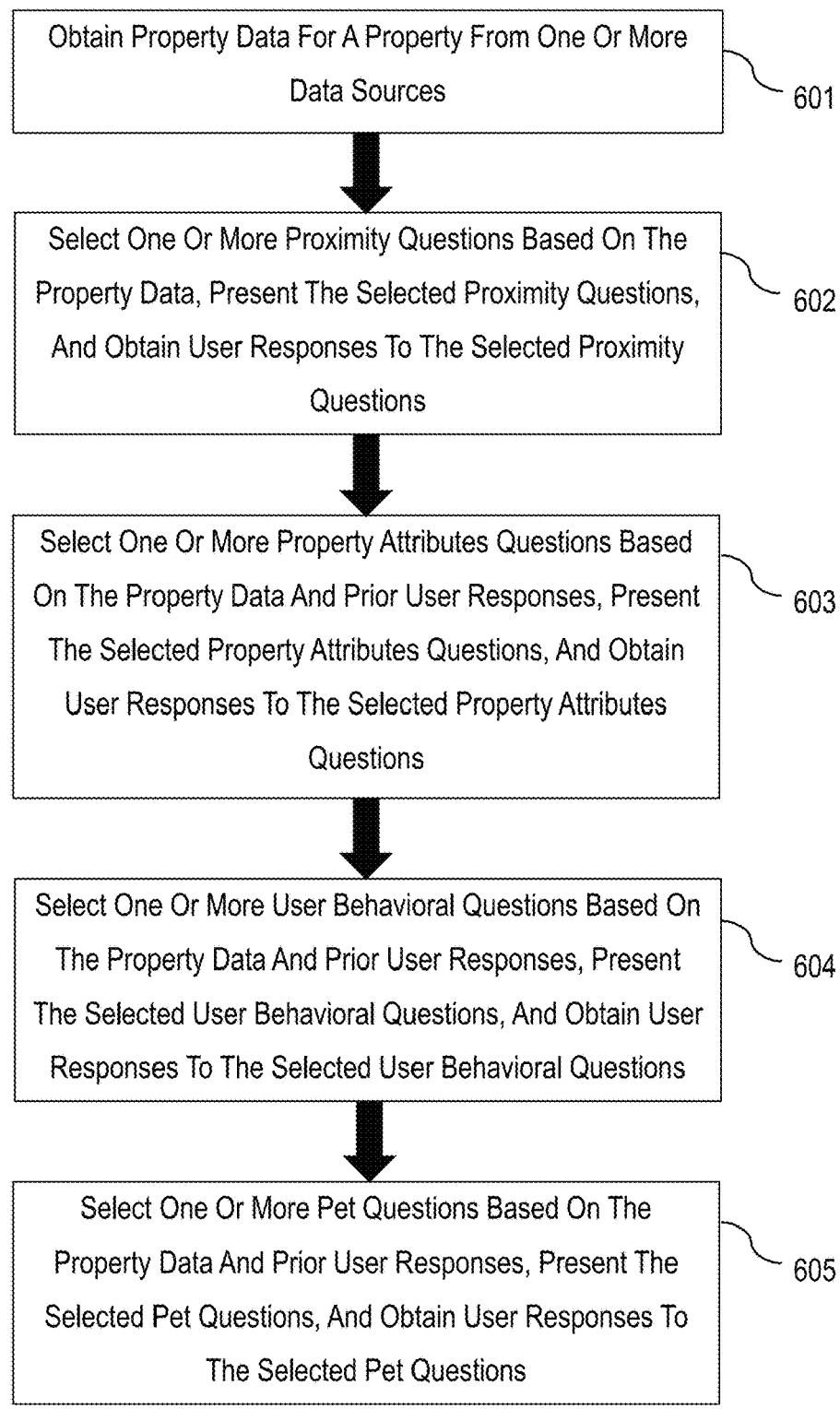
FIG. 6 illustrates an example process 600 for obtaining information used in determining a property score for a property, in accordance with an embodiment of the invention.

FIG. 6 illustrates an example process 600 for obtaining information used in determining a property score for a property, in accordance with an embodiment of the invention. In process block 601, obtain property data for a property from one or more data sources. In one embodiment, the property data includes climate data about environment around the property and public data about the property and its construction (e.g., age of property, average precipitation in the environment around the property, whether the property is located in an urban area, last major construction of the property, age of roof of the property).

In process block 602, select one or more proximity questions based on the property data, present the selected proximity questions, and obtain user responses to the selected proximity questions. In one embodiment, the selected proximity questions are selected from a question bank 265B (FIG. 3).

In process block 603, select one or more property attributes questions based on the property data and prior user responses, present the selected property attributes questions, and obtain user responses to the selected property attributes questions. In one embodiment, the selected property attributes questions are selected from a question bank 265A (FIG. 3).

In process block 604, select one or more user behavioral questions based on the property data and prior user responses, present the selected user behavioral questions, and obtain user responses to the selected user behavioral questions. In one embodiment, the selected user behavioral questions are selected from a question bank 265D (FIG. 3).

In process block 605, select one or more pet questions based on the property data and prior user responses, present the selected pet questions, and obtain user responses to the selected pet questions. In one embodiment, the selected pet questions are selected from a question bank 265C (FIG. 3).

The order of process blocks 602-605 may change; any one of the process blocks may lead to any other one of the process blocks.

Figure 7:
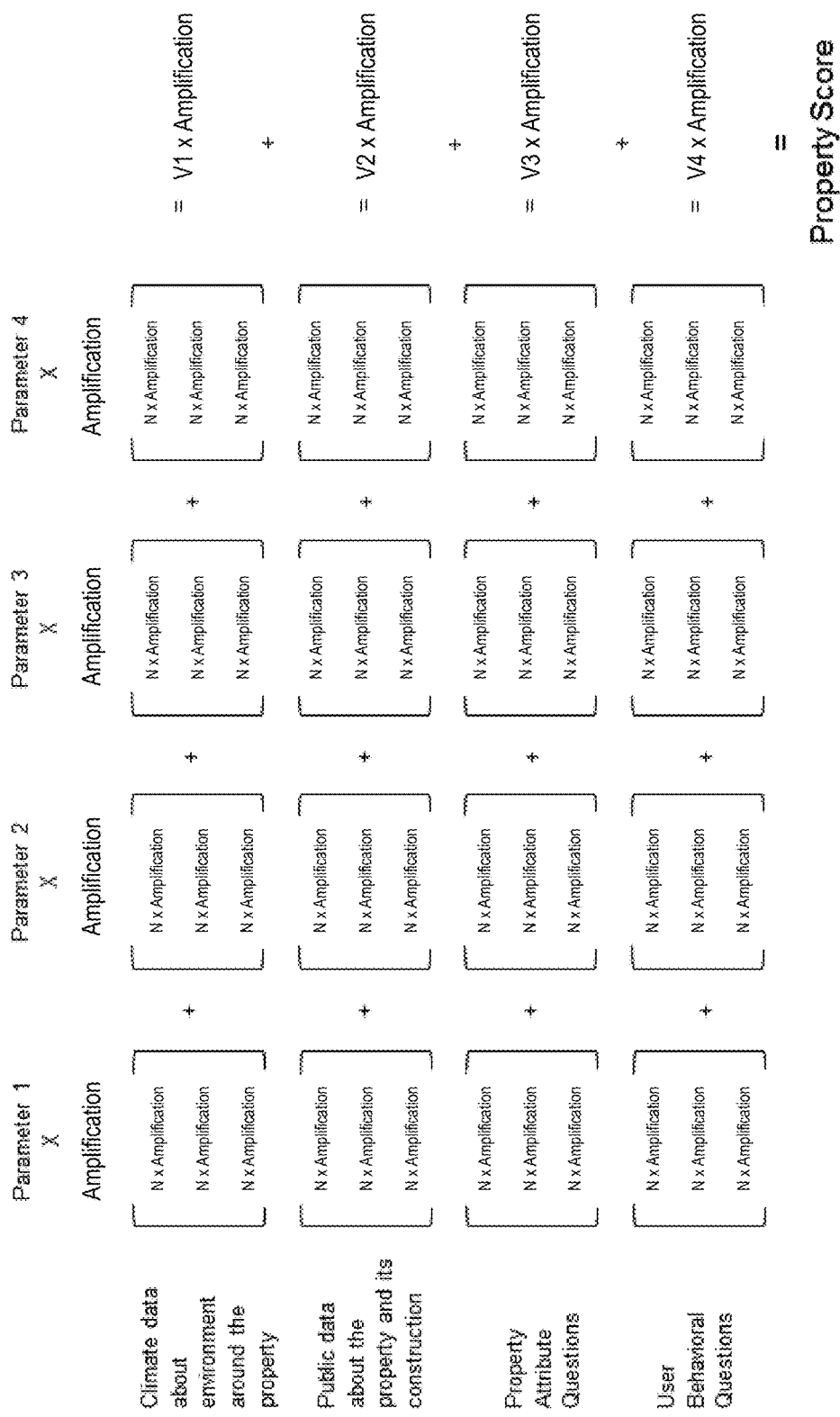
FIG. 7 illustrates an example algorithm 425 applied by the score calculator unit 421 to determine a property score for a property, in accordance with an embodiment of the invention.

FIG. 7 illustrates an example algorithm 425 applied by the property score calculator unit 421 to determine a property score for a property, in accordance with an embodiment of the invention. The property score calculator unit 421 computes a property score for a property based on different subsets of property attributes, such as a first subset of property attributes determined from climate data about environment around the property, a second subset of property attributes determined from public data about the property and its construction, a third subset of property attributes determined from user responses to property attribute questions selected from the question bank 265A, and a fourth subset of property attributes determined from user responses to user behavioral questions selected from the question bank 265D.

For each subset, one or more property attributes N of the subset are assigned an amplification factor. The value of each property attribute N may differ based on potential impact (i.e., severity) that the property attribute N has in influencing an overall value of a parameter corresponding to a pollutant. A value may be defined for each property attribute N, and the property attribute N may be factored into the calculation of more than one parameter (i.e., may be factored into the calculation of different parameters for different pollutants). For example, for each parameter (e.g., Parameter 1, Parameter 2, Parameter 3, Parameter 4), the value of each property attribute N factored into the calculation of the parameter is summed. The overall value of each parameter is then summated as a value V for the subset (e.g., V1 for the first subset, V2 for the second subset, V3 for the third subset, V4 for the fourth subset), and the value V is applied an amplification factor representing the potential impact (i.e., severity) of the subset on the health of a mean population demographic. Furthermore, the overall value of each parameter may be amplified on a pollutant basis such that the overall value of any one parameter corresponding to a pollutant does not overly influence the property score. Finally, each amplified value V is summated, and the resulting sum represents the property score.

The number of parameters may be variable. For example, if determining the potential impact of mold on the property, the parameters utilized may include an air movement index and model data for modeling/projecting the growth of mold. In one example scenario, some property attributes for the property are used to determine the air movement index and the model data for modeling/projecting the growth of mold, which are then summated to determine the potential impact of mold on the property. In this example scenario, the property attributes are not factored directly in the algorithm 425; the property attributes, instead, are used in a subsystem that generates a result that is factored directly in the algorithm 425.

Figure 8:
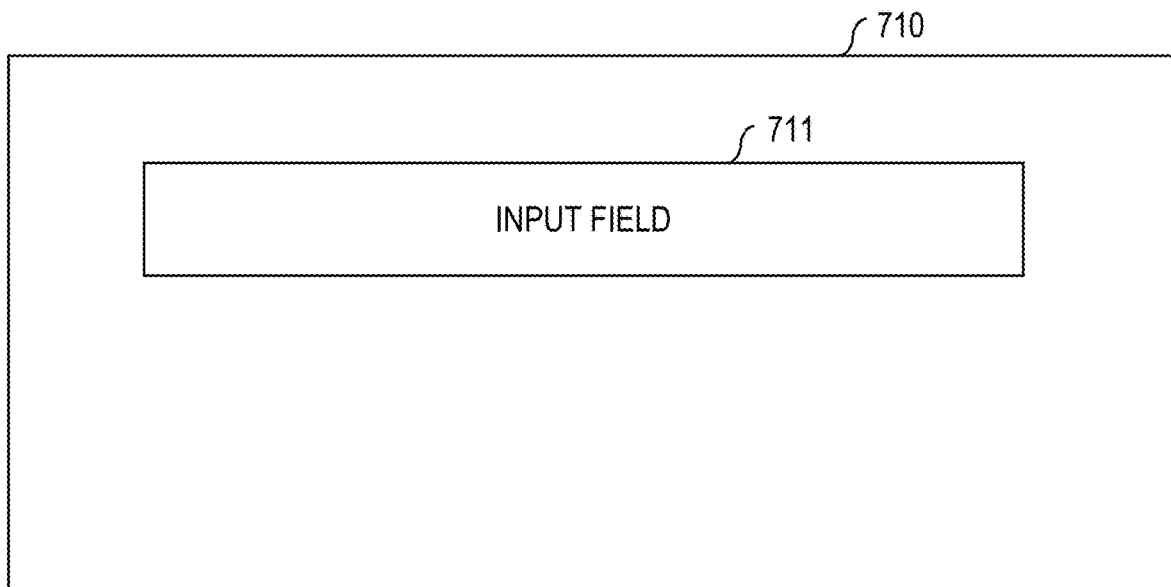
FIG. 8 illustrates an example webpage 710, in accordance with an embodiment of the invention.

FIG. 8 illustrates an example webpage 710, in accordance with an embodiment of the invention. The webpage 710 prompts a user accessing the webpage 710 via a user client device 299 for a property address. In one embodiment, the webpage 710 includes a first region 711 comprising an input field for receiving user input. The user may directly enter a property address into the input field.

In one embodiment, if the user client device 299 has geo-location capabilities, the property address may be acquired instead via latitudinal and longitudinal positions provided by the user client device 299, without any user input.

Figure 9:
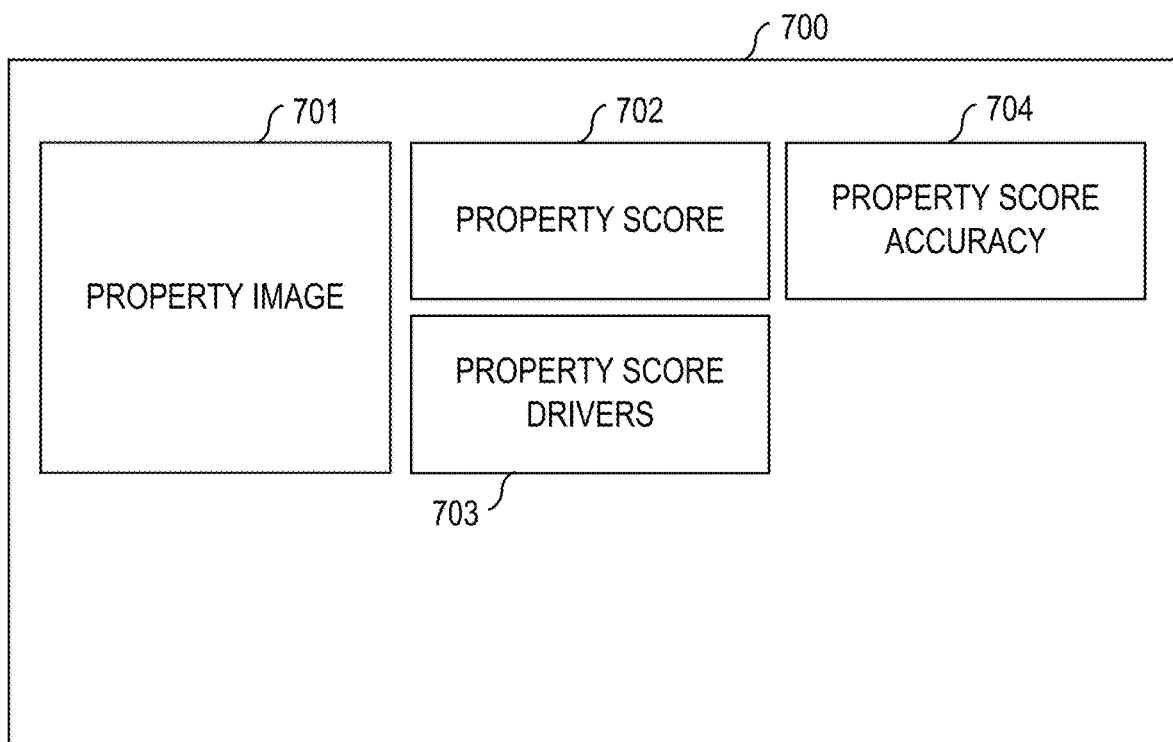
FIG. 9 illustrates an example webpage 700 generated in response to receiving a property address, in accordance with an embodiment of the invention.

FIG. 9 illustrates an example webpage 700 generated in response to receiving a property address, in accordance with an embodiment of the invention. In one embodiment, the webpage 700 includes a first region 702 that displays a property score for the property address. The property score is determined using the property score application 420. The webpage 700 further includes a second region 701 displaying an image/photo of a property located at the property address, and a third region 703 displaying a legend identifying one or more property attributes for the property that has negatively impacted or positively impacted the property score.

The webpage 700 may further include a fourth region 704 identifying a projected accuracy rating for the property score. The accuracy rating increases or decreases depending on the amount and/or accuracy of data points available for the property address (e.g., the amount and/or accuracy of property attributes acquired from third-party data sources and/or a user responses). The fourth region 704 may further display a selectable graphical user interface (GUI) component that, when selected, provides a user with an opportunity to increase the amount and/or accuracy of data points available for the property address by manually entering additional information, thereby refining the property score.

If the user selects the GUI component, the user is directed to another webpage presenting questions selected from the collection 264, wherein the questions presented prompt the user to enter additional information. Additional property attributes for the property are determined based on the additional information entered, and the additional property attributes are stored in the database 260 for the property. The score calculator unit 421 updates the property score based on the additional property attributes determined.

The webpage 700 may include additional regions displaying other information, such as the average estimated property score for properties located in the same city as the property address, information identifying common illnesses, information identifying physical and/or geographic characteristics that negatively impact human health, information identifying cities with properties having the highest property scores, etc.

Personal Profile Application

In this specification, the term "personal profile" is used to denote a profile for a user. A personal profile for a user may include one or more of the following information relating to the user: sensitivities of the user, specific triggers of the user, thresholds of the user, and impacts of the user. The term "personal profile score" represents a health index for a user with respect to sensitivities of the user, specific triggers of the user, thresholds of the user, and impacts of the user. A personal profile score may be represented using a number grade, a percentage grade, a letter grade, etc.

Figure 10:
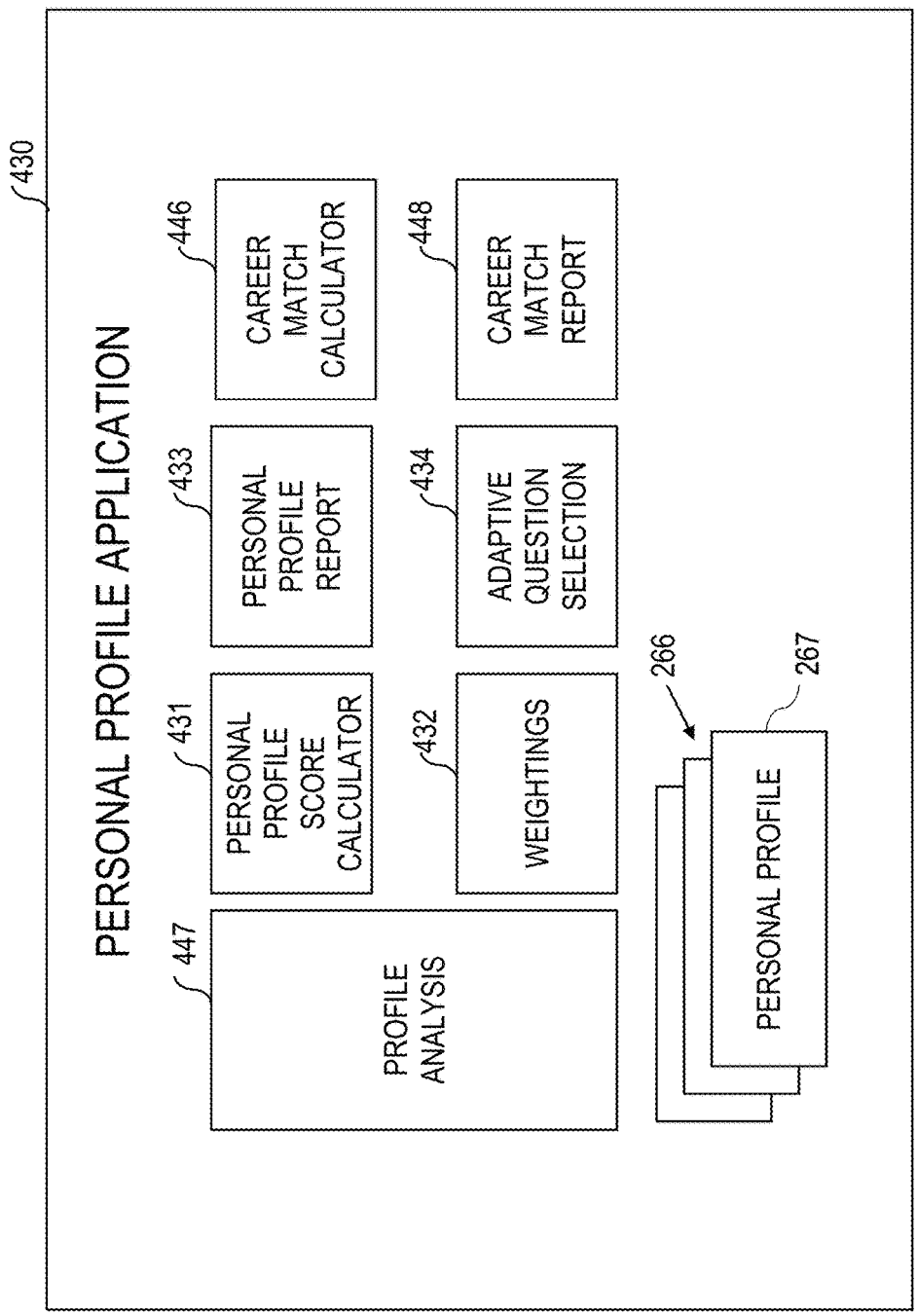
FIG. 10 illustrates an example personal profile application 430, in accordance with an embodiment of the invention.

FIG. 10 illustrates an example personal profile application 430, in accordance with an embodiment of the invention. In one embodiment, one of the applications 410 (FIG. 2) executing/operating on the server devices 210 (FIG. 1) is a personal profile application 430. The personal profile application 430 comprises a personal profile score calculator unit 431 configured to create a personal profile for a user, and determine a personal profile score for the user based on the personal profile created.

The personal profile score calculator unit 431 may create a personal profile for a user based on user input (e.g., user responses to questions selected from the collection 264) and/or health records for the user. A personal profile for a user may be maintained in at least one database 260. In one embodiment, the storage devices 220 (FIG. 1) maintains at least one database 260 including a collection 266 of personal profiles 267 for different users.

In one embodiment, to create a personal profile for a user, the user is presented with questions selected from the collection 264 (e.g., presented with 20 questions selected from a collection of more than 100 questions) to obtain personal data of the user. The selected questions may cycle through questions for determining sensitivities of the user to biologicals, chemicals, particles, and pets, respectively.

The personal profile application 430 comprises an adaptive question selection unit 434 for adaptively selecting questions from the collection 264 based in part on prior user input (e.g., prior user responses to questions selected from the collection 264), if any. If, at any point during the presentation of the selected questions, user responses seem contradictory or mis-entered, the adaptive question selection unit 434 runs a related education module and then repeats or rephrases the selected questions. Questions selected and presented to a user are dynamically selected based on prior user interactions (e.g., prior user responses). For example, if prior user responses to initial screening questions indicate that pets are not an issue to a user but biologicals are, the likelihood of questions relating to biologicals being subsequently selected and presented to the user increases whereas the likelihood of questions relating to pets being subsequently selected and presented to the user decreased.

In one embodiment, the personal profile application 430 comprises a weightings unit 432. The weightings units 432 comprises, but is not limited to, the following: (a) different weighting values for different attributes, factors or indexes, (b) different prevalence values for different attributes, factors or indexes, and (c) data representing interrelationships between different attributes, factors or indexes.

In one embodiment, the personal profile application 430 comprises a personal profile report unit 433 for generating a personal profile report that includes a personal profile for a user and a personal profile score for the user. A personal profile report may be presented to a user via a website 295.

In one embodiment, a personal profile for a user maintained in the database 260 is updated when updated/additional information relating to the user obtained.

In one embodiment, the personal profile score calculator unit 431 is configured to create a group profile for a group of multiple users by combining each personal profile for each user of the group. There may be different types of groups comprising multiple users. Examples of different types of groups comprising multiple users may include, but are not limited to, the following: a family group comprising multiple family members, a population group comprising multiple members (e.g., a local population, etc.). A group profile for a group of users may include one or more of the following information relating to the group: sensitivities of the group, specific triggers of the group, thresholds of the group, and impacts of the group. In one example implementation, the personal profile score calculator unit 431 adds up sensitivities of each user the group, specific triggers of each user the group, thresholds of each user the group, and impacts of each user the group to determine sensitivities of the group, specific triggers of the group, thresholds of the group, and impacts of the group, respectively. The sensitivities of the group is determined such that it reflects sensitivities of the most sensitive user of the group.

In one embodiment, a personal profile report for a user includes a personal action plan customized for the user. The personal profile report unit 433 determines how compatibility between a user and a property may be misaligned, and generates personal action plan including remediation recommendations, wherein the remediation recommendations suggest actions and/or interventions for the user to take to remedy any potential mis-match between the user and the property and improve compatibility between the user and the property (i.e., improving a property match score). The personal action plan may be based in part on user feedback with respect to past actions taken and results, expert judgment and other data correlations. The personal action plan may also be based on user feedback with respect to goals of the user, budget of the user and/or desired outcomes of the user. For example, to elicit user feedback from the user with respects to goals of the user, budget of the user and/or desired outcomes of the user, the personal profile report unit 433 may present questions selected from the collection 264 (e.g., personal motivations and goals questions selected from the question bank 265E). User responses received in response to the questions presented are used to further personalize/customize the personal action plan for the user. A personal action plan may be presented to a user via a website 295.

In one embodiment, the personal action plan comprises a prioritized set of remediation recommendations, wherein the remediation recommendations suggest a particular order of actions and/or interventions for the user to take in order to yield maximum benefit and compliance. The personal action plan may also include actions to avoid and guidance on interpretation of results. The remediation recommendations are prioritized based on data correlations, such as correlations among property attributes used in determining a property score, personal profiles, expert judgment, survey results, and user feedback with respect to prior remediation interventions and/or actions performed and results/impact. Necessary remediation interventions and/or actions may also be covered by existing guidance documents and/or standards.

Table 2 below provides an example personal profile report generated by the personal profile application 430.

TABLE 2

Personal Profile
Your personal profile score is 80. You have some significant sensitivities, but are overall around average and share this score with an estimated 50% of the U.S. population and about 40% of users of the Personal Profile tool.
You are highly sensitive to chemicals, which can easily cross the threshold for triggering a response. These interruptions, however, are at a nuisance level (2 out of 6 with 1 being no impact and 6 being life threatening) and do not typically require substantial lifestyle changes or cause significant harm.

TABLE 2-continued

A few example data points used in this determination are:
Your sensitivity to diesel fuel
A dislike of the cleaning aisle
A strong response to air fresheners
An assessment that you don't leave a room with an air freshener
Nail polish bothers you, but you go to nail salons regularly
Some specific chemicals that affect you are:
Alcohol based perfumes
Petroleum products
You are moderately sensitive to particles. While particles don't easily cross the threshold to
trigger a response, when you have a response it is rather strong. These interruptions, are at a 4
out of 6 (2 out of 6 with 1 being no impact and 6 being life threatening).
A few example data points used in this determination are:
Sensitivity to cigarette smoke
Comfort around 2-3 dogs, but inability to go into pet stores
Seasonal allergies that are non-existent most of the year, but severe a few times a year
Comfort with cleaning and vacuuming for all rooms except the attic, which you avoid
Allergies to cats that prevent you from visiting friends with cats at their properties,
though meeting outside it fine
Some specific particles that affect you are:
Cat dander
Pollen
You have a low sensitivity to biologicals. You have a relatively high trigger point and are not
substantially bothered by biologicals. These interruptions, are at a nuisance level (2 out of 6 with
1 being no impact and 6 being life threatening).
A few example data points used in this determination are:
The dampness of your current living environment
Your lack of sinus infections during past stays in musty properties and dorms
Your love of antiques, old carpets and upholstery
Personal Action Plan
We recommend keeping windows closed during peak allergy seasons. 30% of people
with personal profiles like yours report significant improvements in how they feel after
implementing this strategy.
Use only low toxic cleaning materials and air out the house while doing so with open
windows. 50% of people with personal profiles like yours report significant improvements in
how they feel after implementing this strategy.

In one embodiment, after a personal action plan is presented to a user for review, the personal profile report unit 433 is configured to refine/adjust the personal action plan based on user feedback. For example, to elicit user feedback from the user, the personal profile report unit 433 may present questions selected from the collection 264 (e.g., feedback and assessment questions selected from the question bank 265L, or other questions such as "Which of the suggested interventions would you like to do first?" or "What deadline do you want to give yourself for this action?"). User responses received in response to the questions presented are used to refine/adjust the personal action plan for the user.

In this specification, the term "trigger" is used to represent a substance/item, without any assigned weighting, that has a perceived impact on an individual (i.e., how the individual reacts to the substance). Examples of triggering items may include nail polish, pet dander, or petroleum products.

A threshold for a trigger denotes how much of a trigger must be present to elicit a response from a user.

An impact rating for a trigger denotes severity of a response an individual will exhibit when a threshold for the trigger is crossed.

The personal profile score calculator unit 431 is configured to collect different reported triggers from a user, and determine the influence of each reported trigger on a personal profile score based on a corresponding weighting value and a corresponding prevalence value.

In one embodiment, the personal profile application 430 determines a health sensitivity data (e.g., pattern relating to a sensitivity) from personal data associated with a user. The personal profile application 430 determines a potential impact data (e.g., pattern relating to personal impact) that a pollutant data (e.g., pattern relating to a pollutant) may have on health of the user based in part on the health sensitivity data, and generates a personal profile for the user, wherein the personal profile comprises a personal profile score representing health sensitivities of the user to pollutants based in part on the potential impact data.

In one embodiment, the personal profile score calculator unit 431 determines a personal profile score for a user based on the following factors/indexes: specific triggers (i.e., biologicals, chemicals, particles and pets), prevalence and thresholds for the specific triggers, impact rating of the specific triggers, and total burden. A selection of top triggers corresponding may be included in a personal profile report generated for a user.

Table 3 provided below comprises a listing identifying different parameters referenced in this specification.

TABLE 3

| Abbreviation | Definition |
| --- | --- |
| PersonalProfile_Score | Personal profile score |
| BiologicalSensitivity | Raw score for biologicals trigger |
| BiologicalThresholds_Sum | Sum of thresholds for biologicals trigger |
| BiologicalThresholds_Amplification | Thresholds amplification factors for biologicals trigger |

TABLE 3-continued

| Abbreviation | Definition |
| --- | --- |
| BiologicalImpactRatings | Impact ratings for biologicals trigger |
| BiologicalImpactRatings__Amplification | Impact ratings amplification factors for biologicals trigger |
| MoldSensitivity | Raw score for mold trigger |
| MoldThresholds__Sum | Sum of thresholds for mold trigger |
| MoldThresholds__Amplification | Thresholds amplification factors for mold trigger |
| MoldImpactRatings | Impact ratings for mold trigger |
| MoldImpactRatings__Amplification | Impact ratings amplification factors for mold trigger |
| Chemical Sensitivity | Raw score for chemicals trigger |
| ChemicalThresholds__Sum | Sum of thresholds for chemicals trigger |
| ChemicalThresholds__Amplification | Thresholds amplification factors for chemicals trigger |
| ChemicalImpactRatings | Impact ratings for chemicals trigger |
| ChemicalImpactRatings__Amplification | Impact ratings amplification factors for chemicals trigger |
| ParticleSensitivity | Raw score for particles trigger |
| ParticleThresholds__Sum | Sum of thresholds for particles trigger |
| ParticleThresholds__Amplification | Thresholds amplification factors for particles trigger |
| ParticleImpactRatings | Impact ratings for particles trigger |
| ParticleImpactRatings__Amplification | Impact ratings amplification factors for particles trigger |
| PetSensitivity | Raw score for pets trigger |
| PetThresholds__Sum | Sum of thresholds for pets trigger |
| PetThresholds__Amplification | Thresholds amplification factors for pets trigger |
| PetImpactRatings | Impact ratings for pets trigger |
| PetImpactRatings__Amplification | Impact ratings amplification factors for pets trigger |
| TriggerRaw | Raw score for trigger |
| TriggeringItem | Indication (Yes/No) of whether a user reacts to a particular triggering item for a trigger |
| TriggeringItem__Amplification | Amplification factors for a particular triggering item for a trigger |
| ThresholdAmplificationFactors | Threshold amplification factors for trigger |
| ThresholdDeterminationRatings | Threshold determination ratings for trigger |
| ImpactRatings | Impact ratings for trigger |
| MaskingEffects | Masking effects |
| UserBehavioralClues | User behavioral clues |
| UserBehavioralClues__Amplification | Amplification factors for user behavioral clues |
| ImpactRatings__Amplification | Impact ratings amplification factors |

In one embodiment, the personal profile score calculator unit 431 computes PersonalProfile_Score in accordance with the equation (13) provided below:

$$PersonalProfile\_Score = BiologicalSensitivity + MoldSensitivity + Chemical Sensitivity + ParticleSensitivity + PetSensitivity \quad (13)$$

In one embodiment, the personal profile score calculator unit 431 computes BiologicalSensitivity in accordance with the equation (14) provided below:

$$BiologicalSensitivity = BiologicalThresholds\_Sum \times BiologicalThresholds\_Amplification \times BiologicalImpactRatings \times BiologicalImpactRatings\_Amplification \quad (14)$$

In one embodiment, the personal profile score calculator unit 431 computes MoldSensitivity in accordance with the equation (15) provided below:

$$MoldSensitivity = MoldThresholds\_Sum \times MoldThresholds\_Amplification \times MoldImpactRatings \times MoldImpactRatings\_Amplification \quad (15)$$

In one embodiment, the personal profile score calculator unit 431 computes ChemicalSensitivity in accordance with the equation (16) provided below:

$$ChemicalSensitivity = ChemicalThresholds\_Sum \times ChemicalThresholds\_Amplification \times ChemicalImpactRatings \times ChemicalImpactRatings\_Amplification \quad (16)$$

In one embodiment, the personal profile score calculator unit 431 computes ParticleSensitivity in accordance with the equation (17) provided below:

$$ParticleSensitivity = ParticleThresholds\_Sum \times ParticleThresholds\_Amplification \times ParticleImpactRatings \times ParticleImpactRatings\_Amplification \quad (17)$$

In one embodiment, the personal profile score calculator unit 431 computes PetSensitivity in accordance with the equation (18) provided below:

$$PetSensitivity = PetThresholds\_Sum \times PetThresholds\_Amplification \times PetImpactRatings \times PetImpactRatings\_Amplification \quad (18)$$

For each trigger, the personal profile score calculator unit 431 computes Trigger_Raw in accordance with equation (19) provided below:

$$Trigger\_Raw = (TriggeringItem \times TriggeringItem\_Amplification \times ThresholdAmplificationFactors \times ThresholdDeterminationRatings) \times (ImpactRatings \times MaskingEffects + UserBehavioralClues \times UserBehavioralClues\_Amplification \times ImpactRatings\_Amplification) \quad (19)$$

If a raw score computed for a trigger is greater than a display threshold assigned to the trigger, then the trigger is included in a property match report or a personal action plan generated for the user.

A display threshold assigned to a trigger represents degree of importance of including the trigger in a property match report or personal action plan generated for the user. In one embodiment, a display threshold may be assigned one of the following degrees of importance—"high", "medium" or "low". The degree of importance assigned may be based on amount of points accumulated based on weighted data inputs and weighted data correlations. In one example implementation, a "low" degree of importance is assigned to the threshold if the amount of points accumulated is less than 200 points, a "medium" degree of importance is assigned to the threshold if the amount of points accumulated is between 200 and 400 points, and a "high" degree of importance is assigned to the threshold if the amount of points accumulated is more than 400 points.

In one embodiment, an impact rating assigned to a trigger is a ranking that reflects degree of impact the trigger has on a user. In one example implementation, an impact rating assigned to a trigger is a ranking in the range of "1" to "6". For example, a ranking of "1" reflects that the trigger has no impact on the user, a ranking of "2" reflects that the trigger is merely a nuisance and any impact of the trigger on the user is insufficient to trigger an action to alleviate the impact, a ranking of "3" reflects that any impact of the trigger on the user is sufficient to trigger an action to alleviate the impact, a ranking of "4" reflects that any impact of the trigger on the user is pervasive, complex, and life altering, a ranking of "5" reflects that any impact of the trigger on the user is disabling, and a ranking of "6" reflects that any impact of the trigger on the user is nearly non-functioning or life threatening.

The ranking assigned may be based on amount of impact points accumulated based on weighted data inputs and weighted data correlations. For example, a ranking of "1" is assigned if the amount of points accumulated is in the range 1-100, a ranking of "2" is assigned if the amount of points accumulated is in the range 101-200, a ranking of "3" is assigned if the amount of points accumulated is in the range 201-300, a ranking of "4" is assigned if the amount of points accumulated is in the range 301-400, a ranking of "5" is assigned if the amount of points accumulated is in the range 401-500, and a ranking of "6" is assigned if the amount of points accumulated is in the range 501-600.

A threshold amplification factor is a weighted multiplier. A threshold amplification factor lowers a triggering threshold for triggering an item (i.e., makes the triggering item more potent). For example, dusts issues are amplified if the user has a dust allergy and the property has hard to clean places and forced air.

A threshold determination rating is a weighted assessment of how easily an individual is affected by a specific trigger. The personal profile score calculator unit 431 computes a threshold determination rating for a trigger based on user responses to questions selected from the collection 264 (e.g., threshold questions from the question bank 265G).

For example, to determine a threshold determination rating for dust, the questions selected may include the following: "Do you sneeze when you dust or vacuum?", "Do you sneeze when the forced air turns on?", and "Do you sneeze when vacuuming or dusting and the forced air turns on?". The threshold determination rating for dust is based on user responses to the questions selected (e.g., the user responses may indicate that the user can handle dust without reaction). The threshold determination rating for dust is multiplied by a corresponding weighting to determine the threshold for response of the user to dust. Weightings are created by machine learning algorithm over time.

A personal impact rating for a trigger is an assessment on a sliding scale by a user about how much a triggering item for the trigger impacts the user.

A user behavioral clue is an indicator of potential user reactivity. User behavioral clues are determined from user responses to questions selected from the collection 264 (e.g., user behavioral questions selected from the question bank 265D).

An impact amplification factor is a weighted multiplier. An impact amplification factor increases severity of impact of a trigger. For example, impact amplification factors such as upholstery, carpeting and a high suck rate may increase severity of impact of chemicals.

A masking effect for a trigger reduces a user's perception of the impact that the trigger has on the user. For example, smoking, drinking alcohol, or drinking coffee regularly may impact how a user perceives his/her response to pets, mold, and chemicals. Masking effects are determined from user responses to questions selected from the collection 264 (e.g., masking questions selected from the question bank 265J).

A total burden factor is a calculation about how overall sensitivity may make specific sensitivities worse. Sensitivity levels, when appearing in certain combinations, are correlated to significantly higher lower thresholds and/or to specific triggering items and significantly higher impacts on individuals. When a total burden, as calculated from specific trigger scores tips into a high level, the personal profile score calculator unit 431 will adjust and lower thresholds and raise impact scores accordingly based on data and previously discovered correlations from machine learning about how this total level of burden and the components correlates with thresholds and impacts.

In one example use case, assume that user responses to questions indicate the following: (1) nail polish and diesel are specific triggers for the user, (2) the user attempts to avoid each specific trigger with a personal impact score of 3, and (3) the property of interest to the user has materials such as carpeting and retail chemicals. Table 4 below provides example pseudo code for determining a raw score for the chemical trigger based on triggering item nail polish.

TABLE 4 raw score for nail polish =
[triggering item (yes/no) (i.e., Nail polish YES) ×
triggering item amplification factors (i.e., amplification factors for nail polish based on data correlations among a general population, average population response to nail polish, and severity of the average population response) ×
threshold amplification factors (i.e., weighted amplification indicators such as diesel fuel and carpeting) ×
threshold determination rating] ×
[personal impact rating (i.e., 3) +
masking effects +
behavioral clues × behavioral clues amplification factors ×

TABLE 4-continued impact ratings amplification factors (i.e., weighted impact of affirmative user behavioral indicators that confirm or challenge the personal impact rating, such as the user indicating that he/she avoids nail salons and can't be in the same room with someone putting on nail polish)]

As another example, Table 5 below provides example pseudo code for determining a raw score for the chemical trigger based on different triggering items.

TABLE 5 raw score for different chemical triggers =
[Triggering item (yes/no) × triggering item amplification factors
(e.g.,
New clothes YES × amplification factors
Fragrance YES × amplification factors
Paint YES × amplification factors) ×
threshold amplification factors (e.g., new house, plug in deodorizers, scented detergent) ×
threshold determination rating (e.g., user indicates ratings of 4/6, 2/6, 4/6 in response to
questions such as "How much of an issue are these three triggering items?"; also, user responses
to questions relating to environment, behavior and reactivity such as "Do you use perfume or
scented laundry detergent?", "Do you frequently buy new clothes?", "Have you recently
remodeled or repainted?")] ×
[personal impact rating (e.g., user indicates rating of 4/6 in response to
questions such as "What's it like being near these chemicals? How much does it influence
you?") +
masking effects (e.g., user indicates that he/she does not consume coffee or alcohol) +
user behavioral clues (e.g., user indicates that he/she avoids hardware stores and paint aisles) ×
user behavioral clues amplification factors ×
impact ratings amplification factors (e.g., user indicates property is near a freeway and the
property has had recent water leaks)]

As another example, Table 6 below provides example pseudo code for determining a raw score for the biological trigger based on different triggering items.

TABLE 6 raw score for different biological triggers =
[Triggering item (yes/no) × triggering item amplification factors
(e.g.,
Old musty buildings YES × amplification factors
Antiques YES × amplification factors
Old books YES × amplification factors) ×
threshold amplification factors (e.g., property score estimates high mold risk index) ×
threshold determination rating (e.g., user indicates ratings of 3/6, 4/6 in response to questions
such as "How much of an issue are these three triggering items?"; also, user responses to
questions relating to environment, behavior and reactivity that indicate the user avoids the
basement and feels when he/she leaves the property)] ×
[personal impact rating (e.g., user indicates rating of 2/6 in response to
questions such as "What's it like being near mold? How much does it influence you?") +
masking effects (e.g., user indicates that he/she consumes a lot of alcohol and smokes) +
user behavioral clues × user behavioral clues amplification factors ×
impact ratings amplification factors]

Table 7 below provides example questions and user responses used in determining thresholds and impacts for the particles trigger.

TABLE 7

Examples of initial screening questions

What is it like around:
Seasonal changes
Dust
Outdoor windy days
Examples of user responses to user behavioral questions and sensitivity questions that
contribute to threshold determinations I react to following situations:
Forced air turns on
Run vacuum TABLE 7-continued When I dust
When I open the windows
When I was in a previous property (or at other times in my history e.g., college dorm)
Examples of user responses to property attributes questions, user behavioral questions, proximity questions and sensitivity questions that contribute to amplifiers (impact and threshold)

I have forced air
My family has stuffed animals
I have carpeting
I have upholstery
I keep all my windows open
I live near agriculture
I live near construction
I live near a freeway Table 8 below provides example questions and user responses used in determining thresholds and impacts for the pets trigger.

TABLE 8

Examples of initial screening questions

What is it like around pets and animals?
Have I ever had rodents or insects in the house? What was that like?
Examples of pet questions that contribute to threshold determinations How many pets do I have?
Do I respond to the pet dander on someone else's clothes when no pets are around?
Do I respond to pet dander on a spouse that only interacts with pets outside the house?
Do I keep pets outside of the house? Why?
Examples of indicators in user responses to property attributes questions, user behavioral questions, proximity questions and sensitivity questions that contribute to amplifiers (impact and threshold)

Forced air
Carpet
Vacuum
Upholstery
Have pets
Basement or crawlspace

Table 9 below provides example questions and user responses used in determining thresholds and impacts for the biologicals trigger.

TABLE 9

Examples of initial screening questions

What's it like around: old books, musty houses?
What's it like around damp leaves?
What's it like around old carpet?
What's it like around mold?
Examples of indicators in user responses to property attributes questions, user behavioral questions, proximity questions and sensitivity questions that contribute to amplifiers (impact and threshold)

Moisture and dampness
Wetting and drying cycles in living environment
Upholstered furniture In one embodiment, the personal profile application 430 comprises a career match calculator unit 446 configured to determine a career match score representing compatibility between a user and a profession of interest to the user based on a personal profile of the user and information identifying working conditions associated with the profession (e.g., potential exposures associated with a working environment that an individual working in the profession may face). The information identifying working conditions associated with the profession may be acquired from third-party data sources 120 and/or user feedback.

Typically, 25% of employees consciously or unconsciously opt out of a profession they have been working at for a period of time because they do not feel good in their working environment or do not feel motivated. For example, an individual who is chemically sensitive may find working in an environment with high exposure to chemicals unpleasant and may pursue another career. As another example, an individual who works as a painter may succumb to alcoholism as a coping mechanism to illnesses caused from exposure to chemicals while working as a painter. The career match calculator unit 446 provides a tool that allows a user to gauge their compatibility with a particular profession. The higher the compatibility between a user and a profession of interest, the higher the likelihood of the user will feel satisfied, healthy and motivated in the profession.

In one embodiment, the personal profile application 430 comprises a career match report unit 448 configured to generate a career match report for a user based in part on a personal profile for the user and feedback with respect to professions from other users with similar personal profiles. The career match report may include a suggested list of professions for the user to avoid in view of sensitivities of the user. The career match report may also include a suggested list of professions for the user to pursue. A career match report may be presented to a user via a website 295.

In one embodiment, the career match calculator unit 446 is configured to determine a career match score representing compatibility between a user and a property address at which a working environment for a profession of interest to the user is located based on a personal profile of the user and property data for the property address.

Table 10 below provides an example career match report generated by the personal profile application 430.

TABLE 10

Your sensitivity profile is X and your personal impact is Y for Chemicals. People with similar personal profiles generally tend to avoid the following professions and exposures: [suggested list of professions and exposures to avoid]. They are typically successfully employed in these professions: [suggested list of professions to pursue]

In one embodiment, the personal profile application 430 comprises a profile analysis unit 447. In one example implementation, the profile analysis unit 447 functions as a population profile tool for generating, based in part on group profiles created for specific populations, population-level sensitivity analysis reports for the specific populations. The population-level sensitivity analysis reports may be used by politicians, government agencies, companies and other entities to seek insight into the specific populations.

In one example implementation, the profile analysis unit 447 functions as a liability analyzer tool for assessing, based in part on group profiles created for specific populations, likelihood that minor, but common, health issues within the specific populations are caused by industry, such as oil spills, chemical leaks, etc.

In one example implementation, the profile analysis unit 447 functions as an academic outcomes prediction and advice engine for correlating, based in part on group profiles created for regional populations, regional property attributes with regional student performance and suggesting changes to improve academic performance.

In one example implementation, the profile analysis unit 447 functions as a life insurance calculator tool for predicting, based in part on longitudinal data and group profiles created for regional populations, how regional and individual home and health correlations impact life expectancy at the population level.

Figure 11:
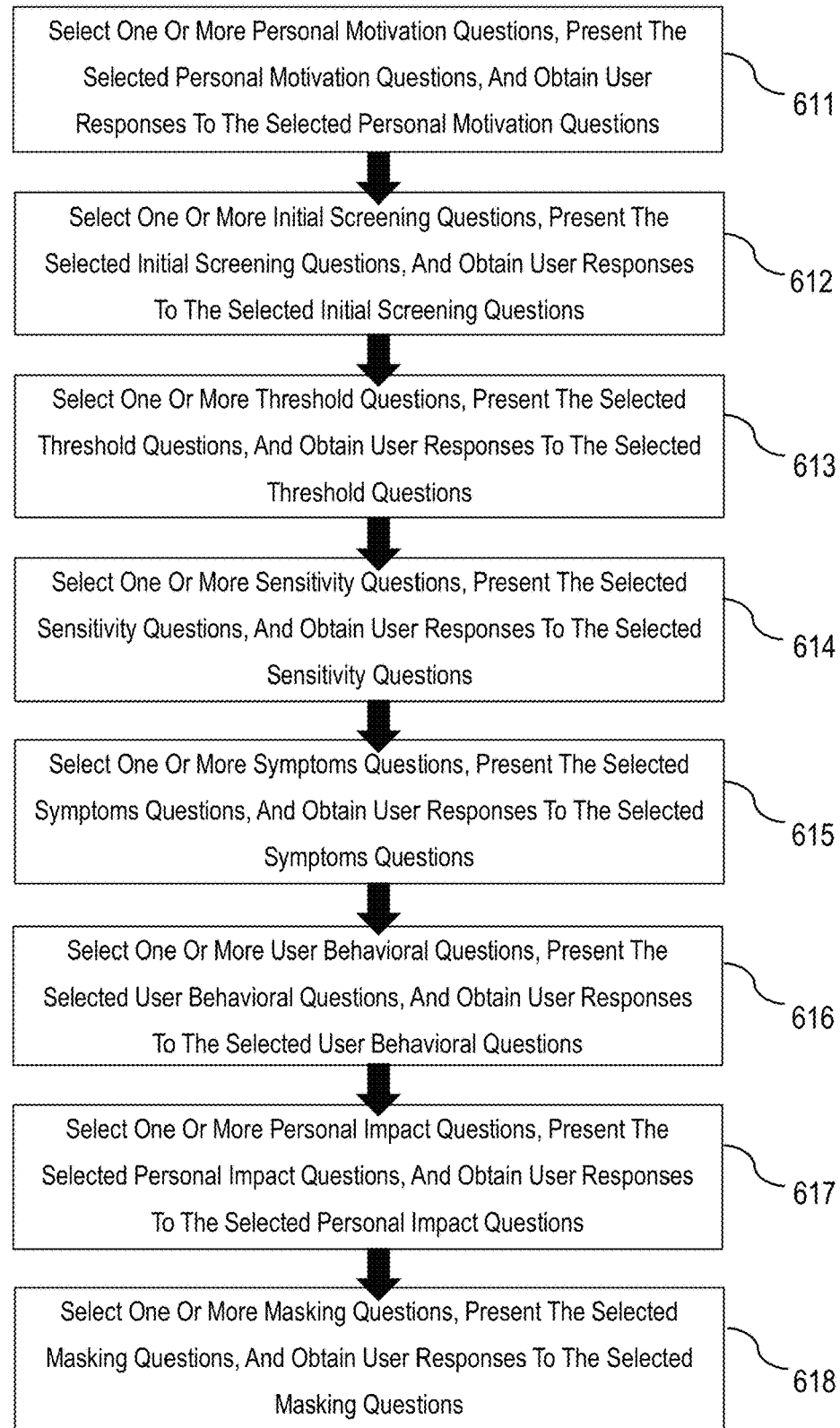
FIG. 11 illustrates an example process 610 for obtaining information used in creating a personal profile for a user, in accordance with an embodiment of the invention.

In one example implementation, the profile analysis unit 447 functions as a relocation recommendation engine for providing, based in part on regional conditions and a personal/group profile, a hyper-local relocation suitability recommendation that suggests targeted regions for relocation FIG. 11 illustrates an example process 610 for obtaining information used in creating a personal profile for a user, in accordance with an embodiment of the invention. In process block 611, select one or more personal motivations and goals questions, present the selected personal motivations and goals questions, and obtain user responses to the selected personal motivations and goals questions. In one embodiment, the selected personal motivations and goals questions are selected from a question bank 265E (FIG. 4).

In process block 612, select one or more initial screening questions, present the selected initial screening questions, and obtain user responses to the selected initial screening questions. In one embodiment, the selected initial screening questions are selected from a question bank 265F (FIG. 4).

In process block 613, select one or more threshold questions, present the selected threshold questions, and obtain user responses to the selected threshold questions. In one embodiment, the selected threshold questions are selected from a question bank 265G (FIG. 4).

In process block 614, select one or more sensitivity questions, present the selected sensitivity questions, and obtain user responses to the selected sensitivity questions. In one embodiment, the selected sensitivity questions are selected from a question bank 265H (FIG. 4).

In process block 615, select one or more symptoms questions, present the selected symptoms questions, and obtain user responses to the selected symptoms questions. In one embodiment, the selected symptoms questions are selected from a question bank 265I (FIG. 4).

In process block 616, select one or more user behavioral questions, present the selected user behavioral questions, and obtain user responses to the selected user behavioral questions. In one embodiment, the selected user behavioral questions are selected from a question bank 265D (FIG. 3).

In process block 617, select one or more personal impact questions, present the selected personal impact questions, and obtain user responses to the selected personal impact questions. In one embodiment, the selected personal impact questions are selected from a question bank 265K (FIG. 4).

In process block 618, select one or more masking questions, present the selected masking questions, and obtain user responses to the selected masking questions. In one embodiment, the selected masking questions are selected from a question bank 265J (FIG. 4).

The order of process blocks 611-618 may change; any one of the process blocks may lead to any other one of the process blocks (e.g., process block 612 may lead directly to process block 616 which in turn leads directly to process block 615).

Property Match Application

In this specification, the term "property match score" is used to denote a grade (e.g., a number grade, a percentage grade, a letter grade) representing compatibility between a property and a user/group of users. A property match score for a property of interest to a user represents compatibility between the property and the user for healthy living.

Figure 12:
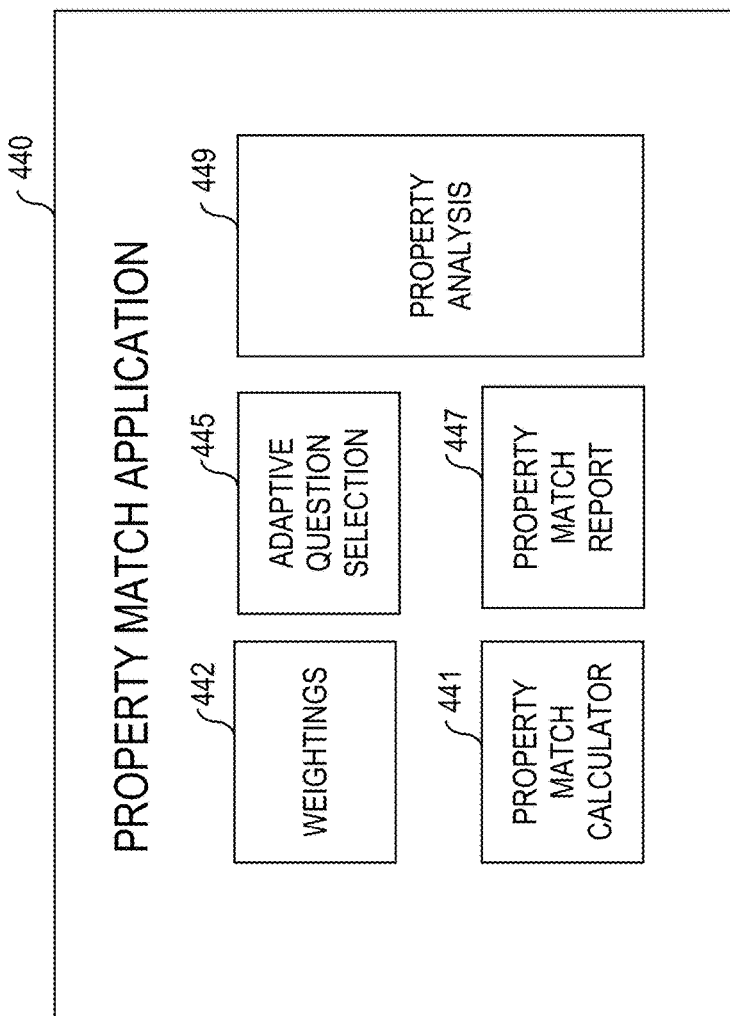
FIG. 12 illustrates an example property match application 440, in accordance with an embodiment of the invention.

FIG. 12 illustrates an example property match application 440, in accordance with an embodiment of the invention. In one embodiment, one of the applications 410 (FIG. 2)

executing/operating on the server devices 210 (FIG. 1) is a property match application 440. The property match application 440 comprises a property match calculator unit 441 configured to determine a property match score for a property of interest to a user based on a personal profile of the user and one or more property attributes maintained in a database 260 for the property. The property match calculator unit 441 combines data from one or more personal profiles for one or more users associated with the property with property data for the property to calculate potential health impact correlations.

In one embodiment, the property match calculator unit 441 determines compatibility between a property and a user by evaluating a personal profile for the user against property data for the property. As described in detail later herein, the property match calculator unit 441 may look for specific triggers of the user, specific exposures of the user and property attributes (e.g., potential exposures associated with the property, such as mold risk index, pet factor, etc.) used in determining a property score for the property. For example, for a property with a high mold risk index, the property will have a substantially lower property match score with respect to a user who has a high sensitivity to biologicals compared to another user with minimal/no sensitivities to biologicals. As another example, for a property with a high pet factor, the property will have a substantially higher property match score with respect to a user who has minimal/no sensitivities to pets compared to another user with a high sensitivity to pets.

In one embodiment, the property match application 440 comprises an adaptive question selection unit 445 for adaptively selecting questions from the collection 264 based on prior user responses to previously presented questions and/or property data for a property associated with the user. If, at any point during the presentation of questions, user responses seem contradictory or mis-entered, the adaptive question selection unit 445 runs a related education module and then repeats or rephrases the target questions. Questions selected and presented to a user are dynamically selected based on prior user interactions (e.g., prior user responses). For example, if prior user responses to initial screening questions indicate that pets are not an issue to a user but biologicals are, the likelihood of biological questions being subsequently selected and presented to the user increases whereas the likelihood of pet questions being subsequently selected and presented to the user decreased.

In one embodiment, the property match application 440 comprises a weightings unit 442. The weightings units 442 comprises, but is not limited to, the following: (a) different weighting values for different attributes, factors or indexes, (b) different prevalence values for different attributes, factors or indexes, and (c) data representing interrelationships between different attributes, factors or indexes.

In one embodiment, the property match application 440 comprises a property match report unit 447 for generating a property match report that includes a property match score for a property of interest to a user. The property match report may include one or more suggested improvements to the property to increase compatibility between the property and the user. The improvements, when undertaken, may help improve the property match score. The property match report may also provide estimated costs associated with the improvements. The estimated costs may be based on contractor fees, fees for past improvement projects, expert judgment, user feedback and other data sources. A property match report may be presented to a user via a website 295.

Table 11 below provides an example property match report generated by the property match application 440.

TABLE 11

70% of properties like this one typically have poor indoor air quality, which results in negative impact on occupant health.
Based on your Match analysis this property will be a grade C match.
Stucco Walls in this climate with signs of landscaping sprinklers hitting the wall on the shaded side of the house have high risk of biological growth inside the wall cavities. Typical cost to repair this kind of problem ranges from $3,000-$20,000. The priority level of this change for someone like you is MEDIUM
This property was built in 1938. The paint around the windows appears to be original. It is highly likely to contain lead paint. Remediation or encapsulation needs to be done. Typical cost in your area is $1,000-$3,000. The priority level of this change for someone like you is HIGH
Properties with basements in this climate negatively impact occupant health 50% of the time. This basement shows signs of moisture intrusion in photo #3. That increases likelihood to 80%. Typical costs to remediate and repair range from $3,000 to $15,000 in your area. The priority level of this change for someone like you is LOW
Cat is living in the house. You indicated you are sensitive to cats. Effective remediation would require painting to encapsulate existing dander on the wall, removal of the carpet, and cleaning the duct work to reduce risk of impact on you. Typical cost in your area is $3,000-5,000. The priority level of this change for someone like you is HIGH
Property is near a freeway and concentrates chemicals and fumes from outside.
Substantive, but not complete remediation would require [insert requirement here]. The priority level of this change for someone like you is HIGH.
Projected cost to improve house to a grade C+ match (high priority items) is around $16,000
Projected cost to improve house to a grade B match (High and medium priority improvements) is $26,000
Projected cost to improve house to a grade B+ match (High, medium and low priority improvements) is $35,000
Grade A and A+ matches are not possible given the properties history and location.
Consider the creating a property match score for others who will live in the dwelling. While the Match grade of the property is improvement by your lack of sensitivity to biological agents, this property would be a very poor match for someone sensitive to biological such as mold.
30% of people with a property match score of C+ report being satisfied with the air quality in their property
50% of people with a property match score of B report being satisfied with the air quality in their property

TABLE 11-continued

65% of people with a property match score of B+ report being satisfied with the air quality in their property
80% of people with a property match score of A report being satisfied with the air quality in their property
95% of people with a property match score of A+ report being satisfied with the air quality in their property In one embodiment, the property match calculator unit 441 is configured to determine a property match score for a property of interest to a group of multiple users (i.e., a collective group) based on a group profile of the group and one or more property attributes maintained in a database 260 for the property. As described above, a group profile for a group of multiple users combines personal profiles of each user of the group. A property match score for a property of interest to a group of multiple users represents compatibility between the property and the group for healthy living.

For example, the property match calculator unit 441 may determine a property match score representing compatibility between a family and a property by evaluating each personal profile of each family member of the family against property data for the property.

In one embodiment, the property match application 440 extracts/determines a property attribute data (e.g., pattern relating to a property attribute) from property data associated with a property area. The property match application 440 combines the property attribute data with at least one other property attribute data to determine presence or movement of a pollutant data (e.g., pattern relating to a pollutant) within the property area. The property match application 440 determines a health sensitivity data (e.g., pattern relating to a sensitivity) from personal data associated with a user. The property match application 440 determines a potential impact data (e.g., pattern relating to personal impact) that the pollutant data may have on health of the user based in part on the health sensitivity data and the combination, and computes a property match score representing compatibility of the property area with the health of the user based in part on the first potential impact data.

In one embodiment, the property match calculator unit 441 determines a property match score based on the following factors: biological match, chemical match, particle match, pet match, total burden and corresponding weighting.

A weighting for a total burden is dynamically determined by based on current total burden of a user and increased/decreased stress that the property would put on health of the user.

Table 12 provided below comprises a listing identifying different parameters referenced in this specification.

TABLE 12

| Abbreviation | Definition |
| --- | --- |
| PropertyMatch_Score | Property match score |
| BiologicalMatch | Match score for biologicals |
| MoldMatch | Match score for mold |
| ChemicalMatch | Match score for chemicals |
| ParticleMatch | Match score for particles |
| PetMatch | Match score for pets |
| TotalBurden | Total burden |
| TotalBurden_Amplification | Amplification factors for total burden |

In one embodiment, the property match calculator unit 441 computes PropertyMatch_Score in accordance with the equation (20) provided below:

$$\text{PropertyMatch\_Score} = [\text{BiologicalMatch} + \text{MoldMatch} + \text{ChemicalMatch} + \text{ParticleMatch} + \text{PetMatch}] \times \text{TotalBurden} \times \text{TotalBurden\_Amplification} \quad (20).$$

In one embodiment, a PropertyMatch_Score is a raw score that is converted to a number grade, a percentage grade, a letter grade, etc. The higher a PropertyMatch_Score computed for a property of interest to a user, the smaller the degree of compatibility between the property and the user (i.e., the property is unsuitable for the user).

In one embodiment, the property match calculator unit 441 computes BiologicalMatch in accordance with the equation (21) provided below:

$$\text{BiologicalMatch} = \text{Biological Sensitivity} \times \text{IBAI} \quad (21).$$

In one embodiment, the property match calculator unit 441 computes MoldMatch in accordance with the equation (22) provided below:

$$\text{MoldMatch} = \text{MoldSensitivity} \times \text{IMI} \quad (22).$$

In one embodiment, the property match calculator unit 441 computes ChemicalMatch in accordance with the equation (23) provided below:

$$\text{ChemicalMatch} = \text{ChemicalSensitivity} \times \text{ICI} \quad (23).$$

In one embodiment, the property match calculator unit 441 computes ParticleMatch in accordance with the equation (24) provided below:

$$\text{ParticleMatch} = \text{ParticleSensitivity} \times \text{IPI} \times \text{IPETI} \quad (24).$$

In one embodiment, the property match calculator unit 441 computes PetMatch in accordance with the equation (25) provided below:

$$\text{PetMatch} = \text{PetSensitivity} \times \text{IPETI} \quad (25).$$

In one embodiment, the property match application 440 comprises a property analysis unit 449. In one example implementation, the property analysis unit 449 functions as a geographic region/multiple properties analysis tool for determining potential health issues associated with a particular geographical area.

In another example implementation, the property analysis unit 449 functions as a property default risk calculator tool for predicting, based in part on group profiles for regional populations, regional and individual risks of property default, based on property, banking and mortgage data. If a property match score indicates that a property of interest to a user is compatible with the user, a bank is more likely to provide a loan to the user for use in purchasing the property.

Figure 13:
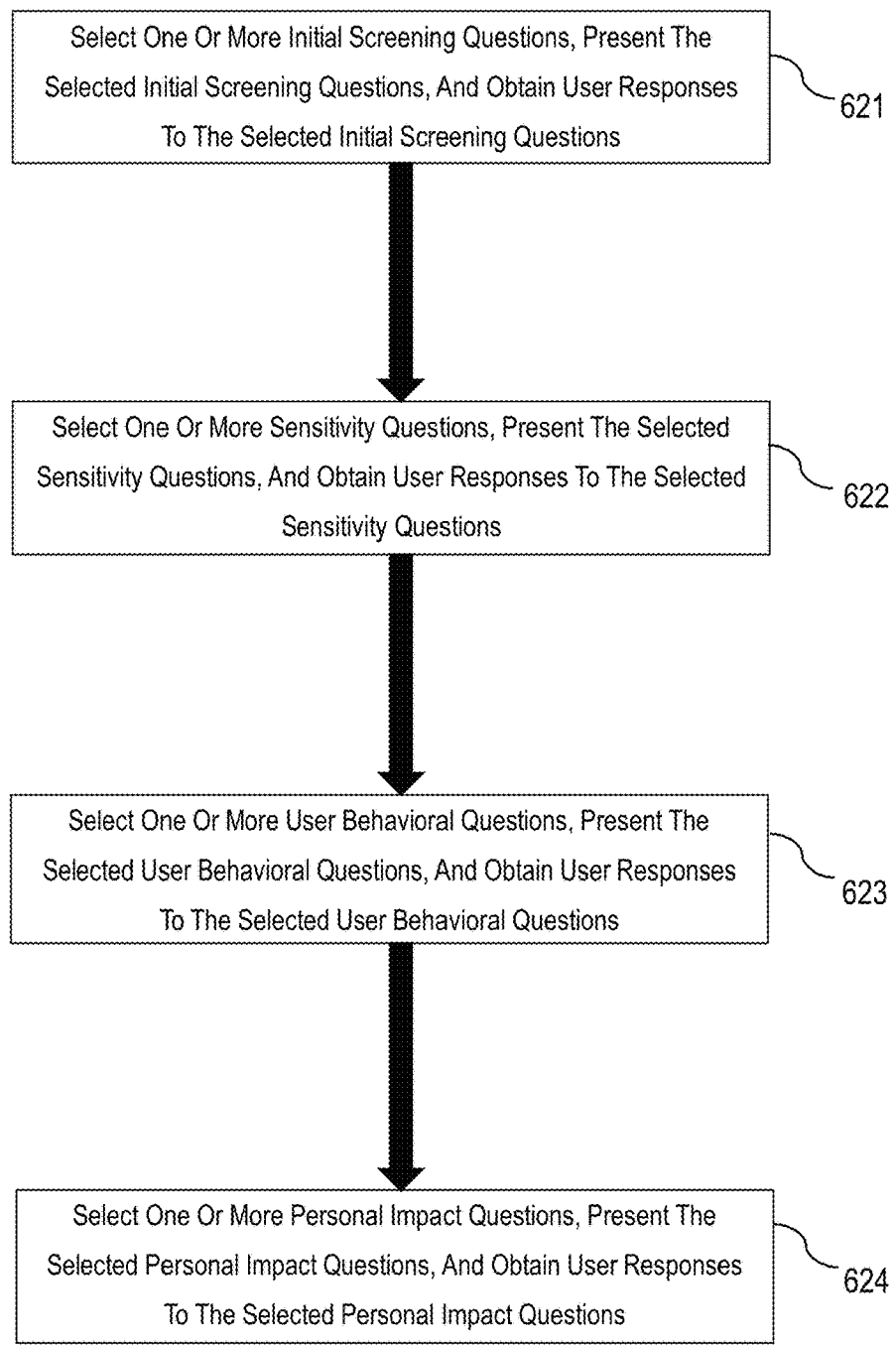
FIG. 13 illustrates an example process 620 for obtaining information used in determining a property match score, in accordance with an embodiment of the invention.

FIG. 13 illustrates an example process 620 for obtaining information used in determining a property match score, in accordance with an embodiment of the invention. In process block 621, select one or more initial screening questions, present the selected initial screening questions, and obtain user responses to the selected initial screening questions. In one embodiment, the selected initial screening questions are selected from a question bank 265F (FIG. 4).

In process block 622, select one or more sensitivity questions, present the selected sensitivity questions, and obtain user responses to the selected sensitivity questions. In one embodiment, the selected sensitivity questions are selected from a question bank 265H (FIG. 4).

In process block 623, select one or more user behavioral questions, present the selected user behavioral questions, and obtain user responses to the selected user behavioral questions. In one embodiment, the selected user behavioral questions are selected from a question bank 265D (FIG. 3).

In process block 624, select one or more personal impact questions, present the selected personal impact questions, and obtain user responses to the selected personal impact questions. In one embodiment, the selected personal impact questions are selected from a question bank 265K (FIG. 4).

The order of process blocks 621-624 may change; any one of the process blocks may lead to any other one of the process blocks.

Figure 14:
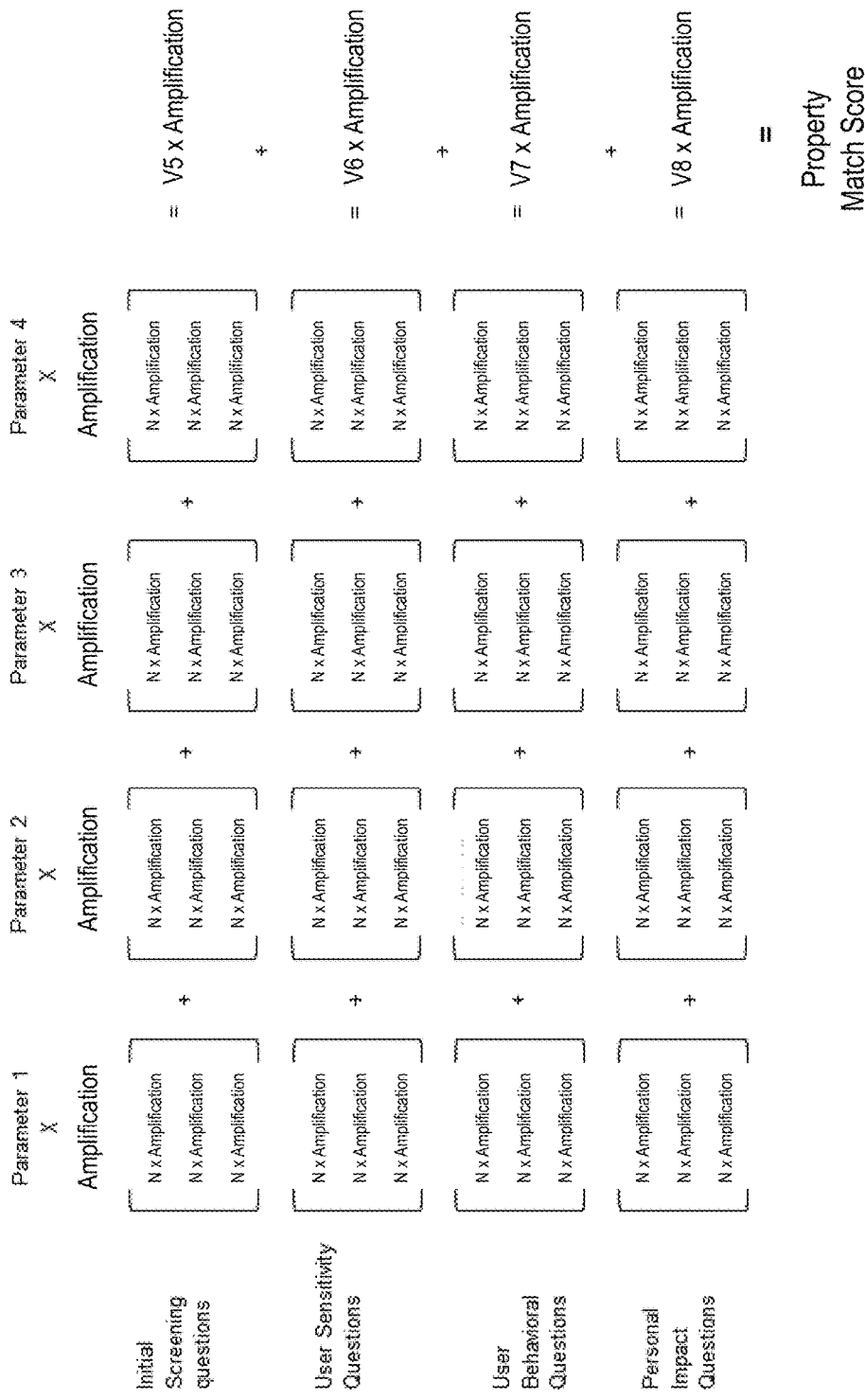
FIG. 14 illustrates an example algorithm 443 applied by the property match calculator unit 441 to determine a property match score, in accordance with an embodiment of the invention.

FIG. 14 illustrates an example algorithm 443 applied by the property match calculator unit 441 to determine a property match score, in accordance with an embodiment of the invention. The property match calculator unit 443 computes a property match score based on user responses to different subsets of questions selected from the collection 264, such as a first subset of initial screening questions selected from the question bank 265F, a second subset of sensitivity questions selected from the question bank 265H, a third subset of user behavioral questions selected from the question bank 265D, and a fourth subset of personal impact questions selected from the question bank 265K.

For each subset, one or more questions N of the subset are assigned an amplification factor. The value of each question N may differ based on potential impact (i.e., severity) that the question N has in influencing an overall value of a parameter corresponding to a pollutant. A value may be defined for each question N, and the question N may be factored into the calculation of more than one parameter (i.e., may be factored into the calculation of different parameters for different pollutant s). For example, for each parameter (e.g., Parameter 1, Parameter 2, Parameter 3, Parameter 4), the value of each question N factored into the calculation of the parameter is summed. The overall value of each parameter is then summated as a value V for the subset (e.g., V5 for the first subset, V6 for the second subset, V7 for the third subset, V8 for the fourth subset), and the value V is applied an amplification factor representing the potential impact (i.e., severity) of the subset on the health of a mean population demographic. Furthermore, the overall value of each parameter may be amplified on a pollutant basis such that the overall value of any one parameter corresponding to a pollutant does not overly influence the property score. Finally, each amplified value V is summated, and the resulting sum represents the property match score.

The number of parameters may be variable.

Property Health Advice Application

Figure 15:
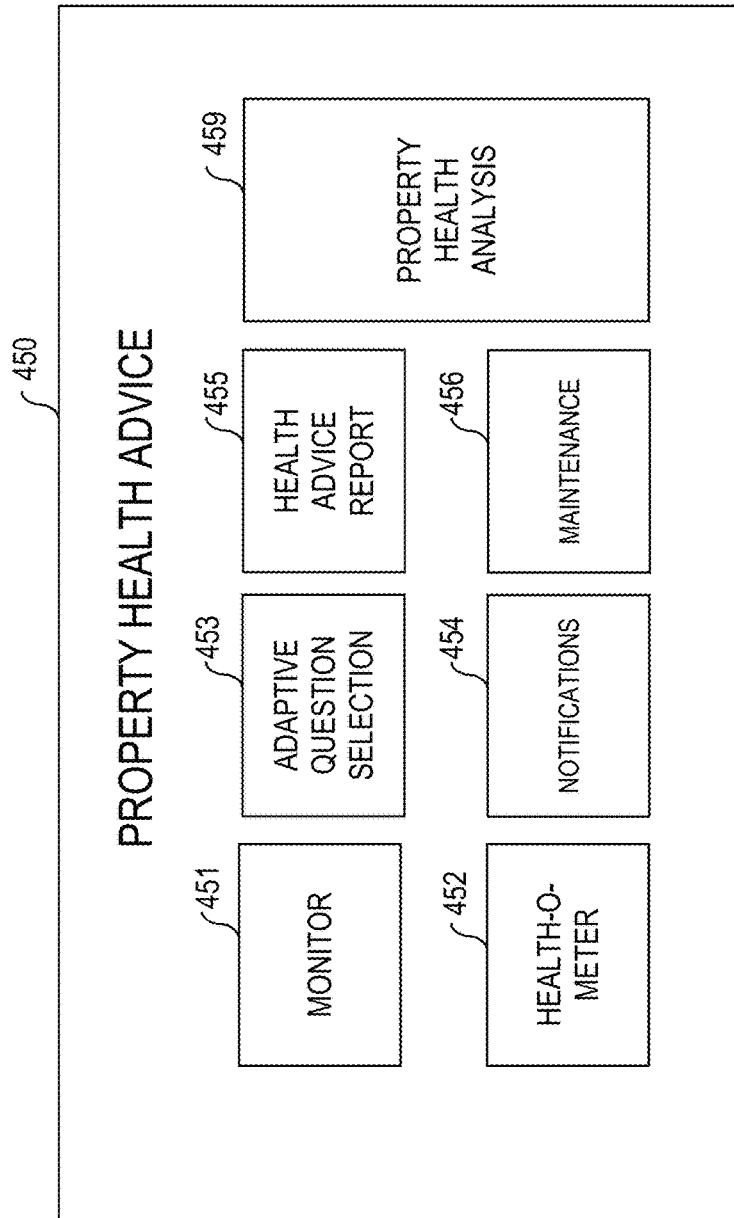
FIG. 15 illustrates an example property health advice application 450, in accordance with an embodiment of the invention.

FIG. 15 illustrates an example property health advice application 450, in accordance with an embodiment of the invention. In one embodiment, one of the applications 410 (FIG. 2) executing/operating on the server devices 210 (FIG. 1) is a property health advice application 450. Approximately 35% of illnesses are attributable to airborne pollutants that swirl around in the air inside properties.

The property health advice application 450 may be used to model an indoor environment to predict changing health conditions. The property health advice application 450 is configured to model an ecosystem within an indoor air environment of a property to predict when conditions within the property become detrimental to human health.

The property health advice application 450 provides property health advice in real-time on how a user may interact with the ecosystem of the property for better health, such as providing recommended actions for the user to take to reduce impact on his/her health. For example, the property health advice may comprise user behavioral advice including suggested remediation actions and/or interventions for a user to take with respect to the property to reduce impact on his/her health.

The property health advice application 450 predicts when the ecosystem of the property changes in ways that stress human health, such as when pollutants harbored within places like wall cavities, crawlspaces, attics and other interstitial spaces and carpets become more active which in turn puts pressure on an occupant's health. The ecosystem of the property represents the biology of the property; when the biology of the property changes, occupants of the property may get sick. The property health advice application 450 predicts when the biology of the property changes and how a user may intervene.

The property health advice application 450 comprises a health-o-meter unit 452 configured to analyze property attributes of a property and effects of the local climate and outdoor air on the property. To improve the analysis, a user may be presented with questions selected from the collection 264 (e.g., property attributes questions and sensitivity questions). The property health advice application 450 comprises an adaptive question selection unit 453 for adaptively selecting questions from the collection 264. The property health advice application 450 may also draw on factors/indexes used in determining a property score and a property match score.

The property health advice application 450 comprises a monitor unit 451 for monitoring local climatic changes to predict daily and hourly changes in the indoor environment that could lead to stress (impact) on the user's health. The health-o-meter unit 452 then provides, in real-time, health advice that suggest actions and/or interventions for the user to take that will lead to reductions of pollutants within the property as the weather or climatic conditions change. The user may be to provide user feedback on the outcome of the actions and/or interventions. The user feedback will be used to further refine and improve the intelligence of the health-o-meter unit 452. Users can track the actions that they have taken and see those collected in reports and graphs. The user may pull up a report with graphs and data on the intervention actions they have taken to date, the projected impact and their self-reported impact to track their actions over time. This graph should also contain any larger remediation actions they have done (remodeling, changing air ducts, removing carpeting, etc.) that have been completed, i.e., any actions recommended in a score or match report. Users can now visualize the impact of their actions over time. The sense of accomplishment encourages them to continue on.

The health-o-meter unit 452 may also provide preventative advice in advance of climatic cycles, advice to manage risk during cycles, and how to monitor for as well as ward off new problems that could develop after the cycle is complete. The health-o-meter unit 452 may also provide seasonal tips.

In one embodiment, the property health advice application 450 comprises a health advice report unit 455 for generating a health advice report that includes customized health advice for a user. A health advice report may be presented to a user via a website 295.

The property health advice application 450 comprises a notifications unit 454 configured to send notifications of health advice through text, email or any other electronic method depending on user preference and urgency of the health advice. Users can delay or set reminders for actions, following notifications. They can also report whether they did the action through a number of methods, including directs responses to notifications.

In one embodiment, the health-o-meter unit 452 provides health advice based in part on health events reported by a user. The application 450 may also interface with a health app that is already tracking health events of the user. These health events will be correlated to further personalize health advice. The health-o-meter unit 452 will map both cycles effecting the ecosystem of the property along with user reported health events and vital statistics.

The property health advice application 450 comprises a maintenance unit 456 configured to track when property health related maintenance routines/tasks needs to be performed, such as replacing filters on HVAC, air purifiers, water filters, duct cleaning, etc. The maintenance unit 456 will have the capacity to prompt a user for when other property health related maintenance routines/tasks needs to be performed, like changing the filters on the vacuum.

In one embodiment, the property health advice application 450 extracts/determines a property attribute data (e.g., pattern relating to a property attribute) from property data associated with a property area. The property health advice application 450 combines the property attribute data with at least one other property attribute data to determine presence or movement of a pollutant data (e.g., pattern relating to a pollutant) within the property area. The property health advice application 450 monitors environmental context of the property area and detects a change affecting the environmental context of the property area. If the property health advice application 450 detects a change that impacts the presence or the movement of the pollutant data within the property area, the property health advice application 450 provides a recommendation for reducing the impact of the detected change.

Table 13 below provides an example health advice report generated by the property health advice application 450 in response to real-time changes in climate.

TABLE 13

| Sample Real Time Climatic Advice |
| --- |
| Climatic conditions have shifted causing the ecosystem in your house to stress your system. We recommend opening a few windows in each room to mildly flush the house with fresh outdoor air. |
| Outdoor climatic conditions have high pollution and pollen. Based on your reported sensitivities we recommend keeping your doors and windows closed and filtering your air either by running your forced air in ventilation mode providing it has a MERV 13 filter or better installed and/or running your air purifiers. |
| Climatic conditions have shifted suddenly and forcefully. Open all doors and windows for an aggressive flush for one hour. Best to leave the property during this hour to clear the air. |
| Families with properties like yours in these kind of climatic shifts report nasal congestion 60% of the time which leads to sinus infections 40% of the time. Families who intervene by flushing the air report no adverse health effect 90% of the time. |

Table 14 below provides an example sequence of notifications generated and sent by the property health advice application 450 over time in response to real-time changes in weather.

TABLE 14

| Weather Event Advice |
| --- |
| Preemptory [First notification sent in advance of upcoming weather event] |
| Heavy Rains are coming. Insure your gutters are clean, drains around the property are unobstructed and the roof is clean. |
| Concurrent [Second notification generated and sent during the weather event] |
| Rains have subsided. Be aware of wet spots in the house. Look into your crawlspace to insure there is no standing water. |
| Post Event [Third notification generated and sent after the weather event] |
| It is now a day later, be weary of any wet damp odors. Those will indicate leaks within the walls, roof or floor that will likely lead to biological growth. If these are cleaned up and dried within 24 hours you will avert health threats and expensive cleanup after the fact. |

In one embodiment, the property health advice application 450 comprises a property health analysis unit 459. In one example implementation, the property health analysis unit 459 functions as a population health analysis tool for providing health maps, suggestions and insights for hospital, governments, insurance agencies and other entities. The population health analysis tool may be used to predict issues, such as flu outbreaks, pest infestations, magnitude of population level health issues, etc.

In another example implementation, the property health analysis unit 459 functions as a disaster response planner tool for assisting disaster relief organizations and agencies, such as FEMA and the Red Cross, in predicting and responding to disaster-related events, such as floods.

Health Insurance Correlation Application

Figure 16:
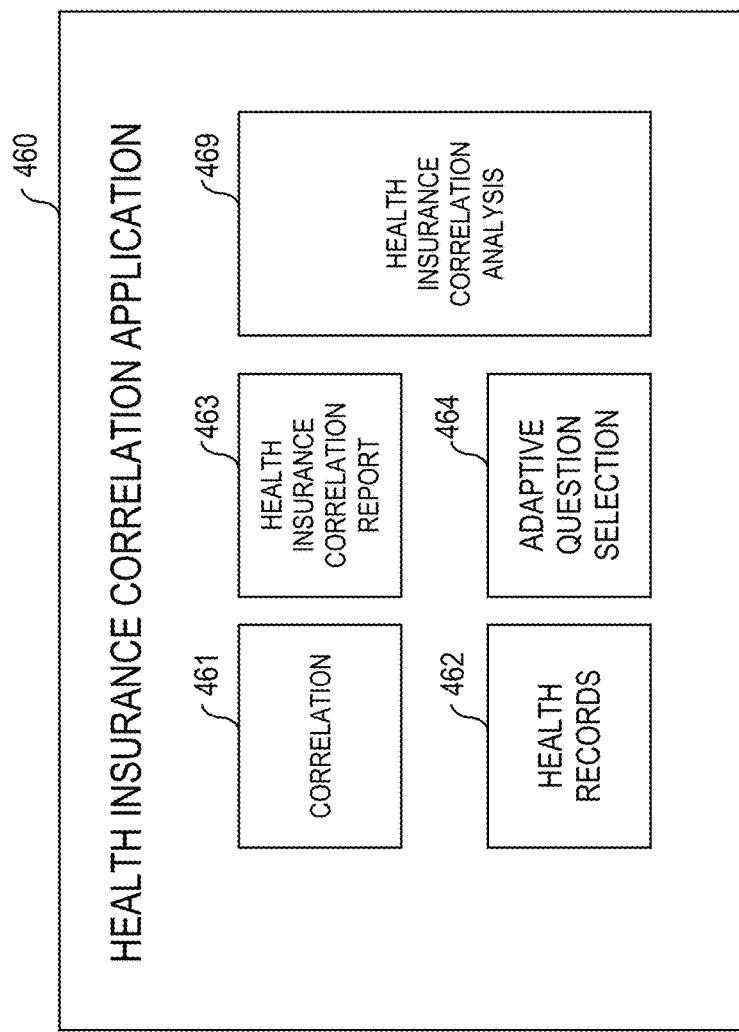
FIG. 16 illustrates an example health insurance correlation application 460, in accordance with an embodiment of the invention.

FIG. 16 illustrates an example health insurance correlation application 460, in accordance with an embodiment of the invention. In one embodiment, one of the applications 410 (FIG. 2) executing/operating on the server devices 210 (FIG. 1) is a health advice application 460. Approximately 35% of illnesses are attributable to airborne pollutants that swirl around in the air inside properties. The health insurance correlation application 460 comprises a correlation unit 461 and a health records unit 462 that may be used at the direction of health insurance companies to process and correlate thousands of health insurance records with property attributes of insured record holders in order to predict patterns of disease and symptomology that are a probable result of a property of an insured record holder.

In one embodiment, the health insurance correlation application 460 may implement certain firewalls to maintain HIPPA confidentiality.

In one embodiment, the correlation unit 461 will correlate disease codes in each health insurance record with the analytics implemented by the property score application 420 based on public data for properties occupied by insured record holders.

To improve the analysis, an insured record holder may be presented with questions selected from the collection 264 (e.g., property attributes questions and sensitivity questions). Insurance companies have the option to request that insured record holders respond to sensitivity and user behavior questions, allowing individualization of intervention strategies and projected costs. The health insurance correlation application 460 comprises an adaptive question selection unit 464 for adaptively selecting questions from the collection 264. For example, if the property is a school, students of the school may be asked to rate indoor air quality of the school and other questions to determine the attributes and climatic conditions affecting the school. Image data of the school may also be obtained to improve the analysis. The accuracy of the data may also be improved when an insured record holder submits DNA, micro biome or blood test data to be analyzed.

If indoor exposures are indicated as probable/correlated cause of disease and symptomology pattern, but the insured record holder's property does not appear to be high risk, the record holder's place of work, school or other dominant place where he/she spends significant time may be analyzed next using the health insurance correlation application 460.

In one embodiment, the correlation unit 461 uses machine learning to extract, collate, and analyze data from personal profiles, property scores, and health insurance records to identify correlations among disease codes, medical symptoms, medical histories and conditions of current (or prior) properties. The correlation unit 461 searches for possible correlations for a particular insured record holder starting from elements that have the highest known correlation with diseases and disease codes. The correlation unit 461 evaluates correlations which include, but are not limited to, the following: (1) disease codes and history to personal susceptibility for exposure to biologicals, chemicals, pets, and particles, (2) symptomology history and prescriptions to amplification factors over time (such as windy or humid climates), and (3) correlation between total burden on the insured record holder and cost of health insurance claims over the next year.

For example, the correlation unit 461 may determine that asthma attacks for children occupying a property have a 65% correlation to start within 2 weeks from the start of biological activity in the property resulting from leaks, water events and cold fronts. As another example, the correlation unit 461 may determine that pollen seasons have a 90% correlation with decreased compliance in an insured record holder taking medications as prescribed. As another example, the correlation unit 461 may determine that an insured record holder is 10 points away from moving to the next level on the total burden scale and their total burden has recently risen; those who move up to this level on the total burden scale typically cost $20K more per year in health insurance claims than those who remain at their current level (70% correlation).

In one embodiment, correlations determined by the correlation unit 461 may be used to refine a property score, a property match score, a personal profile and personal action plan, etc.

In one embodiment, the health insurance correlation application 460 comprises a health insurance correlation report unit 463 for generating a health insurance correlation report. A health insurance correlation report may be presented to an insurance company via a website 295. The health insurance correlation report may include a cost range of proposed interventions so that the insurance company can correlate this potential remedy with their actuary tables on the cost to insure. Additionally, the insurance company can provide the insured record holder the correlation and intervention cost so that the insured record holder can make a decision as to whether the cost is a worthy expense to improve his/her quality of life. The website 295 may include a web portal to certified contractors who can perform the recommend interventions.

In one embodiment, the health insurance correlation application 460 extracts/determines a property attribute data (e.g., pattern relating to a property attribute) from property data associated with a property area. The property health advice application 450 combines the property attribute data with at least one other property attribute data to determine presence or movement of a pollutant data (e.g., pattern relating to a pollutant) within the property area. The health insurance correlation application 460 determines a potential impact data (e.g., pattern relating to personal impact) that the pollutant data may have on individual health based in part on the combination, collects a health record of a user associated with the property, and determines a correlation between the health record and the potential impact data.

Table 15 below provides an example health insurance correlation report generated by the health insurance correlation application 460.

TABLE 15

Asthma

Insured has been to the emergency room 3 times this year for asthma attacks. Insured's property has a property score of 62 and combination of property attributes that correlate with asthma attacks 78% of the time.
Recommendation: Insured responds to questions (e.g., personal sensitivity questions) to improve probability of correlation.
Follow-up report [Generated in response to the insured responding to questions]:

The following interventions [list of suggested actions provided] in properties with this pattern of property attributes and climate have reduced emergency room visits for 68% of insured individuals with disease and symptomology patterns like yours.

Table 16 below provides another example health insurance correlation report generated by the health insurance correlation application 460.

TABLE 16

Chronic Sinus Infections

Insured has a history of chronic sinus infections. Insured's property has a property score of 50 with a high mold risk index for the property. Additionally, the timing of infection correlates with local weather patterns that lead to fungal activity within properties in this climate. These patterns correlate with 80% likelihood that many of these sinus infections are caused by the property.
Recommendation: Insured responds to questions (e.g., personal sensitivity and symptoms questions) to improve probability of correlation.
Follow-up report [Generated in response to the insured responding to questions]:

The following interventions [list of suggested actions provided] has reduced pattern of sinus infections by 60% within patients with these characteristics 80% of the time.

In one embodiment, the health insurance correlation application 460 comprises a health insurance correlation analysis unit 469. In one example implementation, the health insurance correlation analysis unit 469 functions as a geographic region/multiple properties analysis tool for determining potential health issues associated with a particular geographical area.

In another example implementation, the health insurance correlation analysis unit 469 functions as a health insurance coverage assessor tool for predicting cost of insuring groups with particular types of properties.

Figure 17:
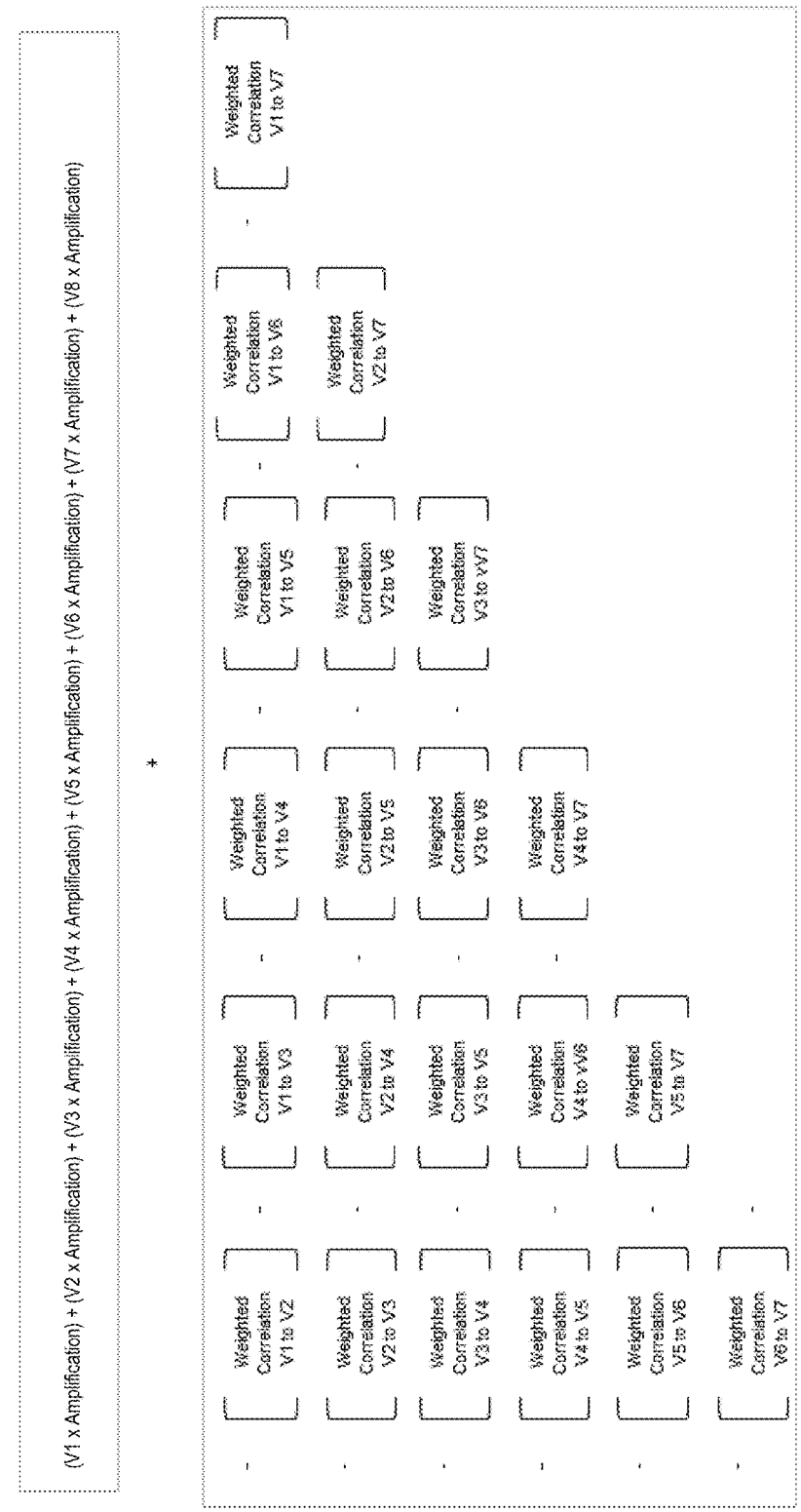
FIG. 17 illustrates an example algorithm 465 applied by the correlation unit 461 to determine health insurance correlations, in accordance with an embodiment of the invention.

FIG. 17 illustrates an example algorithm 465 applied by the correlation unit 461 to determine health insurance correlations, in accordance with an embodiment of the invention. The algorithm 465 includes variables determined using algorithms 425 and 443, as described above.

Crowdsourcing Application

Figure 18:
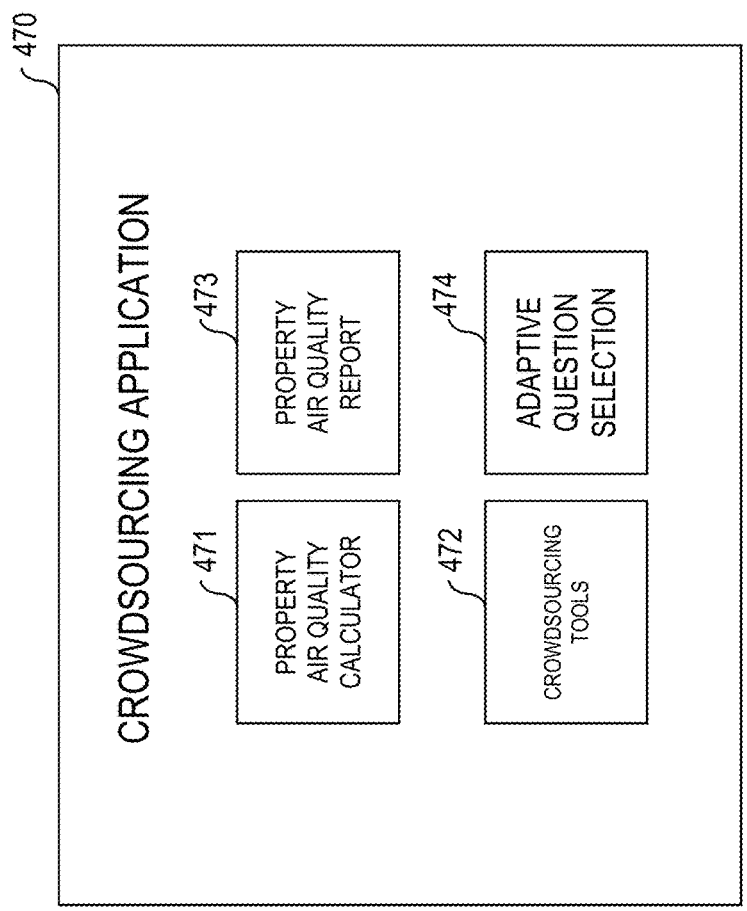
FIG. 18 illustrates an example crowdsourcing application 470, in accordance with an embodiment of the invention.

FIG. 18 illustrates an example crowdsourcing application 470, in accordance with an embodiment of the invention. In one embodiment, one of the applications 410 (FIG. 2) executing/operating on the server devices 210 (FIG. 1) is a crowdsourcing application 470. The crowdsourcing application 470 comprises crowdsourcing tools 472 for crowdsourcing information associated with a property (e.g., commercial and public buildings such as hotels, restaurants, schools, gyms, offices, theaters, apartments, and churches) from a community of users. The crowdsourcing tools 472 includes one or more virtual tools through which one or more users may provide user feedback (e.g., ratings or scores) relating to air quality of the property. The crowdsourcing tools 472 may provide the user provided input for public viewing via a website 295. Users may visit the website 295 to provide user feedback about a particular property and/or view user feedback submitted by other users. This enables a user to factor into user feedback from other users when determining whether or not to frequent/visit the property. The users may be business travelers, parents, school children, teachers, office and service workers, restaurant patrons, etc.

In one embodiment, the website 295 includes a score submission webpage for receiving user feedback from users. The score submission webpage comprises a graphical user interface (GUI) that includes a submission form for users to rate air quality of a particular property on a predetermined scale. For example, a user may rate the air quality on a scale of 1 star to 5 stars, wherein 1 star represents a lowest degree of air quality (i.e., the air quality is dirty and/or harmful), and wherein 5 stars represents a highest degree of quality (i.e., the air quality is clean). The score submission webpage may also prompt a user to describe how the property makes them feel, and include an input text box that the user may use to enter qualitative comments relating to the property. Users may also submit photos and/or videos of the property.

The crowdsourcing application 470 comprises a property air quality calculator unit 471 for determining a property score for air quality of a property based on user feedback received, via the website 295, from one or more users, climate data about the environment around the property, and/or public data about the property and its construction. The property score determined may be displayed on the website 295 together with some of the user feedback received. In one embodiment, the website 295 provides a summary of the input feedback received, and presents the summary with top insights and highlights indicating the most frequently mentioned feelings, complaints, or positives associated with the air quality of the property.

The crowdsourcing tools 472 includes one or more tools configured to suggest improvements to an owner of the property. For example, an owner operating a business on a particular property that has received input feedback may visit the website, and, upon indicating that the owner is associated with the property, submit additional information relating to the property. Based on the additional information submitted and the property score, the crowdsourcing system may provide one or more recommendations for improving the air quality of the property, costs estimates and return-on-investment (ROI) estimates for the improvements. Improving the air quality of the property based on the recommendations suggested may help improve customer experience of the business and revenues of the business.

To improve the analysis, users may be presented with questions selected from the collection 264 (e.g., property attributes questions and sensitivity questions). The crowdsourcing application 470 comprises an adaptive question selection unit 474 for adaptively selecting questions from the collection 264. For example, additional information related to the property may be obtained from an owner operating a business on the property by presenting one or more property attributes questions to the owner.

In one embodiment, the crowdsourcing application 470 comprises a property air quality report unit 473 for generating a property air quality report. The property air quality report may include one or more recommendations for improving the air quality of the property, costs estimates and return-on-investment (ROI) estimates for the improvements. A recommendation may be a suggested intervention or a suggested action that the owner may take to improve the air quality of the property. The property air quality report may also include, if available, an estimated impact each recommendation has on the property score of the property, as well as impacts on the customer/user experience and business revenue. The reports and recommendations are based on correlations between property attributes of the property, input feedback received, environmental factors and results of past interventions that the owner had taken.

Table 17 below provides an example property air quality report generated by the crowdsourcing application 470.

TABLE 17

Building has a commonly reported musty smell and a rating of 63 out of 100. This is in the bottom 40% of buildings. Based on the feelings of fatigue and sinus congestion reported by users, images of moldy basement, high frequency of water leaks in the building and past flooding in the area, there is a . . . % likelihood that there is moldy air circulating throughout the building - not just the basement. Typically, this issue leads to a drop in a building air quality score by . . . points and has a 80% correlation with 25% lower foot traffic through the building. Around 30% of the population is sensitive to damp, wet building exposure and may experience the following symptoms while in the building - uncomfortable with odors, loss of motivation, congestion, burning eyes, mild stomach pain, foggy thinking.
Here are interventions that can be taken to address the issues with a typical cost range for the intervention and the improvements that were seen by the building
In your area, previous owners who have employed contractors to intervene have rated the contractors as follows . . .

In one embodiment, the crowdsourcing tools 472 provides a collective action platform that facilitates collaboration among a community of users with regards to improving air quality of a property, such that an owner of a business being operated on the property is not the only one with a say with regards to improvement. The collective action platform, for example, may be utilized by a community of users attending a particular school, a particular office, or a particular library. The community of users may come together to advocate for one or more changes in improving the air quality of the property. The web site may provide a suite of collaboration tools, such as a discussion forum where different users can post comments and discuss issues relating to the property, form message threads for sharing tips relating to the property, and upload videos and/or photos related to the property.

On the discussion forum, users may also create and support different causes for specific improvements to the property that users care about. Users may help group organize, advocate for changes or contribute funding to a cause. A user may contribute to funds for a cause using a third-party site, such as Kickstarter or a trusted financial partner.

In one embodiment, the crowdsourcing tools 472 can allow users of the community to indicate who their health insurance carrier/provider is, such that the crowdsourcing tools 472 can determine how many users have health insurance with the same carrier/provider, and provide the carrier/provider with an estimate of total health costs incurred as a result of the air quality of the property.

The collective action platform may provide resource tools, such as articles, website links, scientific studies and an advocacy tool kit with literature, best practices for change, and cases studies that show the ROI, cost and impact of past building interventions. The resource tools may include a webpage listing different partnerships (e.g., a health department, insurance companies, etc.) that help advocate for change. If an insurance company observes a high prevalence of sinus infections by users at a particular property (e.g., a school), the insurance company may become an ally in funding or supporting changes at the property for improving air quality at the property.

In one embodiment, a user of the discussion forum may be assigned the role of a community manager. The community manager monitors forum discussions and comments, and may collaborate with causes or set up contacts between partners and community groups, as appropriate.

Contractor Recommendation Application

Figure 19:
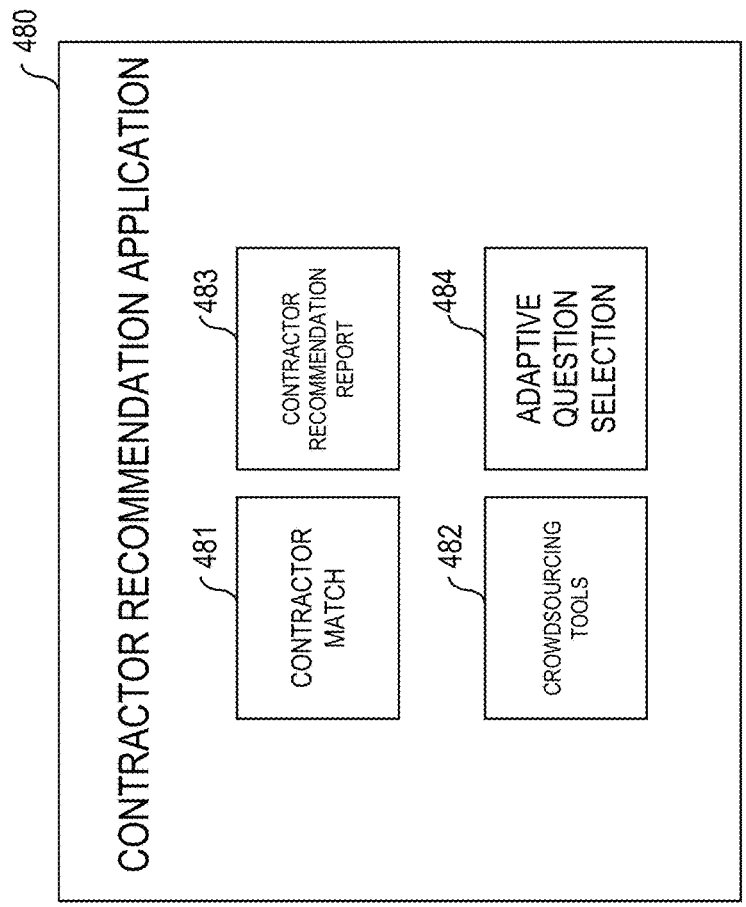
FIG. 19 illustrates an example contractor recommendation application 480, in accordance with an embodiment of the invention.

FIG. 19 illustrates an example contractor recommendation application 480, in accordance with an embodiment of the invention. In one embodiment, one of the applications 410 (FIG. 2) executing/operating on the server devices 210 (FIG. 1) is a contractor recommendation application 480. The contractor recommendation application 480 comprises crowdsourcing tools 482 including a web portal for contractor referrals. The web portal may also receive user feedback relating to different contractors from owners who have engaged the contractors' services. For example, an owner may rate and/or comment on service quality of a contractor, and other owners may review the rating and/or comment provided. Business owners who want access to contractors others than those specifically recommended to them can search a certified contractor database by location, contractor rating, contractor popularity, intervention options offered, price and more. Users may list the contractors they used in their area to perform work and submit what they paid as well as their satisfaction with the services performed. The web portal provides a contractor referral network and collects a compilation of market prices as provided by users selfreporting costs. The contractor recommendation application 480 also maintains a database of different certified contractors.

The contractor recommendation application 480 comprises a contractor match unit 481 configured to, based on a location of a property and information identifying specific interventions or actions needed to improve the property and budget, time, or other constraints and preferences of the user (e.g., price preferences), generate recommendations identifying contractors that can perform the interventions or actions identified within the budget constraints. To improve the analysis, users may be presented with questions selected from the collection 264 (e.g., property attributes questions and sensitivity questions). The contractor recommendation application 480 comprises an adaptive question selection unit 484 for adaptively selecting questions from the collection 264.

The contractor recommendation application 480 comprises a contractor recommendation report unit 483 for generating a contractor recommendation report including recommendations identifying contractors that can perform interventions or actions within particular budget constraints.

Virtual Inspection Application

Figure 20:
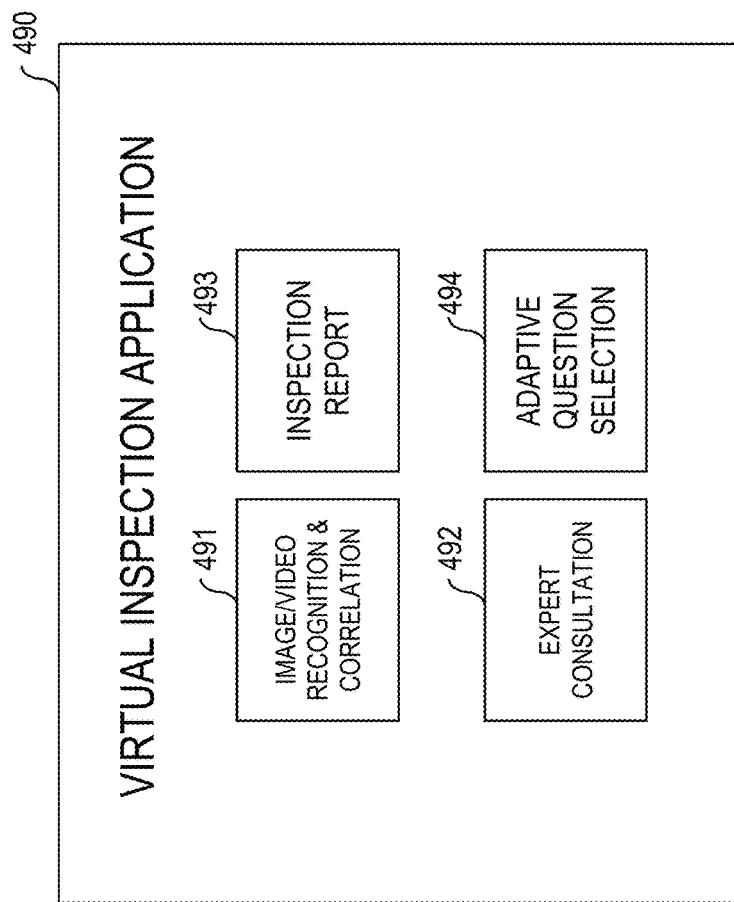
FIG. 20 illustrates an example virtual inspection application 490, in accordance with an embodiment of the invention.

FIG. 20 illustrates an example virtual inspection application 490, in accordance with an embodiment of the invention. In one embodiment, one of the applications 410 (FIG. 2) executing/operating on the server devices 210 (FIG. 1) is a virtual inspection application 490. The virtual inspection application 490 provides a standardized set of instructions for capturing images/videos (e.g., photographs) of physical attributes of a property to facilitate a virtual inspection or user inspection (guided based on the instructions) of the property.

The images/videos captured may be used to determine property information relating to the property, such as key physical attributes, proximity, and environmental context information. The virtual inspection application 490 may generate a custom set of instructions for capturing images/videos of particular areas of interest of the property, wherein the areas of interest are based on the property information and/or other sources of information relating to the property (e.g., property score, personal profile, health insurance information, etc.). The areas of interest may represent suspected high risk areas, such as areas that are likely to affect health of an occupant of the property.

An example area of interest may include an area of the property where water staining or warping of walls and/or flooring is detected, indicating water damage and/or dampness indoors. Water damage and/or dampness indoors is likely to affect occupants who are sensitive to biological amplification, including mold growth.

Another example area of interest may include an area of the property where dust and/or debris is visible (e.g., on carpets), air filters, and air ducts. Accumulation of a particulate (typically composed of multiple, complex substances), is likely to affect occupants with heightened sensitivity/reactivity to dust, pollen, pet dander, and other irritants and asthmagens.

In one embodiment of the invention, a property score determined by the property score application 420 may be used to identify areas of interest in the property. The areas of interest may include areas of the property with sources of exposure to pollutants, such as attic, basement, fireplace, crawlspace, water features, and external sources of pollutants such as restaurants, factories, highways, dry cleaners, in close proximity to the property. For example, an attic with visible water damage or a crawlspace where the HVAC is located could pose substantial risk for susceptible individuals. As another example, a property located within proximity and downwind of a dry cleaning business could be at risk for an individual who is chemically intolerant.

In one embodiment of the invention, health insurance data for one or more occupants of a property may be used to identify areas of interest in the property. The health insurance data may include information identifying reported illnesses, syndromes and health sensitivities/reactivities of the occupants. Based on the health insurance data, areas of interest may include areas and conditions of the property that are likely to contribute to the reported illnesses, syndromes, and health sensitivities/reactivities of the occupants.

The virtual inspection application 490 comprises an adaptive question selection unit 494 for adaptively selecting questions from the collection 264.

In one embodiment of the invention, a personal profile for one or more occupants of a property may be used to identify areas of interest in the property.

For example, if health insurance data for an occupant of the property indicates that the occupant has asthma and sinus infections that correlate with windy days and pollen, the photo-based inspection system may provide an additional set of instructions for capturing additional images of sealants around windows and/or doors of the property. The condition of sealants around windows and/or doors of the property may suggest how "leaky" the property is and may amplify the impact that wind in the area of the property may have on the occupant.

The virtual inspection application 490 comprises an image/video recognition and correlation unit 491. Using a machine learning algorithm, the image/video recognition and correlation unit 491 learns over time, which images/videos captured are most likely to correlate with recommendations that an expert adjusts for a personal action plan or a property match score. The image/video recognition and correlation unit 491 can, over time, learn which images/videos are most likely to have an impact on recommendations, such that instructions for capturing images that have the highest likelihood of impacting recommendations are requested.

The virtual inspection application 490 may request additional images/videos capturing unusual property features or systems, areas suspected by the occupants of involvement with their experience, areas based on expert judgment, areas previously fixed that indicate past problems inadequately addressed, occupant behaviors that may alter the conditions of the indoor environment.

In one embodiment, a property score for a property and/or recommendations for improving the property score may be refined using images requested by the virtual inspection application 490. For example, the virtual inspection application 490 may provide a set of instructions, via a website 295 accessible to the user, for capturing images and/or video of interior and/or exterior areas of the property.

In one embodiment, the virtual inspection application 490 comprises an expert consultation unit 492 that allows one or more consultation experts to make observations regarding physical attributes of the property based on the images and/or videos captured. A consultation expert may be a trained in-house specialist. The expert consultation unit 492 may also facilitate live consultation between a user and a consultation expert. The consultation may be pre-arranged for a pre-determined fee (e.g., an hourly rate).

The virtual inspection application 490 comprises an inspection report unit 493 for generating an inspection report including recommendations. In one embodiment, an inspection report is provided in exchange for a fee paid by the user.

In one embodiment, the virtual inspection application 490 identifies an area of interest of a property area based on property data associated with the property area. The area of interest identified represents a potential area of the property area that may negatively impact health of a user. The virtual inspection application 490 provides the user an instruction for capturing image data relating to the area of interest identified, receiving the image data from the user, and extracts/determines a property attribute data (i.e., pattern relating to a property attribute) from the image data. The virtual inspection application 490 combines the property attribute data with at least one other property attribute data to determine presence or movement of a pollutant data (e.g., pattern relating to a pollutant) within the property area.

Table 18 below provides an example inspection report generated by the virtual inspection application 490.

TABLE 18

Sample Buyer Report:
80% of properties like this typically have poor indoor air quality, a condition that results in negative impact on occupant health.
Stucco Walls in this climate with signs of landscaping sprinklers hitting the wall on the shaded side of the house have high risk of biological growth inside the wall cavities. The two northeastern walls shown in this picture should be investigated. Typical cost to repair this kind of problem ranges from $3,000-$20,000.
This property was built in 1938. The paint around the windows appears to be original. It is highly likely to contain lead paint. Remediation or encapsulation needs to be done. Typical cost in your area is $1,000-$3,000.
Properties with basements in this climate negatively impact occupant health 50% of the time. This basement shows signs of moisture intrusion in photo #3. That increases likelihood to 80%. Typical costs to remediate and repair range from $3,000 to $15,000 in your area
Cat is living in the house. You indicated you are sensitive to cats. Effective remediation would require painting to encapsulate existing dander on the wall, removal of the carpet, and cleaning the duct work to reduce risk of impact on you. Typical cost in your area is $3,000-5,000.

mated cost of improvements for each property. The comparison allows a prospective buyer to compare purchase costs for each property against an estimated cost of improvements for the property.

In one embodiment, the investment risk application 800 comprises an adaptive question selection unit 804 for adaptively selecting questions from the collection 264.

In one embodiment, the investment risk application 800 comprises a weightings unit 802. The weightings units 802 comprises, but is not limited to, the following: (a) different weighting values for different attributes, factors or indexes, (b) different prevalence values for different attributes, factors or indexes, and (c) data representing interrelationships between different attributes, factors or indexes.

The investment risk application 800 comprises an investment risk comparison report unit 803 for generating an investment risk comparison report. FIG. 22 illustrates an Table 19 below provides another example inspection report generated by the virtual inspection application 490.

example investment risk comparison report 850, in accordance with an embodiment of the invention.

TABLE 19

Sample Occupant Report
Based on the characteristics of your property and your answers about how the house has impacted you we recommend the following interventions prioritized by what has proven to be the highest efficacy when applied to properties with similar characteristics and climate conditions to yours.
1. Data -
Your property is 10 years old and the photo #4 provide of the furnace appears to show it is of the same age. You have a crawlspace and the ducts travel through the crawlspace. 10 year old ducts typically leak and draw crawlspace air into the property. You answered that your typically sneeze when the furnace comes on.
Solution
We recommend cleaning and sealing the duct work as a minimum. It would be better to replace it. We recommend air sealing between the crawlspace and the property as well as sealing the dirt floor of the crawlspace with a layer of poly as outlined. 80% of people who own properties with characteristics like yours report significant improvements in how they feel after implementing this strategy.
Crawlspace Air Sealing - Click this link
Crawlspace Floor Sealing - Click this link
How to hire a local installer - Click to see video.

Investment Risk Application

Figure 21:
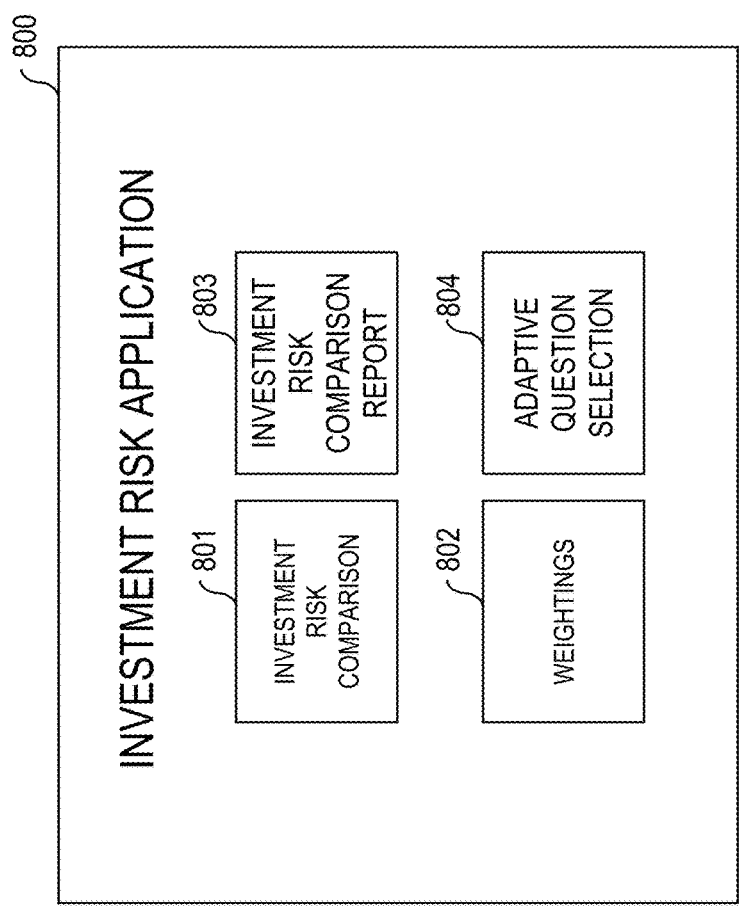
FIG. 21 illustrates an example investment risk application 800, in accordance with an embodiment of the invention.
Figure 23:
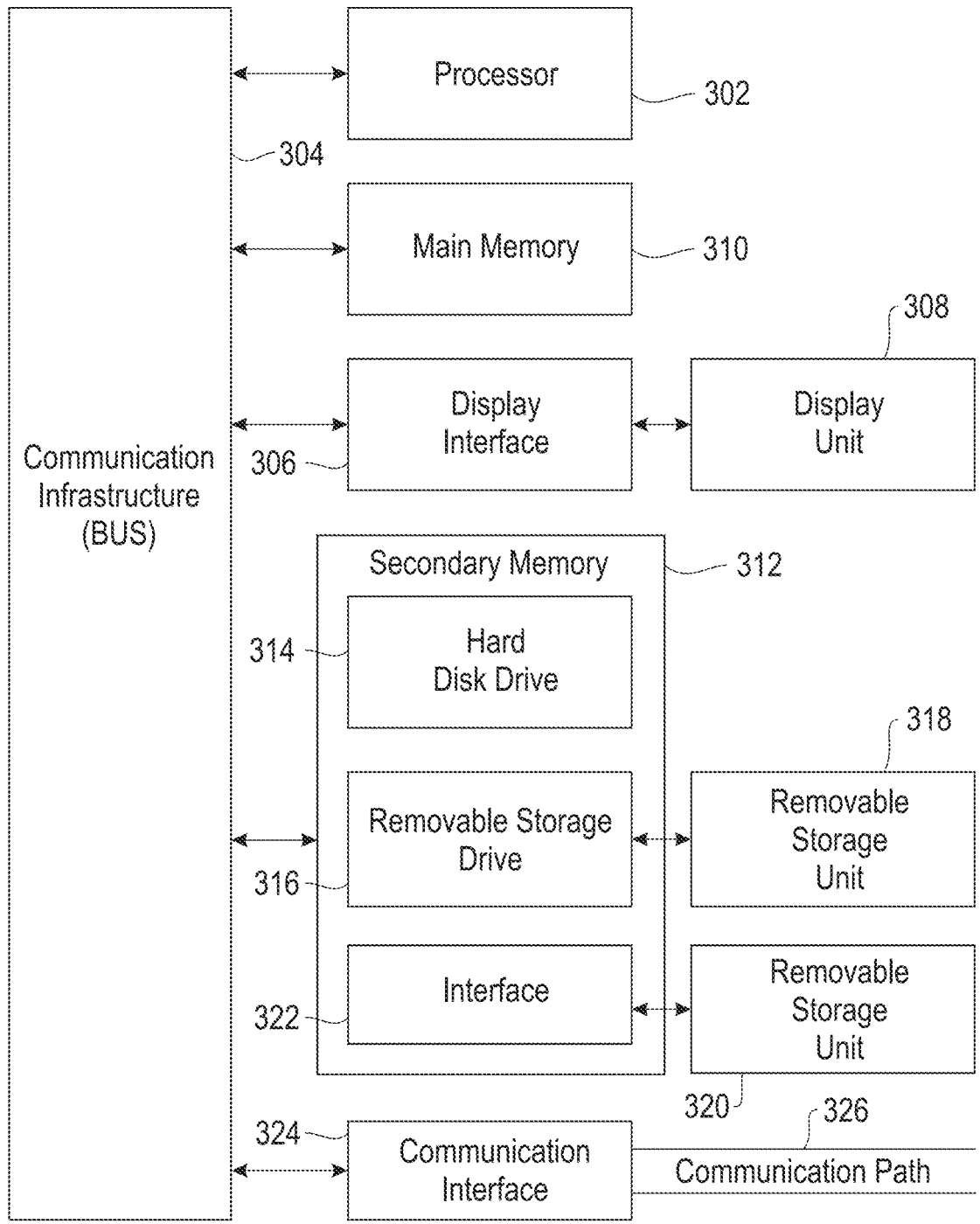
FIG. 23 is a high level block diagram showing an information processing system useful for implementing an embodiment of the present invention.

FIG. 21 illustrates an example investment risk application 800, in accordance with an embodiment of the invention. In one embodiment, one of the applications 410 (FIG. 2) executing/operating on the server devices 210 (FIG. 1) is an investment risk application 800. The investment risk application 800 comprises an investment risk comparison unit 801 configured to compare property scores and/or property match scores for multiple properties, and provide an esti- FIG. 23 is a high level block diagram showing an information processing system 300 useful for implementing one embodiment of the invention. The computer system includes one or more processors, such as processor 302. The processor 302 is connected to a communication infrastructure 304 (e.g., a communications bus, cross-over bar, or network).

The computer system can include a display interface 306 that forwards graphics, text, and other data from the communication infrastructure 304 (or from a frame buffer not shown) for display on a display unit 308. The computer system also includes a main memory 310, preferably random access memory (RAM), and may also include a secondary memory 312. The secondary memory 312 may include, for example, a hard disk drive 314 and/or a removable storage drive 316, representing, for example, a floppy disk drive, a magnetic tape drive, or an optical disk drive. The removable storage drive 316 reads from and/or writes to a removable storage unit 318 in a manner well known to those having ordinary skill in the art. Removable storage unit 318 represents, for example, a floppy disk, a compact disc, a magnetic tape, or an optical disk, etc. which is read by and written to by removable storage drive 316. As will be appreciated, the removable storage unit 318 includes a computer readable medium having stored therein computer software and/or data.

In alternative embodiments, the secondary memory 312 may include other similar means for allowing computer programs or other instructions to be loaded into the computer system. Such means may include, for example, a removable storage unit 320 and an interface 322. Examples of such means may include a program package and package interface (such as that found in video game devices), a removable memory chip (such as an EPROM, or PROM) and associated socket, and other removable storage units 320 and interfaces 322, which allows software and data to be transferred from the removable storage unit 320 to the computer system.

The computer system may also include a communication interface 324.

Communication interface 324 allows software and data to be transferred between the computer system and external devices. Examples of communication interface 324 may include a modem, a network interface (such as an Ethernet card), a communication port, or a PCMCIA slot and card, etc. Software and data transferred via communication interface 324 are in the form of signals which may be, for example, electronic, electromagnetic, optical, or other signals capable of being received by communication interface 324. These signals are provided to communication interface 324 via a communication path (i.e., channel) 326. This communication path 326 carries signals and may be implemented using wire or cable, fiber optics, a phone line, a cellular phone link, an RF link, and/or other communication channels.

The present invention may be a system, a method, and/or a computer program product. The computer program product may include a computer readable storage medium (or media) having computer readable program instructions thereon for causing a processor to carry out aspects of the present invention. The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

From the above description, it can be seen that the present invention provides a system, computer program product, and method for implementing the embodiments of the invention. The present invention further provides a non-transitory computer-useable storage medium for implementing the embodiments of the invention. The non-transitory computer-useable storage medium has a computer-readable program, wherein the program upon being processed on a computer causes the computer to implement the steps of the present invention according to the embodiments described herein. References in the claims to an element in the singular is not intended to mean "one and only" unless explicitly so stated, but rather "one or more." All structural and functional equivalents to the elements of the above-described exemplary embodiment that are currently known or later come to be known to those of ordinary skill in the art are intended to be encompassed by the present claims. No claim element herein is to be construed under the provisions of 35 U.S.C. section 112, sixth paragraph, unless the element is expressly recited using the phrase "means for" or "step for."

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A method comprising:
    collecting information relating to a property area and an occupant of the property area, wherein the information is indicative of one or more health sensitivities of the occupant;
    identifying, based on the information, interstitial spaces, pathways, and surfaces of the property area that are susceptible to accumulation of one or more particulates that affect the one or more health sensitivities of the occupant;
    detecting one or more real time changes in an environmental context of the property area utilizing one or more sensors, wherein the one or more real time changes detected impact the accumulation of the one or more particulates and in turn, affects the one or more health sensitivities of the occupant;
    determining, based on the information, the one or more real time changes detected, and the interstitial spaces, pathways, and surfaces identified, one or more recommended actions to reduce effects of the one or more real time changes detected on the one or more health sensitivities of the occupant; and
    generating and transmitting one or more electronic communications containing the one or more recommended actions to the occupant over a computer network in real time, so that the occupant has immediate access to the one or more electronic communications via at least one electronic device connected to the computer network.

2. The method of claim 1, wherein the interstitial spaces, pathways, and surfaces identified comprise at least one of: wall cavities, crawlspaces, attics, surfaces susceptible to infestations, surfaces that are hard to clean, surfaces that are cold, or pathways for air, moisture, particulates, spores, pollen, insects, and pests.

3. The method of claim 1, wherein the one or more particulates comprise at least one of: moisture, dust, pollen, dander, irritants, asthmagens, pathogens, poison, toxin, allergens, gases, chemicals, emissions, spores, pollen, insects, or pests.

4. The method of claim 1, wherein the information further comprises at least one of: one or more climate conditions of the property area, public data relating to the property area and any construction on the property area, or image data of the property area.

5. The method of claim 1, wherein the information is collected from at least one of: user input, or a third-party data source.

6. The method of claim 1, further comprising:
determining, based on the information and the interstitial spaces, pathways, and surfaces identified, one or more potential impacts of the accumulation of the one or more particulates on an individual health of the occupant with the one or more health sensitivities;
wherein the one or more recommended actions reduce the one or more potential impacts.

7. The method of claim 6, wherein the one or more recommended actions include at least one of: an action that alters a habit of the occupant, an action that physically improves the property area, or an action that that improves the individual health of the occupant.

8. The method of claim 1, further comprising:
monitoring the environmental context of the property area utilizing the one or more sensors;
wherein the one or more electronic communications identify the one or more real time changes detected; and
wherein the one or more real time changes detected comprise one or more local climatic changes on the property area.

9. A system comprising a computer processor, a computer-readable hardware storage medium, and program code embodied with the computer-readable hardware storage medium for execution by the computer processor to implement a method comprising:
collecting information relating to a property area and an occupant of the property area, wherein the information is indicative of one or more health sensitivities of the occupant;
identifying, based on the information, interstitial spaces, pathways, and surfaces of the property area that are susceptible to accumulation of one or more particulates that affect the one or more health sensitivities of the occupant;
detecting one or more real time changes in an environmental context of the property area utilizing one or more sensors, wherein the one or more real time changes detected impact the accumulation of the one or more particulates and in turn, affects the one or more health sensitivities of the occupant;
determining, based on the information, the one or more real time changes detected, and the interstitial spaces, pathways, and surfaces identified, one or more recommended actions to reduce effects of the one or more real time changes detected on the one or more health sensitivities of the occupant; and
generating and transmitting one or more electronic communications containing the one or more recommended actions to the occupant over a computer network in real time, so that the occupant has immediate access to the one or more electronic communications via at least one electronic device connected to the computer network.

10. The system of claim 9, wherein the interstitial spaces, pathways, and surfaces identified comprise at least one of: wall cavities, crawlspaces, attics, surfaces susceptible to infestations, surfaces that are hard to clean, surfaces that are cold, or pathways for air, moisture, particulates, spores, pollen, insects, and pests.

11. The system of claim 9, wherein the one or more particulates comprise at least one of: moisture, dust, pollen, dander, irritants, asthmagens, pathogens, poison, toxin, allergens, gases, chemicals, emissions, spores, pollen, insects, or pests.

12. The system of claim 9, wherein the information further comprises at least one of: one or more climate conditions of the property area, public data relating to the property area and any construction on the property area, or image data of the property area.

13. The system of claim 9, wherein the information is collected from at least one of: user input, or a third-party data source.

14. The system of claim 9, wherein the method further comprises:
determining, based on the information and the interstitial spaces, pathways, and surfaces identified, one or more potential impacts of the accumulation of the one or more particulates on an individual health of the occupant with the one or more health sensitivities;
wherein the one or more recommended actions reduce the one or more potential impacts.

15. The system of claim 14, wherein the one or more recommended actions include at least one of: an action that alters a habit of the occupant, an action that physically improves the property area, or an action that that improves the individual health of the occupant.

16. The system of claim 9, wherein the method further comprises:
monitoring the environmental context of the property area utilizing the one or more sensors;
wherein the one or more electronic communications identify the one or more real time changes detected; and
wherein the one or more real time changes detected comprise one or more local climatic changes on the property area.

17. A computer program product comprising a computer-readable hardware storage medium having program code embodied therewith, the program code being executable by a computer to implement a method comprising:
collecting information relating to a property area and an occupant of the property area, wherein the information is indicative of one or more health sensitivities of the occupant;
identifying, based on the information, interstitial spaces, pathways, and surfaces of the property area that are susceptible to accumulation of one or more particulates that affect the one or more health sensitivities of the occupant;
detecting one or more real time changes in an environmental context of the property area utilizing one or more sensors, wherein the one or more real time changes detected impact the accumulation of the one or more particulates and in turn, affects the one or more health sensitivities of the occupant;
determining, based on the information, the one or more real time changes detected, and the interstitial spaces, pathways, and surfaces identified, one or more recommended actions to reduce effects of the one or more real time changes detected on the one or more health sensitivities of the occupant; and
generating and transmitting one or more electronic communications containing the one or more recommended actions to the occupant over a computer network in real time, so that the occupant has immediate access to the one or more electronic communications via at least one electronic device connected to the computer network.

18. The computer program product of claim 17, wherein the interstitial spaces, pathways, and surfaces identified comprise at least one of: wall cavities, crawlspaces, attics, surfaces susceptible to infestations, surfaces that are hard to clean, surfaces that are cold, or pathways for air, moisture, particulates, spores, pollen, insects, and pests.

19. The computer program product of claim 17, wherein the one or more particulates comprise at least one of:

moisture, dust, pollen, dander, irritants, asthmagens, pathogens, poison, toxin, allergens, gases, chemicals, emissions, spores, pollen, insects, or pests.

20. The computer program product of claim 17, wherein the information further comprises at least one of: one or more climate conditions of the property area, public data relating to the property area and any construction on the property area, or image data of the property area.

* * * * *